(12) United States Patent
Chen et al.

(10) Patent No.: US 7,351,857 B2
(45) Date of Patent: Apr. 1, 2008

(54) METHODS OF USING SUBSTITUTED TETRALINS AND INDANES

(75) Inventors: Xiaoli Chen, Belle Mead, NJ (US); Keith T. Demarest, Flemington, NJ (US); Jung Lee, Ambler, PA (US); Jay M. Matthews, Lansdale, PA (US); Philip Rybczynski, Branchburg, NJ (US)

(73) Assignee: Janssen Pharmaceutica N.V., Beerse (BE)

( * ) Notice: Subject to any disclaimer, the term of this patent is extended or adjusted under 35 U.S.C. 154(b) by 76 days.

(21) Appl. No.: 11/145,119

(22) Filed: Jun. 3, 2005

(65) Prior Publication Data

US 2006/0074130 A1    Apr. 6, 2006

Related U.S. Application Data

(63) Continuation-in-part of application No. 10/688,379, filed on Oct. 17, 2003, now abandoned.

(60) Provisional application No. 60/495,788, filed on Aug. 15, 2003, provisional application No. 60/420,026, filed on Oct. 21, 2002.

(51) Int. Cl.
*C07C 241/00* (2006.01)
*C07C 315/00* (2006.01)
*A01N 37/12* (2006.01)

(52) U.S. Cl. ............... 562/439; 514/562; 514/563; 562/428

(58) Field of Classification Search ............ 562/439
See application file for complete search history.

(56) References Cited

U.S. PATENT DOCUMENTS

| | | | |
|---|---|---|---|
| 6,028,109 A | 2/2000 | Willson | |
| 6,300,339 B1 | 10/2001 | Jeppesen et al. | |
| 6,306,854 B1 | 10/2001 | Brown et al. | |
| 6,750,236 B2 | 6/2004 | Urbahns et al. | |
| 2005/0240049 A1* | 10/2005 | Zhang-Plasket et al. | 560/34 |
| 2006/0094786 A1* | 5/2006 | Chen et al. | 514/562 |
| 2006/0247314 A1* | 11/2006 | Chen et al. | 514/562 |

FOREIGN PATENT DOCUMENTS

| EP | 399422 A1 | 11/1990 |
|---|---|---|
| EP | 0933422 A1 | 4/1999 |
| WO | WO 92/10468 A1 | 6/1992 |
| WO | WO 95/04713 A1 | 2/1995 |
| WO | WO 97/36579 A1 | 10/1997 |
| WO | WO 00/23407 A2 | 4/2000 |
| WO | WO 00/71506 A2 | 11/2000 |
| WO | WO 02/28821 A2 | 4/2002 |
| WO | WO 02/064130 A1 | 8/2002 |
| WO | WO 02/064146 A1 | 8/2002 |
| WO | WO 02/064549 A1 | 8/2002 |

OTHER PUBLICATIONS

PCT International Search Report dated Mar. 25, 2004 for PCT Application No. PCT/EP03/033371 which relates to U.S. Appl. No. 11/145,119.
Assismacopoulos-Jeannet, F. et al. "Effect of a peroxisome proliferator on β-oxidation and overall energy balance in obese (fa/fa) rats". *America Phy. Soc.*, 1991, pp. R278-R283.
Kliewer, S. A. et al., "Fatty acids and eicosanoids regulate gene expression through direct interactions with peroxisome prolideratio-activated receptors α and γ." *Proc. Natl. Acad. Sci.*, 1997, vol. 94, pp. 4318-4323.
Cecchi, R. et al., "Synthesis and β-adrenergic activity of atypical phenylethanolaminotetralin stereoisomers." *Eur. J. Med. Chem.* 1994, vol. 29, pp. 259-267.
Brown, P. J. et al., "Identification of peroxisome proliferators-activated receptor ligands from a biased chemical library", *Chem. & Bio.*, 1997, vol. 4, No. 12, pp. 909-918.
Brown, P. J. et al., "Generation of Secondary Alkyl Amines on Solid Support by Borane Reduction: Application to the Parallel Synthesis of PPAR Lignads", *Synthesis*, 1997, pp. 778-782.
Hawke, R. L., et al., "Potent pypocholesterolemic activity of novel ureido phenoxyisobutyrates correlates with their Intrinsic fibrate potency and not with their ACAT inhibitory activity." *J. Lipid Res.*, 1997, vol. 38, pp. 1189-1203.
Brown, P. J. et al., "Identification of peroxisome proliferator-activated receptor ligands from a biased chemical library." *Chem. & Bio.*, 1997, vol. 4, No. 12, pp. 909-918.
Brown, P. J., "A Ureido-Thiosobutyric Acid (GW9578) Is a Sub-type-Selective PPAR α Agonist with Potent Lipid-Lowering Activity." *J. Med. Chem.*, 1999, vol. 42, pp. 3785-3788.
Guerre-Millo, M. et al., "Peroxisome Proliferator-activated Receptor α Activators Improve Insulin Sensitivity and Reduce Adiposity." *J. Bio. Chem.*, 2000, vol. 275, No. 22, pp. 16638-42.
Brown, P.J., "Identification of a Subtype Selective Human PPAR α Agonist Through Parallel-Array Synthesis." *Bioorg. Med. Chem. Lett.*, 2001, vol. 11, pp. 1225-1227.

* cited by examiner

*Primary Examiner*—Yvonne Eyler
*Assistant Examiner*—MLouisa Lao
(74) *Attorney, Agent, or Firm*—Evelyn D. Chen; Jeremy K. McKown

(57) ABSTRACT

The invention features tetralin and indane compounds, compositions containing them, and methods of using them as PPAR alpha modulators to treat or inhibit the progression of, for example, diabetes.

43 Claims, No Drawings

SEQUENCE LISTING

<160> NUMBER OF SEQ ID NOS: 20

<210> SEQ ID NO 1
<211> LENGTH: 47
<212> TYPE: DNA
<213> ORGANISM: Homo sapiens

<400> SEQUENCE: 1
cattttgtga gttttctagg attattcttt tctcttggaa agaaagt       47

<210> SEQ ID NO 2
<211> LENGTH: 39
<212> TYPE: DNA
<213> ORGANISM: Homo sapiens

<400> SEQUENCE: 2
atgttaggtt tggccatgcc tttctcttgg aaagaaagt       39

<210> SEQ ID NO 3
<211> LENGTH: 41
<212> TYPE: DNA
<213> ORGANISM: Homo sapiens

<400> SEQUENCE: 3
cctctcgttt tctctttatg gttttctctt ggaaagaaag t       41

<210> SEQ ID NO 4
<211> LENGTH: 47
<212> TYPE: DNA
<213> ORGANISM: Homo sapiens

<400> SEQUENCE: 4
gcttatgctc tctcataaac tctcgtggtt tctcttggaa agaaagt       47

<210> SEQ ID NO 5
<211> LENGTH: 46
<212> TYPE: DNA
<213> ORGANISM: Homo sapiens

<400> SEQUENCE: 5
ccaggtacct acaaaagcat cacatttagg cataggaccc gtgtct       46

<210> SEQ ID NO 6
<211> LENGTH: 50
<212> TYPE: DNA
<213> ORGANISM: Homo sapiens

<400> SEQUENCE: 6
gcccactcct acttctttca tataatcatt taggcatagg acccgtgtct       50

```
<210> SEQ ID NO 7
<211> LENGTH: 43
<212> TYPE: DNA
<213> ORGANISM: Homo sapiens

<400> SEQUENCE: 7
agccactttc ctggtggcaa atttaggcat aggacccgtg tct                    43

<210> SEQ ID NO 8
<211> LENGTH: 45
<212> TYPE: DNA
<213> ORGANISM: Homo sapiens

<400> SEQUENCE: 8
catccccatt cacactgatg atctttaggc ataggacccg tgtct                  45

<210> SEQ ID NO 9
<211> LENGTH: 48
<212> TYPE: DNA
<213> ORGANISM: Homo sapiens

<400> SEQUENCE: 9
gtaccaggac acccccatct aaggttttta ggcataggac ccgtgtct               48

<210> SEQ ID NO 10
<211> LENGTH: 51
<212> TYPE: DNA
<213> ORGANISM: Homo sapiens

<400> SEQUENCE: 10
ggttgatttt ccatcccatt tctgcacatt ttaggcatag acccgtgtc t            51

<210> SEQ ID NO 11
<211> LENGTH: 45
<212> TYPE: DNA
<213> ORGANISM: Homo sapiens

<400> SEQUENCE: 11
gcattccacc accagtttat cattttaggc ataggacccg tgtct                  45

<210> SEQ ID NO 12
<211> LENGTH: 52
<212> TYPE: DNA
<213> ORGANISM: Homo sapiens

<400> SEQUENCE: 12
gcgaacttca gtccaggtca acgtcccttg tttaggcata ggacccgtgt ct          52

<210> SEQ ID NO 13
<211> LENGTH: 48
<212> TYPE: DNA
<213> ORGANISM: Homo sapiens

<400> SEQUENCE: 13
tcccacagaa tgttgtagag ttcaatttta ggcataggac ccgtgtct               48

<210> SEQ ID NO 14
<211> LENGTH: 51
<212> TYPE: DNA
<213> ORGANISM: Homo sapiens

<400> SEQUENCE: 14
aaaacaacaa tatctttttg aacaatatat ttaggcatag acccgtgtc t            51
```

```
<210> SEQ ID NO 15
<211> LENGTH: 26
<212> TYPE: DNA
<213> ORGANISM: Homo sapiens

<400> SEQUENCE: 15
tcaaagtttt cactggagac aagttt                                      26

<210> SEQ ID NO 16
<211> LENGTH: 29
<212> TYPE: DNA
<213> ORGANISM: Homo sapiens

<400> SEQUENCE: 16
aaaggtactt tcagatttaa tggtgatca                                   29

<210> SEQ ID NO 17
<211> LENGTH: 33
<212> TYPE: DNA
<213> ORGANISM: Homo sapiens

<400> SEQUENCE: 17
ctggcccagt atgaaggaaa tctcagtatt ttt                              33

<210> SEQ ID NO 18
<211> LENGTH: 23
<212> TYPE: DNA
<213> ORGANISM: Homo sapiens

<400> SEQUENCE: 18
tctgcagtga cttcgtcaaa ttc                                         23

<210> SEQ ID NO 19
<211> LENGTH: 24
<212> TYPE: DNA
<213> ORGANISM: Homo sapiens

<400> SEQUENCE: 19
atggtgctct tgactttcct gtca                                        24

<210> SEQ ID NO 20
<211> LENGTH: 19
<212> TYPE: DNA
<213> ORGANISM: Homo sapiens

<400> SEQUENCE: 20
aagtgacgcc tttcatgac                                              19
```

METHODS OF USING SUBSTITUTED TETRALINS AND INDANES

CROSS-REFERENCE TO RELATED APPLICATIONS

This application is a continuation-in-part of application Ser. No. 10/688,379, filed on Oct. 17, 2003 now abandoned, which claims the benefit of U.S. provisional patent application No. 60/420,026 filed on Oct. 21, 2002 and U.S. provisional patent application No. 60/495,788 filed on Aug. 15, 2003 entitled, "METHODS OF USING SUBSTITUTED TETRALINS AND INDANES", the contents of which are hereby incorporated by reference.

FIELD OF THE INVENTION

The invention features substituted tetralin and indane derivatives, compositions containing them, and methods of using them.

BACKGROUND

A member of the nuclear receptor family, a group of ligand-activated transcription factors, the peroxisome proliferator-activated receptor alpha (PPAR alpha) is a necessary transcription factor regulating genes relating to fatty acid metabolism and insulin action.

PPAR alpha receptors are found predominantly in the liver. The genes regulated by PPAR alpha include enzymes involved in the beta-oxidation of fatty acids, the liver fatty acid transport protein, and apo A1, an important component of high density lipoproteins (HDL). Selective, high affinity PPAR alpha agonists increase hepatic fatty acid oxidation, which in turn decreases circulating triglycerides and free fatty acids. The reduction of circulating triglycerides may mediate the observed decrease, or improvement, in insulin resistance in insulin resistant or diabetic animals when treated with PPAR alpha agonists. Such treatment in animal obesity models is associated with weight loss. Known as treatments for hyperlipidemia, fibrates are weak PPAR alpha agonists.

Examples of known PPAR alpha agonists variously useful for hyperlipidemia, diabetes, or atherosclerosis include fibrates such as fenofibrate (Fournier), gemfibrozil (Parke-Davis/Pfizer, Mylan, Watson), clofibrate (Wyeth-Ayerst, Novopharm), bezafibrate, and ciprofibrate and ureidofibrates such as GW 7647, GW 9578, and GW 9820 (GlaxoSmithKline). Known PPAR alpha/gamma dual agonists useful as insulin sensitizers include ragaglitazar (Novo Nordisk), tesaglitazar (AstraZeneca), and GW 409544 (GlaxoSmithKline/Ligand Pharmaceuticals).

SUMMARY

The invention features compounds of formula (I) below:

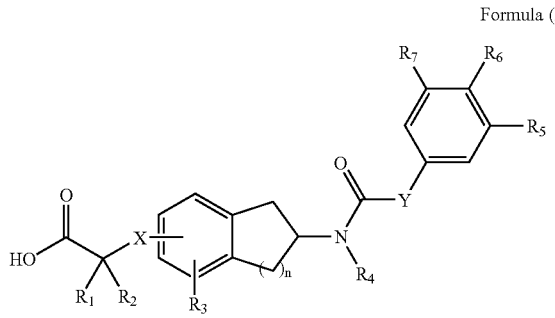

Formula (I)

or a pharmaceutically acceptable salt, $C_{1-6}$ ester or $C_{1-6}$ amide thereof, wherein each of $R_1$ and $R_2$ is independently H, $C_{1-6}$ alkyl, $(CH_2)_m NR_aR_b$, $(CH_2)_m OR_8$, $(CH_2)_m NH(CO)R_8$, or $(CH_2)_m CO_2R_8$, where each of $R_a$, $R_b$, and $R_8$ is independently H or $C_{1-6}$ alkyl, or $R_1$ and $R_2$ taken together with the carbon atom to which they are attached are a $C_{3-7}$ cycloalkyl;

m is between 1 and 6;

n is 1 or 2;

X is O or S; wherein X is at the 5 or 6 position when n is 1; and wherein X is at the 6 or 7 position when n is 2;

$R_3$ is H, phenyl, $C_{1-3}$ alkoxy, $C_{1-3}$ alkylthio, halo, cyano, $C_{1-6}$ alkyl, nitro, $NR_9R_{10}$, $NHCOR_{10}$, $CONHR_{10}$; and $COOR_{10}$; and $R_3$ is ortho or meta to X;

$R_4$ is H or —$(C_{1-5}$ alkylene)$R_{15}$, where $R_{15}$ is H, $C_{1-7}$ alkyl, [di($C_{1-2}$ alkyl)amino]($C_{1-6}$ alkylene), ($C_{1-3}$ alkoxyacyl)($C_{1-6}$ alkylene), $C_{1-6}$ alkoxy, $C_{3-7}$ alkenyl, or $C_{3-8}$ alkynyl, wherein $R_4$ has no more than 9 carbon atoms; $R_4$ can also be —$(C_{1-5}$ alkylene)$R_{15}$ wherein $R_{15}$ is $C_{3-6}$ cycloalkyl, phenyl, phenyl-O—, phenyl-S—, or a 5-6 membered heterocyclyl with between 1 and 2 heteroatoms selected from N, O, and S;

Y is NH, NH—$CH_2$, or O;

each of $R_5$ and $R_7$ is independently selected from H, $C_{1-6}$ alkyl, halo, cyano, nitro, $COR_{11}$, $COOR_{11}$, $C_{1-4}$ alkoxy, $C_{1-4}$ alkylthio, hydroxy, phenyl, $NR_{11}R_{12}$ and 5-6 membered heterocyclyl with between 1 and 2 heteroatoms selected from N, O, and S;

$R_6$ is selected from $C_{1-6}$ alkyl, halo, cyano, nitro, $COR_{13}$, $COOR_{13}$, $C_{1-4}$ alkoxy, $C_{1-4}$ alkylthio, hydroxy, phenyl, $NR_{13}R_{14}$ and 5-6 membered heterocyclyl with between 1 and 2 heteroatoms selected from N, O, and S;

in addition, either $R_5$ and $R_6$ or $R_6$ and $R_7$ may be taken together to be a bivalent moiety, saturated or unsaturated, selected from —$(CH_2)_3$—, —$(CH_2)_4$—, and $(CH_{1-2})_pN(CH_{1-2})_q$, p is 0-2 and q is 1-3, where the sum (p+q) is at least 2;

each of $R_9$ and $R_{10}$ is independently $C_{1-6}$ alkyl;

each of $R_{11}$, $R_{12}$, $R_{13}$ and $R_{14}$ is independently H or $C_{1-6}$ alkyl;

wherein each of the above hydrocarbyl and heterocarbyl moieties may be substituted with between 1 and 3 substituents independently selected from F, Cl, Br, I, amino, methyl, ethyl, hydroxy, nitro, cyano, and methoxy.

The invention also features compositions that include one or more compounds of formula (I) and a pharmaceutical carrier or excipient.

These compositions and the methods below may further include additional pharmaceutically active agents, such as lipid-lowering agents or blood-pressure lowering agents, or both.

Another aspect of the invention includes methods of using the disclosed compounds or compositions in various methods for preventing, treating, or inhibiting the progression of, a disease mediated by PPAR alpha. Examples of PPAR alpha-mediated diseases include dyslipidemia and atherosclerosis. Dyslipidemia includes hypertriglyceridemia, hypercholesterolemia, mixed hyperlipidemia, and hypo-HDL-cholesterolemia. For example, dyslipidemia may be one or more of the following: low HDL (<35 or 40 mg/dl), high triglycerides (>200 mg/dl), and high LDL (>150 mg/dl).

Additional features and advantages of the invention will become apparent from the detailed discussion, examples, and claims below.

DETAILED DESCRIPTION

The invention features the compounds disclosed herein and of formula (I) in the above Summary section, compositions containing them, and methods of using them.

According to one aspect of the invention, a method of treatment may be associated with improvements (e.g., decrease) in the extent, duration, or degree of edema or weight gain normally associated with other existing therapies, such as, for example, PPAR gamma agonists. Therapy that is associated with weight loss, or that is at least weight neutral, is desirable. A decrease in the degree of weight gain or edema, or an actual weight loss, generally improves overall patient health and comfort.

According to another aspect of the invention, a method of treatment may be a treatment for both dyslipidemia and a form of insulin resistance, impaired glucose tolerance, hyperinsulinemia, or Type II diabetes (early, intermediate, or late stage), by administering one or more of the disclosed compounds, optionally with one or more additional pharmaceutically-active agents. Diabetic patients may also have some degree of dyslipidemia. Dyslipidemia includes hypertriglyceridemia, hypercholesterolemia, mixed hyperlipidemia, and hypo-HDL-cholesterolemia. For example, dyslipidemia may be one or more of the following: low HDL (<35 mg/dl for men, or <39 mg/dl for women), high triglycerides (>200 mg/dl), and high LDL (>150 mg/dl). Preferred compounds of the invention are potent PPAR alpha agonists providing effects such as elevated serum levels of high density lipoproteins (HDL), improved levels of intermediate density lipoproteins (IDL), and lower serum levels of triglycerides, low density lipoproteins (LDL), atherogenic molecules, and/or free fatty acids (FFA). Such effects are advantageous for cardiovascular health, to prevent or inhibit the progression of atherosclerosis or coronary artery disease (CAD). It is therefore desirable to lower levels of triglycerides and LDL, to raise levels of HDL, and to lower total cholesterol, for example, within the parameters of generally-accepted ranges for these components.

One object of the invention is a method of treatment for both dyslipidemia and a PPAR-alpha mediated disease (such as diabetes, insulin resistance, impaired glucose tolerance, or hyperinsulinemia) by the administration of a single PPAR alpha agonist.

Another object of the invention is a PPAR-alpha selective agonist that is useful for (a) treating, preventing, or inhibiting the progression of both dyslipidemia and a PPAR-alpha mediated disease (such as diabetes, insulin resistance, impaired glucose tolerance, or hyperinsulinemia); (b) improving (e.g., lowering) serum glucose; (c) improving glucose tolerance; (d) improving serum insulin levels; (e) improving insulin sensitivity; (f) improving (e.g., lowering) serum triglyceride levels; (g) lowering LDL levels; (h) raising HDL levels; (i) lowering total cholesterol levels; or 0) any combination of the above.

The invention is further described below.

A. Terms

The following terms are defined below and by their usage throughout this disclosure.

"Alkyl" includes optionally substituted straight chain and branched hydrocarbons with at least one hydrogen removed to form a radical group. Alkyl groups include methyl, ethyl, propyl, isopropyl, butyl, isobutyl, t-butyl, 1-methylpropyl, pentyl, isopentyl, sec-pentyl, hexyl, heptyl, octyl, and so on. Alkyl includes cycloalkyl, such as cyclopropyl, cyclobutyl, cyclopentyl, and cyclohexyl.

"Alkenyl" includes optionally substituted straight chain and branched hydrocarbon radicals as above with at least one carbon-carbon double bond ($sp^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbon radicals having a mixture of double bonds and triple bonds, such as 2-penten-4-ynyl, are grouped as alkynyls herein. Alkenyl includes cycloalkenyl. Cis and trans or (E) and (Z) forms are included within the invention.

"Alkynyl" includes optionally substituted straight chain and branched hydrocarbon radicals as above with at least one carbon-carbon triple bond (sp). Alkynyls include ethynyl, propynyls, butynyls, and pentynyls. Hydrocarbon radicals having a mixture of double bonds and triple bonds, such as 2-penten-4-ynyl, are grouped as alkynyls herein. Alkynyl does not include cycloalkynyl.

"Alkoxy" includes an optionally substituted straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on. "Aminoalkyl", "thioalkyl", and "sulfonylalkyl" are analogous to alkoxy, replacing the terminal oxygen atom of alkoxy with, respectively, NH (or NR), S, and $SO_2$. Heteroalkyl includes alkoxy, aminoalkyl, thioalkyl, and so on.

"Aryl" includes phenyl, naphthyl, biphenylyl, tetrahydronaphthyl, indenyl, and so on, any of which may be optionally substituted. Aryl also includes arylalkyl groups such as benzyl, phenethyl, and phenylpropyl. Aryl includes a ring system containing an optionally substituted 6-membered carbocyclic aromatic ring, said system may be bicyclic, bridge, and/or fused. The system may include rings that are aromatic, or partially or completely saturated. Examples of ring systems include indenyl, pentalenyl, 1-4-dihydronaphthyl, indanyl, benzimidazolyl, benzothiophenyl, indolyl, benzofuranyl, isoquinolinyl, and so on.

"Heterocyclyl" includes optionally substituted aromatic and nonaromatic rings having carbon atoms and at least one heteroatom (O, S, N) or heteroatom moiety ($SO_2$, CO, CONH, COO) in the ring. Unless otherwise indicated, a heterocyclic radical may have a valence connecting it to the rest of the molecule through a carbon atom, such as 3-furyl or 2-imidazolyl, or through a heteroatom, such as N-piperidyl or 1-pyrazolyl. Preferably a monocyclic heterocyclyl has between 5 and 7 ring atoms, or between 5 and 6 ring atoms; there may be between 1 and 5 heteroatoms or heteroatom moieties in the ring, and preferably between 1 and 3, or between 1 and 2. A heterocyclyl may be saturated, unsaturated, aromatic (e.g., heteroaryl), nonaromatic, or fused.

Heterocyclyl also includes fused, e.g., bicyclic, rings, such as those optionally condensed with an optionally substituted carbocyclic or heterocyclic five- or six-membered aromatic ring. For example, "heteroaryl" includes an optionally substituted six-membered heteroaromatic ring containing 1, 2 or 3 nitrogen atoms condensed with an optionally substituted five- or six-membered carbocyclic or heterocyclic aromatic ring. Said heterocyclic five- or six-membered aromatic ring condensed with the said five- or six-membered aromatic ring may contain 1, 2 or 3 nitrogen atoms where it is a six-membered ring, or 1, 2 or 3 heteroatoms selected from oxygen, nitrogen and sulfur where it is a five-membered ring.

Examples of heterocyclyls include thiazoylyl, furyl, thienyl, pyranyl, isobenzofuranyl, pyrrolyl, imidazolyl, pyrazolyl, isothiazolyl, isoxazolyl, pyridyl, pyrazinyl, pyrimidinyl, pyridazinyl, indolizinyl, isoindolyl, indolyl, indazolyl, purinyl, quinolyl, furazanyl, pyrrolidinyl, pyrrolinyl, imdazolidinyl, imidazolinyl, pyrazolidinyl, pyrazolinyl, piperidyl, piperazinyl, indolinyl, and morpholinyl. For example, preferred heterocyclyls or heterocyclic radicals include morpholinyl, piperazinyl, pyrrolidinyl, pyridyl, cyclohexylimino, thienyl,and more preferably, piperidyl or morpholinyl.

Examples illustrating heteroaryl are thienyl, furanyl, pyrrolyl, imidazolyl, oxazolyl, thiazolyl, benzothienyl, benzofuranyl, benzimidazolyl, benzoxazolyl, benzothiazolyl.

"Acyl" refers to a carbonyl moiety attached to either a hydrogen atom (i.e., a formyl group) or to an optionally substituted alkyl or alkenyl chain, or heterocyclyl.

"Halo" or "halogen" includes fluoro, chloro, bromo, and iodo, and preferably fluoro or chloro as a substituent on an alkyl group, with one or more halo atoms, such as trifluoromethyl, trifluoromethoxy, trifluoromethylthio, difluoromethoxy, or fluoromethylthio.

"Alkanediyl" or "alkylene" represents straight or branched chain optionally substituted bivalent alkane radicals such as, for example, methylene, ethylene, propylene, butylene, pentylene or hexylene.

"Alkenediyl" represents, analogous to the above, straight or branched chain optionally substituted bivalent alkene radicals such as, for example, propenylene, butenylene, pentenylene or hexenylene. In such radicals, the carbon atom linking a nitrogen preferably should not be unsaturated.

"Aroyl" refers to a carbonyl moiety attached to an optionally substituted aryl or heteroaryl group, wherein aryl and heteroaryl have the definitions provided above. In particular, benzoyl is phenylcarbonyl.

As defined herein, two radicals, together with the atom(s) to which they are attached may form an optionally substituted 4- to 7-, 5- to 7-, or a 5- to 6-membered ring carbocyclic or heterocyclic ring, which ring may be saturated, unsaturated or aromatic. Said rings may be as defined above in the Summary of the Invention section. Particular examples of such rings are as follows in the next section.

"Pharmaceutically acceptable salts, esters, and amides" include carboxylate salts, amino acid addition salts, esters, and amides which are within a reasonable benefit/risk ratio, pharmacologically effective and suitable for contact with the tissues of patients without undue toxicity, irritation, or allergic response. These salts, esters, and amides may be, for example, $C_{1-8}$ alkyl, $C_{3-8}$ cycloalkyl, aryl, $C_{2-10}$ heteroaryl, or $C_{2-10}$ non-aromatic heterocyclic salts, esters, and amides. Salts, free acids, and esters are more preferable than amides on the terminal carboxylate/carboxylic acid group on the left of formula (I). Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See example, S. M. Berge, et al., "Pharmaceutical Salts," J. Pharm. Sci., 1977, 66:1-19 which is incorporated herein by reference. Representative pharmaceutically acceptable amides of the invention include those derived from ammonia, primary $C_{1-6}$ alkyl amines and secondary di ($C_{1-6}$ alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$ alkyl primary amines, and di ($C_{1-2}$ alkyl) amines. Representative pharmaceutically acceptable esters of the invention include $C_{1-7}$ alkyl, $C_{5-7}$cycloalkyl, phenyl, and phenyl($C_{1-6}$)alkyl esters. Preferred esters include methyl and ethyl esters.

"Patient" or "subject" includes mammals such as humans and animals (dogs, cats, horses, rats, rabbits, mice, non-human primates) in need of observation, experiment, treatment or prevention in connection with the relevant disease or condition. Preferably, the patient or subject is a human.

"Composition" includes a product comprising the specified ingredients in the specified amounts as well as any product which results from combinations of the specified ingredients in the specified amounts.

"Therapeutically effective amount" or "effective amount" means that amount of active compound or pharmaceutical agent that elicits the biological or medicinal response in a tissue system, animal or human that is being sought by a researcher, veterinarian, medical doctor or other clinician, which includes alleviation of the symptoms of the condition or disorder being treated.

Concerning the various radicals in this disclosure and in the claims, three general remarks are made. The first remark concerns valency. As with all hydrocarbon radicals, whether saturated, unsaturated or aromatic, and whether or not cyclic, straight chain, or branched, and also similarly with all heterocyclic radicals, each radical includes substituted radicals of that type and monovalent, bivalent, and multivalent radicals as indicated by the context of the claims. The context will indicate that the substituent is an alkylene or hydrocarbon radical with at least two hydrogen atoms removed (bivalent) or more hydrogen atoms removed (multivalent). An example of a bivalent radical linking two parts of the molecule is Y in formula (I) which links a phenyl substituted with $R_5$, $R_6$, and $R_7$ to the rest of the molecule.

Second, radicals or structure fragments as defined herein are understood to include substituted radicals or structure fragments. Hydrocarbyls include monovalent radicals containing carbon and hydrogen such as alkyl, alkenyl, alkynyl, cycloalkyl, and cycloalkenyl (whether aromatic or unsaturated), as well as corresponding divalent (or multi-valent) radicals such as alkylene, alkenylene, phenylene, and so on. Heterocarbyls include monovalent and divalent (or multivalent) radicals containing carbon, optionally hydrogen, and at least one heteroatom. Examples of monovalent heterocarbyls include acyl, acyloxy, alkoxyacyl, heterocyclyl, heteroaryl, aroyl, benzoyl, dialkylamino, hydroxyalkyl, and so on. Using "alkyl" as an example, "alkyl" should be understood to include substituted alkyl having one or more substitutions, such as between 1 and 5, 1 and 3, or 2 and 4 substituents. The substituents may be the same (dihydroxy, dimethyl), similar (chlorofluoro), or different (chlorobenzyl- or aminomethyl-substituted). Examples of substituted alkyl include haloalkyl (such as fluoromethyl, chloromethyl, difluoromethyl, perchloromethyl, 2-bromoethyl, trifluoromethyl, and 3-iodocyclopentyl), hydroxyalkyl (such as hydroxymethyl, hydroxyethyl, 2-hydroxypropyl, aminoalkyl (such as aminomethyl, 2-aminoethyl, 3-aminopropyl, and 2-aminopropyl), nitroalkyl, alkylalkyl, and so on. A di($C_{1-6}$ alkyl)amino group includes independently selected alkyl groups, to form, for example, methylpropylamino and isopropylmethylamino, in addition dialkylamino groups having two of the same alkyl group such as dimethyl amino or diethylamino.

Third, only stable compounds are intended. For example, where there is an $NR_{11}R_{12}$ group, and R can be an alkenyl group, the double bond is at least one carbon removed from the nitrogen to avoid enamine formation. Similarly, where —$(CH_2)_p$—N—$(CH_2)_q$— can be unsaturated, the appropriate hydrogen atom(s) is(are) included or omitted, as shown in —$(CH_2)$—N═$(CH)$—$(CH_2)$— or —$(CH_2)$—NH—$(CH)$═$(CH)$—.

Compounds of the invention are further described in the next section.

B. Compounds

The present invention features compositions containing and methods of using compounds of formula (I) as described in the Summary section above. Examples include those compounds wherein: (a) one of $R_1$ and $R_2$ is methyl or ethyl; (b) wherein each of $R_1$ and $R_2$ is methyl; (c) $R_1$ and $R_2$ taken together are cyclobutyl or cyclopentyl; (d) $R_3$ is H; (e) $R_4$ is H or $C_{2-7}$ alkyl; (e) $R_4$ is H or $C_{2-5}$ alkyl; (f) $R_4$ is ethyl; (g) $R_4$ is H; (h) n is 1; (i) n is 2; (j) Y is $NHCH_2$; (k) Y is NH; (l) X is S; (m) X is O; (n) at least one of $R_5$ and $R_7$ is H; (o) $R_6$ is $C_{1-4}$ alkyl, halomethoxy, or halothiomethoxy; (p) $R_6$ is t-butyl, isopropyl, trifluoromethyl, trifluoromethoxy, trifluorothiomethoxy, difluoromethoxy, or dimethylamino; (q) $R_3$ is H, $R_4$ is $C_{2-7}$ alkyl, and Y is NH; (r) $R_4$ is $C_{2-5}$ alkyl; (s) $R_6$ is cyclopropylmethyl, isopropyl, isobutyl, methylethylamino, or diethylamino; (t) the (S) enantiomer at the C-2 position on the indane or tetralin; (u) the (R) enantiomer at the C-2 position on the indane or tetralin; (v) where $R_{15}$ is $C_{1-7}$ alkyl, [di($C_{1-2}$ alkyl)amino]($C_{1-6}$ alkylene), ($C_{1-3}$ alkoxyacyl)($C_{1-6}$ alkylene), $C_{1-6}$ alkoxy, $C_{3-7}$ alkenyl, or $C_{3-8}$ alkynyl; (w) $R_6$ is trifluoromethylthio or trifluoromethoxy; or (x) combinations of the above.

Additional preferred compounds include:

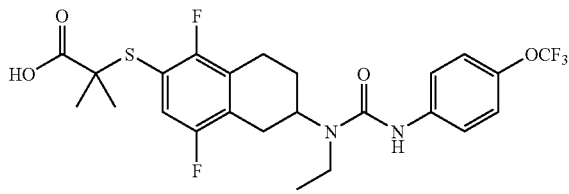

2-{6-[1-Ethyl-3-(4-trifluoromethoxy-phenyl )-ureido]-1,4-difluoro-5,6,7,8-tetrahydro-naphthalen-2-ylsulfanyl}-2-methylpropionic acid

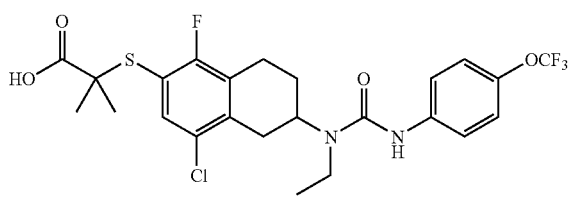

2-{4-Chloro-6-[1-ethyl-3-(4-trifluoromethoxyphenyl)ureido]-1-fluoro-5,6,7,8-tetrahydronaphthalen-2-ylsulfanyl}-2-methylpropionic acid

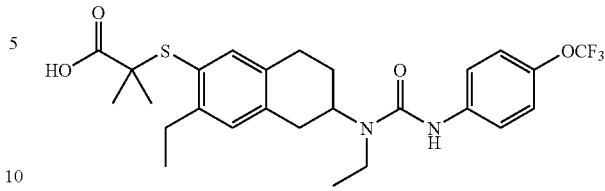

2-{3-Ethyl-6-[1-ethyl-3-(4-trifluoromethoxyphenyl)ureido]-5,6,7,8-tetrahydronaphthalen-2-ylsulfanyl}-2-methylpropionic acid

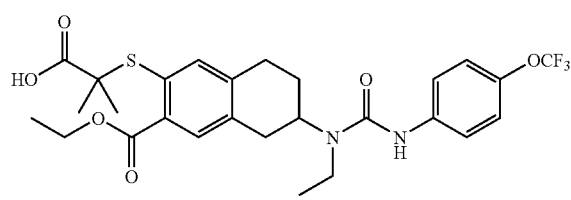

3-(1-Carboxy-1-methyl-ethylsulfanyl)-7-[1-ethyl-3-(4-trifluoromethoxyphenyl)ureido]-5,6,7,8-tetrahydronaphthalene-2-carboxylic acid ethyl ester

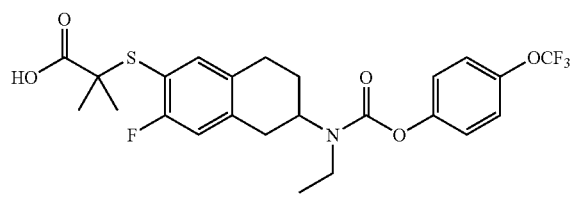

2-{6-[Ethyl-(4-trifluoromethoxyphenoxycarbonyl)-amino]-3-fluoro-5,6,7,8-tetrahydronaphthalen-2-ylsulfanyl}-2-methylpropionic acid 2-{6-[1-Ethyl-3-(4-trifluoromethoxyphenyl )ureido]-3-methoxy-5,6,7,8-tetrahydronaphthalen-2-ylsulfanyl}-2-methylpropionic acid 2-{6-[1-Ethyl-3-(4-trifluoromethoxyphenyl)ureido]-3-chloro-5,6,7,8-tetrahydronaphthalen-2-ylsulfanyl}-2-methylpropionic acid 2-{6-[1-Ethyl-3-(4-trifluoromethoxyphenyl)ureido]-3-bromo-5,6,7,8-tetrahydronaphthalen-2-ylsulfanyl}-2-methylpropionic acid 2-{6-[1-Ethyl-3-(4-trifluoromethoxyphenyl )ureido]-3-methyl-5,6,7,8-tetrahydronaphthalen-2-ylsulfanyl}-2-methylpropionic acid 2-{6-[1-Ethyl-3-(4-trifluoromethoxyphenyl)ureido]-3-trifluoromethoxy-5,6,7,8-tetrahydronaphthalen-2-ylsulfanyl}-2-methylpropionic acid 2-{6-[1-Ethyl-3-(4-hydroxyphenyl)ureido]-5,6,7,8-tetrahydronaphthalen-2-ylsulfanyl}-2-methylpropionic acid 2-{6-[4-Aminophenyl)-1-ethyl-ureido]-5,6,7,8-tetrahydronaphthalen-2-ylsulfanyl}-2-methylpropionic acid The most preferred compounds are selected from:
2-{6-[1-Ethyl-3-(4-trifluoromethoxyphenyl)ureido]-5,6,7,8-tetrahydronaphthalen-2-ylsulfanyl}-2-methylpropionic acid;
2-{6-[3-(4-trifluoromethoxyphenyl)ureido]-5,6,7,8-tetrahydronaphthalen-2-ylsulfanyl}-2-methylpropionic acid;
2-{2-[1-Ethyl-3-(4-trifluoromethoxyphenyl)ureido]indan-5-ylsulfanyl}-2-methylpropionic acid;
2-{2-[1-Ethyl-3-(4-trifluoromethylsulfanylphenyl)ureido]indan-5-ylsulfanyl}-2-methylpropionic acid;
2-{6-[1-Ethyl-3-(4-trifluoromethoxyphenyl)ureido]-3-fluoro-5,6,7,8-tetrahydronaphthalen-2-ylsulfanyl}-2-methylpropionic acid; and
2-Methyl-2-{2-[1-propyl-3-(4-trifluoromethoxyphenyl)ureido]indan-5-ylsulfanyl}propionic acid.

Related Compounds

The invention provides the disclosed compounds and closely related, pharmaceutically acceptable forms of the disclosed compounds, such as salts, esters, amides, acids, hydrates or solvated forms thereof; masked or protected forms; and racemic mixtures, or enantiomerically or optically pure forms. Related compounds also include compounds of the invention that have been modified to be detectable, e.g., isotopically labelled with $^{18}F$ for use as a probe in positron emission tomography (PET) or single-photon emission computed tomography (SPECT).

The invention also includes disclosed compounds having one or more functional groups (e.g., hydroxyl, amino, or carboxyl) masked by a protecting group. See, e.g., Greene and Wuts, *Protective Groups in Organic Synthesis*, $3^{rd}$ ed., (1999) John Wiley & Sons, NY. Some of these masked or protected compounds are pharmaceutically acceptable; others will be useful as intermediates. Synthetic intermediates and processes disclosed herein, and minor modifications thereof, are also within the scope of the invention.

Hydroxyl Protecting Groups

Protection for the hydroxyl group includes methyl ethers, substituted methyl ethers, substituted ethyl ethers, substitute benzyl ethers, and silyl ethers.

Substituted Methyl Ethers

Examples of substituted methyl ethers include methyoxymethyl, methylthiomethyl, t-butylthiomethyl, benzyloxymethyl, p-methoxybenzyloxymethyl, (4-methoxyphenoxy)methyl, t-butoxymethyl.

Substituted Ethyl Ethers

Examples of substituted ethyl ethers include 1-ethoxyethyl, 1-methyl-1-methoxyethyl, 1-methyl-1-benzyloxyethyl, 2,2,2-trichloroethyl, t-butyl, allyl, p-chlorophenyl, p-methoxyphenyl, and benzyl.

Substituted Benzyl Ethers

Examples of substituted benzyl ethers include p-methoxybenzyl, 3,4-dimethoxybenzyl, p-halobenzyl, 2,6-dichlorobenzyl, p-cyanobenzyl, p-phenylbenzyl, diphenylmethyl.

Esters

In addition to ethers, a hydroxyl group may be protected as an ester. Examples of esters include formate, benzoylformate, acetate, trichloroacetate, trifluoroacetate, methoxyacetate, phenoxyacetate, p-chlorophenoxyacetate, benzoate.

Sulfonates

Examples of sulfonates include sulfate, methanesulfonate (mesylate), benzylsulfonate, and tosylate.

Amino Protecting Groups

Protection for the amino group includes carbamates, amides, and special —NH protective groups.

Examples of carbamates include methyl and ethyl carbamates, substituted ethyl carbamates, assisted cleavage carbamates, photolytic cleavage carbamates, urea-type derivatives, and miscellaneous carbamates.

Carbamates

Examples of methyl and ethyl carbamates include methyl and ethyl, 9-fluorenylmethyl, and 4-methoxyphenacyl.

Substituted Ethyl

Examples of substituted ethyl carbamates include 2,2,2-trichloroethyl, 2-phenylethyl, t-butyl, vinyl, allyl, 1-isopropylallyl, benzyl, p-methoxybenzyl, p-nitrobenzyl, p-bromobenzyl, p-chlorobenzyl, 2,4-dichlorobenzyl and diphenylmethyl.

Photolytic Cleavage

Examples of photolytic cleavage include m-nitrophenyl, 3,5-dimethoxybenzyl, o-nitrobenzyl, 3,4-dimethoxy-6-nitrobenzyl, and phenyl(o-nitrophenyl)methyl.

Amides

Examples of amides include N-formyl, N-acetyl, N-trichloroacetyl, N-trifluoroacetyl, N-phenylacetyl, N-3-phenylpropionyl, N-picolinoyl, N-3-pyridylcarboxamide, N-benzoyl, N-p-phenylbenzoyl, and phthaloyl.

Protection for the Carbonyl Group

Cyclic Acetals and Ketals

Examples of cyclic acetals and ketals include 1,3-dioxanes and 5-methylene-1,3-dioxane.

Protection for the Carboxyl Group

Esters

Substituted Methyl Esters

Examples of substituted methyl esters include 9-fluorenylmethyl, methoxymethyl, methylthiomethyl, methoxyethoxymethyl, 2-(trimethylsilyl)ethoxymethyl, benzyloxymethyl, phenacyl, p-bromophenacyl, α-methylphenacyl, and p-methoxyphenacyl. Examples of esters also include straight chain or branched alkyl esters such as tert-butyl, ethyl, propyl, isopropyl, and butyl.

Substituted Benzyl Esters

Examples of substituted benzyl esters include triphenylmethyl, diphenylmethyl, 9-anthrylmethyl, 2,4,6-trimethylbenzyl, p-bromobenzyl, o-nitrobenzyl, p-nitrobenzyl, p-methoxybenzyl, 2,6-dimethoxybenzyl, piperonyl, 4-picolyl and p-P-benzyl.

Silyl Esters

Examples of silyl esters include trimethylsilyl, triethylsilyl, t-butyldimethylsilyl, i-propyldimethylsilyl, phenyldimethylsilyl and di-t-butylmethylsilyl.

C. Synthetic Methods

The invention provides methods of making the disclosed compounds according to traditional organic synthetic methods as well as matrix or combinatorial synthetic methods. Schemes 1 through 10 describe suggested synthetic routes. Using these Schemes, the guidelines below, and the examples, a person of skill in the art may develop analogous or similar methods for a given compound that are within the invention.

One skilled in the art will recognize that synthesis of the compounds of the present invention may be effected by purchasing an intermediate or protected intermediate compounds described in any of the schemes disclosed herein. One skilled in the art will further recognize that during any of the processes for preparation of the compounds in the present invention, it may be necessary and/or desirable to protect sensitive or reactive groups on any of the molecules concerned. This may be achieved by means of conventional protecting groups, such as those described in "Protective Groups in Organic Synthesis", John Wiley & Sons, 1991. These protecting groups may be removed at a convenient stage using methods known from the art.

Examples of the described synthetic routes include Synthetic Examples 1 through 57. Compounds analogous to the target compounds of these examples can be, and in many cases, have been, made according to similar routes. The disclosed compounds are useful in basic research and as pharmaceutical agents as described in the next section.

General Guidance

A preferred synthesis of Formula 14, when X is S (and $R_3$ is H) is demonstrated in Schemes 1-5.

Abbreviations or acronyms used herein include: AcOH (glacial acetic acid); DCC (1,3-dicyclohexylcarbodiimide); DCE (1,2-dichloroethane); DIC (2-dimethylaminoisopropyl chloride hydrochloride); DIEA (diisopropylethylamine); DMF (dimethylformamide); EDC (1-(3-dimethylaminopropyl)-3-ethylcarbodiimide); EtOAc (ethyl acetate); mCPBA (3-chloroperoxybenzoic acid); NMI (1-methylimidazole); TEA (triethylamine);TFA (trifluoroacetic acid); THF (tetrahydrofuran);TMEDA (N, N, N', N'-tetramethyl-ethylenediamine).

Scheme 1

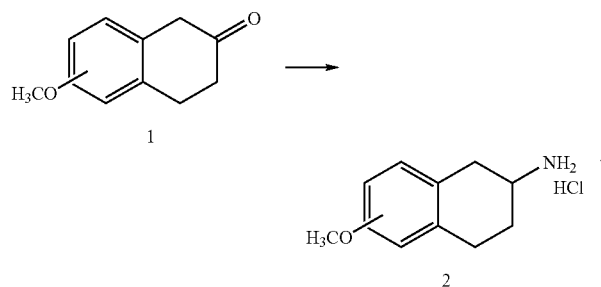

In accordance with Scheme 1, the tetralins can be made by conversion of compound 1 to compound 2. For example, a methoxy-2-tetralone, such as 6-methoxy-2-tetralone, can be treated with a reagent such as ammonium acetate or ammonia, or hydroxyl amine. The corresponding imine can be reduced with an appropriate reducing agent, such as sodium borohydride, sodium cyanoborohydride, or sodium triacetoxyborohydride and the resulting oxime can be reduced catalytically using palladium or platinum in a polar protic solvent, such as methanol, ethanol or ethyl acetate, to obtain a racemic compound 2. Preparation of the hydrochloride salt may be easily accomplished by one skilled in the art.

Scheme 2

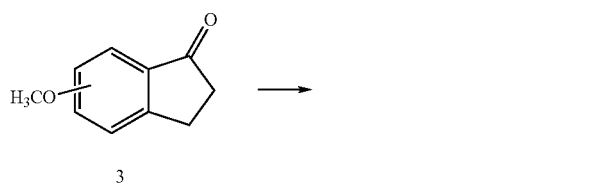

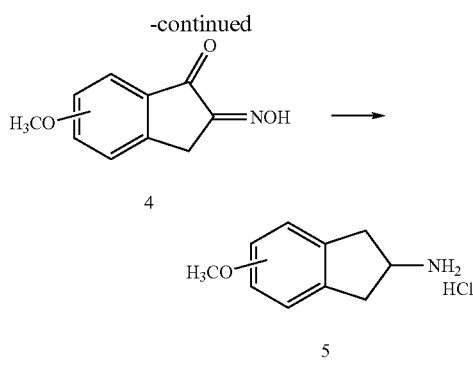

In accordance with Scheme 2, the indanes can be prepared by conversion of a compound 3 to a compound 5. For example, when a methoxy indanone, such as 5-methoxy-1-indanone, is treated with an acylating agent, such as butyl nitrite or isoamyl nitrite in the presence of a catalytic amount of acid, such as hydrochloric acid or hydrobromic acid in a polar solvent, such as methanol or ether, a keto-oxime 4 is obtained. Reduction of a compound 4 can be achieved by using the appropriate reducing agent(s), such as lithium aluminum hydride or hydrogen and a catalyst, such as palladium or platinum, in an appropriate solvent, such as acetic acid-sulfuric acid, THF, or methanol at an appropriate temperature. The choice of salt formation methods may be easily determined by one skilled in the art.

Scheme 3

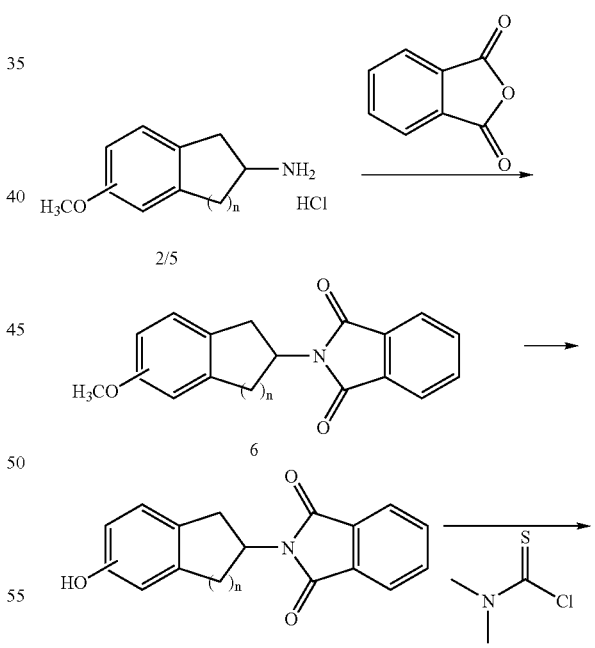

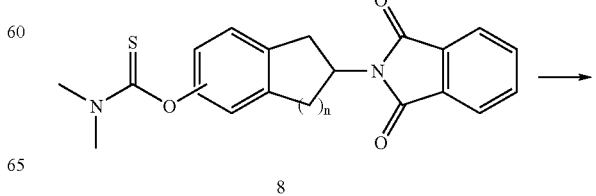

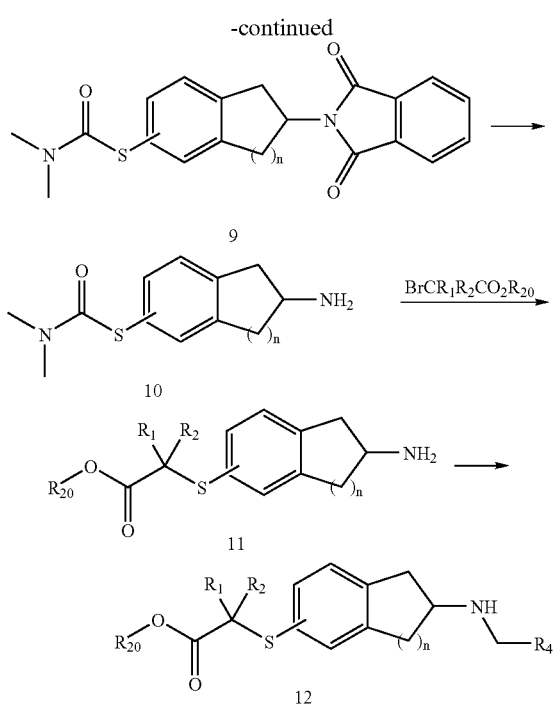

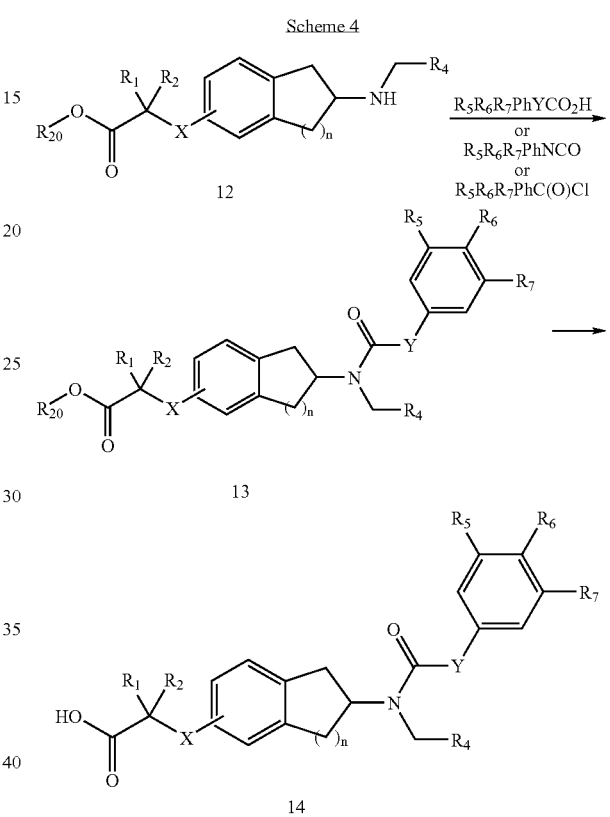

In accordance with Scheme 3, a compound 2 or 5 can be converted to a compound 12. For example, when a racemic amine hydrochloride is treated with a base, such as sodium hydride or lithium hydride in a polar aprotic solvent, such as DMF or THF and consequently reacted with an anhydride, such as phthalic anhydride at elevated temperatures, a cyclic imide 6 can be furnished. Cleavage of methyl aryl ethers of Formula 6 to a compound of the Formula 7 can be accomplished using a Lewis acid such as boron tribromide, boron trichloride, aluminum chloride or trimethylsilyliodide in nonpolar, aprotic solvents such as toluene, dichloromethane, or dichloroethane with or without cooling. Acylation of phenols of Formula 7 to a compound of Formula 8 can be achieved using thiocarbamoyl chlorides, such as dimethylaminothiocarbamoyl chloride or diethylthiocarbamoyl chloride and a non-reactive, tertiary amine, such as triethylamine, 1,8-diazabicyclo[5.4.0]undec-7-ene, or 1,4-diazabicyclo[2.2.2.]octane in an aprotic solvent such as dichloromethane, DMF, or THF with or without cooling. Compounds of Formula 8 can be rearranged thermally to compounds of Formula 9 at temperatures between 180° C. to 350° C., either neat as a melt or using high-boiling solvents such as DOWTHERM® A (a mixture of biphenyl and biphenyl ether sold by, for example, Fluka Chemical Corp., Milwaukee, Wis. USA), N,N-dimethylaniline, diphenyl ether or decalin. Compounds of Formula 10 can be prepared from compounds of Formula 9 by treating with a suitable nucleophile, such as hydrazine, disodium sulfide or methylamine in appropriate polar solvent such as ethanol or THF at elevated temperatures. Conversion of Formula 10 to compounds of Formula 11 can be achieved using an appropriate reagent, such as potassium hydroxide in an alchoholic solvent, such as ethanol or methanol, or lithium aluminum hydride in THF or ether, followed by alkylation using an appropriately substituted alkyl halide, such as tert-butyl 2-bromoisobutyrate, ethyl bromoacetate, or ethyl 2-bromobutyrate and a reducing agent, such as lithium borohydride or sodium borohydride. Compounds of Formula 11 can be substituted to provide compounds of Formula 12 using a carboxylic acid or an acid chloride and an appropriate reducing agent such as borane-THF or borane-dimethylsulfide, using aprotic solvents such as THF, dichloromethane, or hexanes. Alternatively, substitution can be accomplished using an aldehyde and a reducing agent, such as sodium cyanoborohydride or sodium triacetoxyborohydride, in appropriate aprotic solvents, such as THF, dichloromethane or dichloroethane.

In accordance to Scheme 4, compounds of Formula 13 can be prepared from compounds of Formula 12 by acylating a secondary amine with an aryl acetic acid, using thionyl chloride or oxalyl chloride neat or in toluene or dichloromethane with or without catalytic DMF. Alternatively, the coupling can be achieved using standard peptide conditions, such as EDC, DCC, or DIC in dichloromethane. When Y=NH or O, an aryl isocyanate or aryl chloroformate, respectively, in a non-polar aprotic solvent, such as THF, dichloromethane or hexanes can be used to provide compounds of Formula 13. The choice of deprotection methods may be easily determined by one skilled in the art to provide compounds of Formula 14.

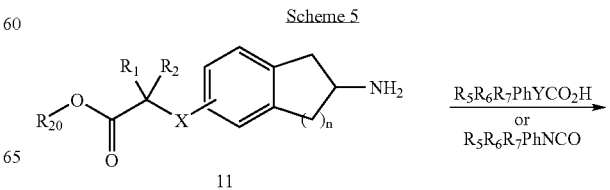

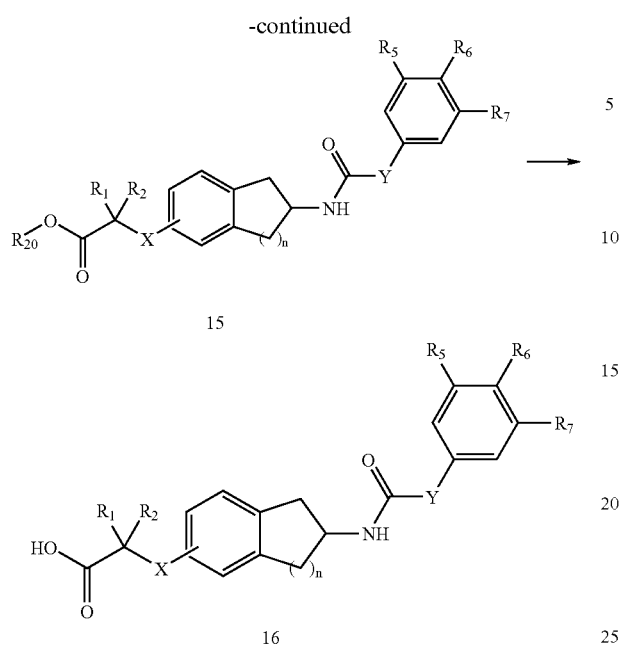

Likewise, compounds of Formula 16 can be prepared from compounds of Formula 11 by acylating the primary amine as delineated in Scheme 5 to afford compounds of Formula 15. The choice of deprotection methods may be easily determined by one skilled in the art to provide compounds of Formula 16.

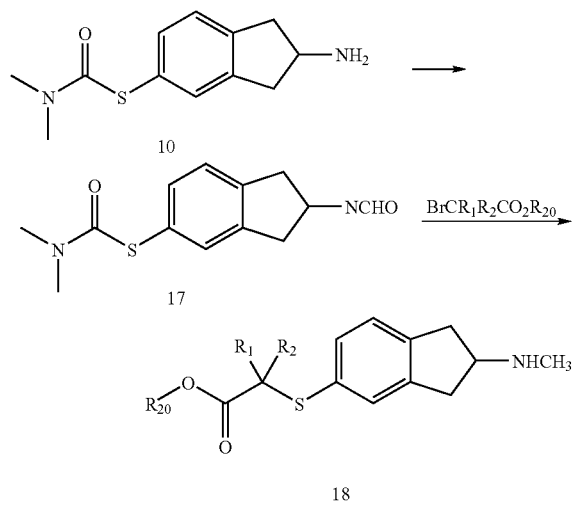

A compound of Formula 18 can be prepared from a compound of Formula 10 as demonstrated in Scheme 6. For example, compound of Formula 10 can be treated with ethyl formate or ammonium formate either neat or in the presence of a suitable solvent, such as dichloromethane or dichloroethane with or without heating to provide a compound of Formula 17. Compounds of Formula 17 can be converted to compounds of Formula 18 by using an appropriate reagent, such as lithium aluminum hydride in a suitable solvent, such as THF or ether followed by alkylation using an appropriately substituted alkyl halide, such as tert-butyl 2-bromoisobutyrate, ethyl bromoacetate, or ethyl 2-bromobutyrate and a reducing agent, such as lithium borohydride or sodium borohydride.

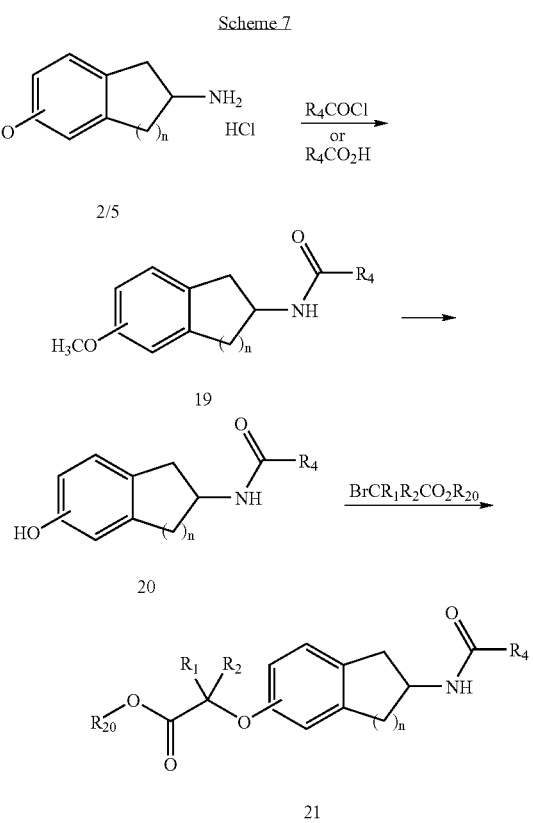

A preferred synthesis of Formula 21, when X is O (and $R_3$ is H) is demonstrated in Scheme 7. For example, when compounds of Formula 2 or 5 are acylated with a carboxylic acid or an acid chloride as described previously, compounds of Formula 19 are prepared. Cleavage of methyl aryl ethers of Formula 19 to a compound of the Formula 20 can be accomplished using a Lewis acid such as boron tribromide, boron trichloride, aluminum chloride or trimethylsilyliodide in nonpolar, aprotic solvents such as toluene, dichloromethane, or dichloroethane with or without cooling. Compounds of Formula 20 can be converted to compounds of Formula 21 by treating with an appropriate base, such as potassium carbonate, cesium carbonate or potassium hydroxide and an appropriately substituted alkyl halide, such as tert-butyl 2-bromoisobutyrate, ethyl bromoacetate, or ethyl 2-bromobutyrate in a suitable solvent, such as DMF or methanol.

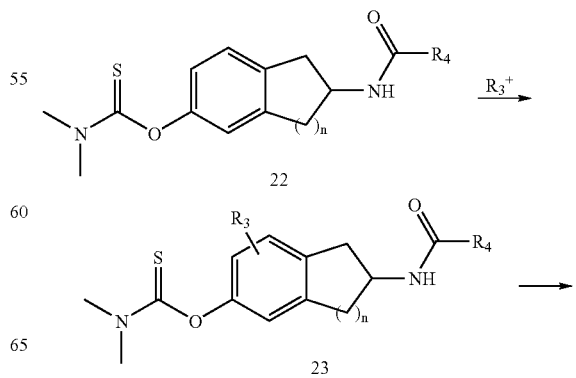

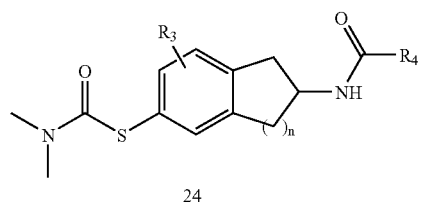
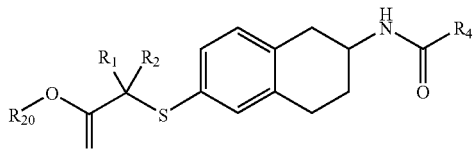

Compounds of Formula 24 can be prepared from compounds of Formula 22 as demonstrated in Scheme 8. For example, compound of Formula 22 can be treated with an appropriate base, such as butyl lithium or sec-butyl lithium in an appropriate solvent, such as ether or THF, with or without TMEDA and cooling, and the appropriate electrophile, such as alkyl halides, aldehydes, or disulfides to provide compounds of Formula 23. Compounds of Formula 23 can be converted to compounds of Formula 24 in a manner analogous to that described in Scheme 3 for the transformation of compound 8 to compound 9.

An alternative synthesis toward compounds of Formula 32 is outlined in Scheme 9. For example, when 4-methylthiophenyl acetic acid, Formula 26, is treated with oxalyl chloride or thionyl chloride in the presence of methanol, a compound of Formula 27 is afforded. Treatment of compounds of Formula 27 with a Lewis acid, such as aluminum chloride, in a chlorinated solvent such as chloroform or dichloroethane, in the presence of an alkene, such as ethylene, provides tetralones of Formula 28. Using the procedure outlined in Scheme 1, the tetralins of Formula 29 can be prepared. Compounds of Formula 29 can be substituted to provide compounds of Formula 30 using a carboxylic acid under coupling conditions outlined previously or an acid chloride with a tertiary amine, such as diisopropylethylamine or triethylamine in a suitable solvent, such as dichloromethane or dichloroethane. A compound of Formula 30 can converted to a compound of Formula 31 using with an oxidizing agent, such as mCPBA or hydrogen peroxide in a suitable solvent, such as methylene chloride, followed by subsequent treatment of compounds of Formula 30 with trifluoroacetic anhydride with or without a solvent, such as chloroform, followed by treatment with a tertiary amine, such as triethylamine or diisopropylethylamine in a suitable solvent, such as methanol affords compounds of Formula 31. Alternatively, deprotection of the thio ether in compounds of Formula 30 can be achieved using a base, such as tert-butyl sodium sulfide, sodium, sodium methyl thiol in a suitable solvent, such as DMF, N-methyl-2-pyrrolidone or ammonia to provide compounds of Formula 31. Using chemistry analogous to that described in Scheme 3 for the transformation of compound 10 to compound 11, compounds of Formula 31 can be readily converted to compounds of Formula 32.

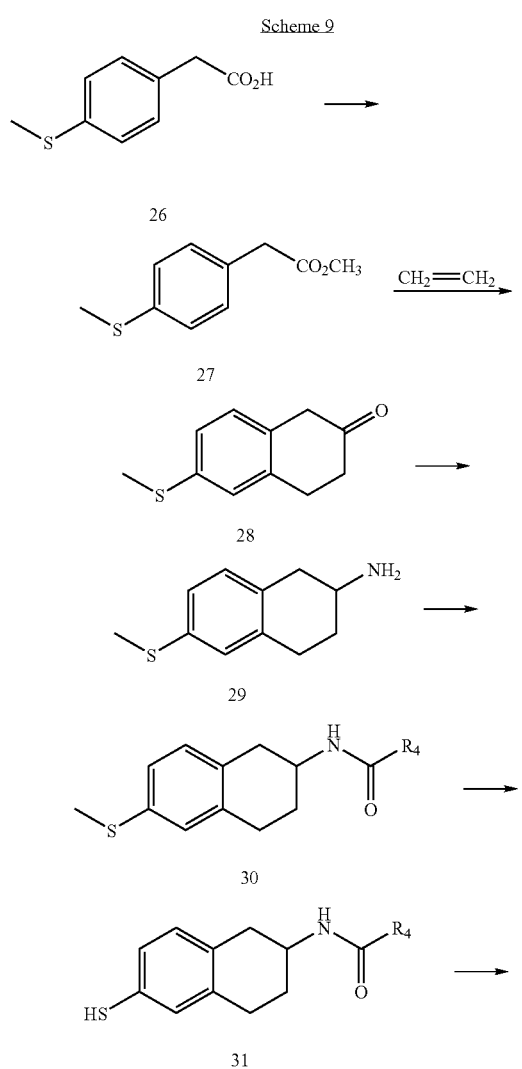

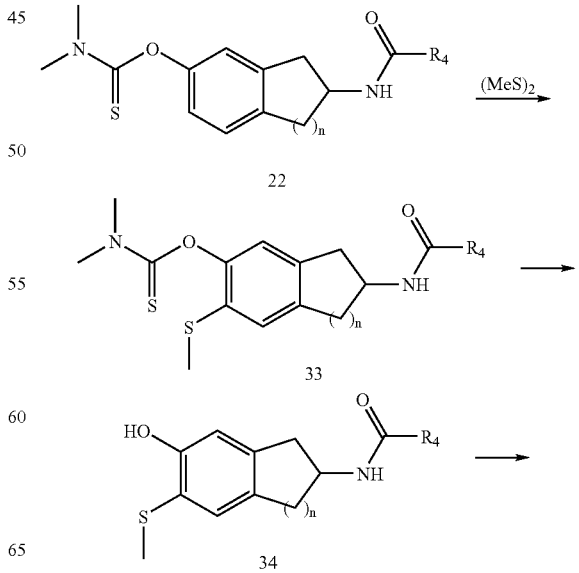

-continued

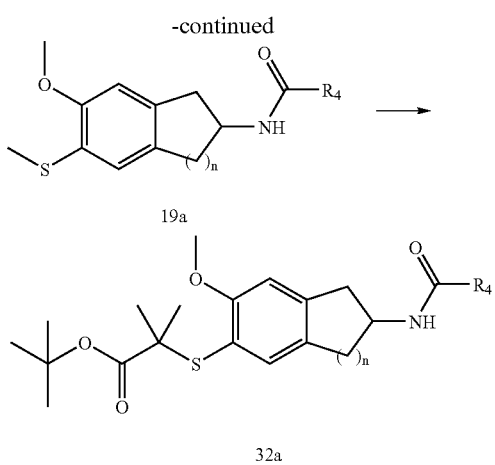

19a

32a

In accordance to Scheme 10, compounds of Formula 22 can be readily converted to compounds of Formula 32a, where $R_3=OCH_3$. For example, compounds of Formula 22 can be treated with an appropriate base, such as butyl lithium or sec-butyl lithium in an appropriate solvent, such as ether or THF, with or without TMEDA and cooling, and the appropriate disulfide, such as dimethyl disulfide or dibenzyl disulfide provide compounds of Formula 33. Removal of the dimethylamino thiocarbamate from compounds of Formula 33 is achieved using potassium or sodium hydroxide in an appropriate solvent, such as water, methanol, or ethanol with or without heating, to afford compounds of Formula 34. Compounds of Formula 34 can be methylated to provide compounds of Formula 19a by using methyl iodide, dimethylsulfate, or diazomethane in an appropriate solvent, such as DMF, methanol, or dichloromethane, with or without base, such as cesium carbonate or potassium carbonate. Using chemistry analogous to that described in Scheme 9 for the transformation of compounds of Formula 30 to Compounds of Formula 32, Compounds of Formula 32a can be readily synthesized from Compounds of Formula 19a.

Route 1

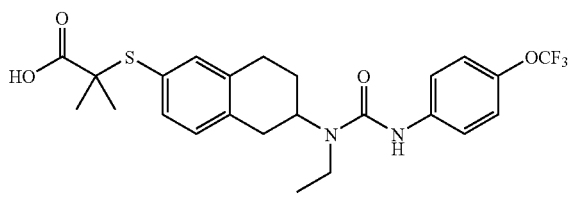

2-{6-[1-Ethyl-3-(4-trifluoromethoxyphenyl)ureido]-5,6,7,8-tetrahydronaphthal-2-ylsulfanyl}-2-methylpropionic acid Compound 1.0

EXAMPLE 1

A. 6-Methoxy-1,2,3,4-tetrahydronaphthalen-2-ylamine hydrochloride

Scheme 1. To a solution of 6-methoxy-2-tetralone (10.0 g; 56.7 mmol) dissolved in MeOH (400 mL) is added ammonium acetate (65 g; 0.84 mol) and the reaction was stirred for 30 min. at RT. To the reaction is then added sodium cyanoborohydride (17.8 g; 0.28 mol) and the reaction was refluxed for 1-2 h. The reaction is cooled, the solvent removed under reduced pressure, the residue diluted with EtOAc and 1N NaOH added to quench the reaction. The aqueous phase is separated and the organic phase washed with $H_2O$, brine, dried over $Na_2SO_4$, filtered, and the solvent removed under reduced pressure to afford a crude residue which was purified by flash chromatography ($SiO_2$) eluting with $CH_2Cl_2$/MeOH:$NH_4OH$ (10%) to provide 5.0 g (50%) of 6-methoxy-1,2,3,4-tetrahydro-naphthalen-2-ylamine as a dark oil. To a solution of titled compound in ether (100 mL) cooled to 0° C. is bubbled HCl (g) until the solution is saturated.

The suspension is stirred for an additional 30 min at RT and the solvent evaporated under reduced pressure. The remaining solid is triturated with ether, filtered, washed with ether and dried under reduced pressure to provide 4.9 g of 6-methoxy-1,2,3,4-tetrahydronaphthalen-2-ylamine hydrochloride as a white solid.

LC/MS: $C_{11}H_{15}NO$: m/z 178 (M+1)

B. 2-(6-Methoxy-1,2,3,4-tetrahydronaphthalen-2-yl)isoindole-1,3-dione

Scheme 3. To a stirred suspension of 60% NaH (6 g; 0.182 mmol) in DMF (400 mL) is added 6-methoxy-1,2,3,4-tetrahydronaphthalen-2-ylamine (30 g; 0.140 mol), portionwise at 0° C. The reaction mixture is warmed to RT and stirred for an additional 1 h. Phthalic anhydride (20.7 g; 0.139 mol) is added in 1-portion at RT, upon which the reaction mixture is stirred for an additional 1 h followed by 18 h at 120° C. The reaction was allowed to cool to RT, diluted with $H_2O$ and extracted several times with EtOAc. The combined organic extracts are washed with water, brine, dried over $Na_2SO_4$, and the solvent removed under reduced pressure. The crude solid was triturated with MeOH, filtered, and dried under vacuo to afford 29.1 g (67%) of 2-(6-methoxy-1,2,3,4-tetrahydronaphthalen-2-yl)isoindole-1,3-dione as an off-white solid.

$^1$H NMR (300 MHz, $CDCl_3$): δ 7.83-7.86 (m, 2 H), 7.70-7.73 (m, 2H), 6.96-6.99 (d, 1H), 6.67-6.72 (m, 2H), 4.50-4.59 (m, 1H), 3.78 (s, 3H), 3.52-3.61 (m, 1 H), 2.95-2.98 (m, 2H), 2.81-2.88 (m, 1 H), 2.65-2.76 (m,1 H), 1.97-2.01 (m, 1H) LC/MS: $C_{19}H_{17}NO_3$: m/z 308 (M+1)

C. 2-(6-Hydroxy-1,2,3,4-tetrahydronaphthalen-2-yl)isoindole-1,3,dione

Scheme 3. To 2-(6-methoxy-1,2,3,4-tetrahydronaphthalen-2-yl)isoindole-1,3-dione (29 g; 94.3 mmol) dissolved in anhydrous $CH_2Cl_2$ (500 mL), cooled to −60° C., is added a 1.0 M solution of boron tribromide-$CH_2Cl_2$ (471 mL), dropwise to maintain reaction temperature between −50 to −60° C. Upon completion of the addition, the reaction mixture is allowed to warm to RT and stirred for an additional 4 h. The reaction is cooled to 0° C., quenched with saturated $NaHCO_3$ (400 mL) and stirred for an additional 0.5 h at RT. The precipitate is filtered, washed thoroughly with $H_2O$, suspended in ether, filtered and dried under vacuo to afford 25.4 g (92%) of 2-(6-hydroxy-1,2,3,4-tetrahydronaphthalen-2-yl)isoindole-1,3-dione as an off-white solid.

$^1$H NMR (300 MHz, DMSO-$d_6$): δ 9.11 (bs, 1H), 7.82-7.89 (m, 4 H), 6.84-6.87 (d, 1H), 6.52-6.56 (m, 2H), 4.29-4.37 (m, 1H), 3.45 (bs, 1H), 3.25-3.34 (m, 1 H), 2.73-2.84 (m, 3H), 2.37-2.47 (m, 1H), 1.94-1.98 (m, 1H) LC/MS: $C_{18}H_{15}NO_3$: m/z 294 (M+1)

D. Dimethyl-thiocarbamic acid-O-[6-(1,3-dioxo-1,3-dihydro-isoindol-2-yl)-5,6,7,8-tetrahydro naphthalen-2-yl] ester Scheme 3. To 2-(6-hydroxy-1,2,3,4-tetrahydronaphthalen-2-yl)isoindole-1,3-dione (25.4 g; 86.5 mmol) dissolved in anhydrous DMF (200 mL) is added 1,4-diazabicyclo [2.2.2]octane (48.5 g; 4.32 mol) followed by dimethylaminothio-carbamoyl chloride (53.4 g; 4.32 mol) and the solution was stirred at RT for 4 h. The reaction is poured over ice-water (1 L) and stirred for 18 h. The precipitate was filtered, washed with $H_2O$ and dried under vacuo. The crude solid was purified by flash chromatography ($SiO_2$) eluting with a hexanes-EtOAc gradient to afford 30 g (91%) of dimethylthiocarbamic acid -O-[6-(1,3-dioxo-1,3,-dihydroisoindol-2-yl)-5,6,7,8-tetrahydronaphthalen-2-yl] ester as a white solid.

$^1$H NMR (300 MHz, $CDCl_3$): δ 7.83-7.86 (m, 2 H), 7.70-7.73 (m, 2 H), 7.07-7.10 (d, 1H), 6.83-6.86 (m, 2H), 4.54-4.65 (m, 1H), 3.60-3.69 (m, 1H), 3.46 (s, 3H), 3.34 (s, 3H), 2.88-3.09 (m, 3H), 2.64-2.78 (m, 1H), 1.97-2.01 (m, 1 H) LC/MS: $C_{21}H_{20}N_2O_3S$: m/z 381 (M+1)

E. Dimethylthiocarbamic acid S-[6-(1,3-dioxo-1,3-dihydroisoindol-2-yl)-5,6,7,8-tetrahydronaphthalen-2-yl] ester Scheme 3. To a 50 mL round-bottom flask equipped with a reflux condenser and stir bar, preheated to 330° C. in a sand-bath, is added dimethyl-thiocarbamic acid O-[6-(1,3-dioxo-1,3-dihydroisoindol-2-yl)-5,6,7,8-tetrahydronaphthalen-2-yl] ester (5.32 g; 13.9 mmol) in 1-portion. The melt is stirred for 7-8 min. at 330° C., then rapidly cooled to RT with a $N_2$ stream. The crude residue is purified by flash chromatography ($SiO_2$) eluting with a hexanes-EtOAc gradient to provide 3.1 g (58%) of dimethylthiocarbamic acid S-[6-(1,3-dioxo-1,3-dihydroisoindol-2-yl)-5,6,7,8-tetrahydronaphthalen-2-yl] ester as a white solid.

$^1$H NMR (300 MHz, $CDCl_3$): δ 7.82-7.86 (m, 2H), 7.72-7.75 (m, 2 H), 7.23-7.26 (m, 2H), 7.07-7.10 (d, 1H), 4.524.63 (m, 1H), 3.61-3.70 (m, 1H), 2.89-3.09 (m, 9H), 2.61-2.75 (m, 1H), 1.97-2.04 (m, 1H) LC/MS: $C_{21}H_{20}N_2O_3S$: m/z 381 (M+1)

F. Dimethylthiocarbamic acid S-[6-amino-5,6,7,8-tetrahydronaphthalen-2-yl) ester Scheme 3. A 3-neck flask, equipped with a reflux condensor and mechanical stirrer, is charged with EtOH (115 mL) and dimethylthiocarbamic acid S-[6-(1,3-dioxo-1,3-dihydroisoindol-2-yl)-5,6,7,8-tetrahydronaphthalen-2-yl] ester (8.7 g; 23.5 mmol). Hydrazine (6.6 mL; 2.11 mol) is added in 1-portion at RT and the reaction was refluxed with mechanical stirring for 40 min. The reaction is cooled to RT and the gelatinous, white solid is filtered and washed thoroughly with ether. The ether washes are combined, evaporated under reduced pressure and the crude residue was further triturated with ether, filtered and the ether evaporated under reduced pressure to afford 6.1 g (100%) of dimethylthiocarbamic acid S-[6-amino-5,6,7,8-tetrahydronaphthalen-2-yl) ester as a yellow oil.

LC/MS: $C_{13}H_{18}N_2OS$: m/z 251 (M+1)

G. 2-(6-Amino-5,6,7,8-tetrahydronaphthalen-2-yl-sulfanyl)-2-methylpropionic acid tert-butyl ester Scheme 3. To dimethylthiocarbamic acid S-[6-amino-5, 6,7,8-tetrahydronaphthalen-2-yl) ester (6.1 g; 24.4 mmol), dissolved in MeOH (25 mL) is added a solution of KOH (4.1 g; 73.2 mmol) in MeOH (25 mL) at RT. The solution is stirred at reflux for 5 h and cooled to RT. tert-Butyl 2-bromoisobutyrate (16.3 g; 73.2 mmol) is added to the solution and stirred for 16 h at RT. $NaBH_4$ (9.2 g; 2.44 mol) is added and the reaction is stirred for an additional 48 h at RT. The reaction is quenched with $H_2O$, the solvent evaporated under reduced pressure, and the crude residue partitioned between $H_2O$ and $CH_2Cl_2$. The aqueous phase is extracted with $CH_2Cl_2$ and the combined organic extracts were dried over $Na_2SO_4$, filtered and evaporated under reduced pressure to afford 4.7 g (60%) of 2-(6-amino-5,6,7,8-tetrahydronaphthalen-2-ylsulfanyl)-2-methylpropionic acid tert-butyl ester as a brown oil. LC/MS: $C_{181}H_{27}NO_2S$: m/z 266 (M+1)

H. 2-(6-Acetylamino-5,6,7,8-tetrahydronaphthalen-2-ylsulfanyl)-2-methyl propionic acid tert-butyl ester Scheme 3. To 2-(6-amino-5,6,7,8-tetrahydronaphthalen-2-ylsulfanyl)-2-methylpropionic acid tert-butyl ester (4.7 g; 14.6 mmol), dissolved in $CH_2Cl_2$ (25 mL), is added DIEA (3.3 mL; 18.9 mmol) and the reaction mixture is cooled to 0° C. Acetyl chloride (1.25 mL; 17.5 mmol) is added dropwise at a rate to maintain the temperature between 0-5° C. The reaction was allowed to warm to RT and stirred for 16 h. The reaction was diluted with $CH_2Cl_2$, washed with $H_2O$, dried over $Na_2SO_4$ and evaporated under reduced pressure. The crude oil was purified by flash chromatography ($SiO_2$) eluting with a hexanes-EtOAc gradient to afford 1.7 g (32%) of 2-(6-acetylamino-5,6,7,8-tetrahydronaphthalen-2-ylsulfanyl)-2-methylpropionic acid tert-butyl ester as a tan solid.

$^1$H NMR (300 MHz, $CDCl_3$): δ 7.23-7.26 (m, 2 H), 6.99-7.01 (d, 1 H), 5.46-5.48 (m, 1H), 4.25-4.29 (m, 1H), 3.08-3.15 (dd, 1H), 2.82-2.88 (m, 2H), 2.58-2.66 (m, 1H), 2.01-2.04 (m, 1H), 1.98 (s, 3H), 1.70-1.82 (m, 1H), 1.43 (s, 15H) LC/MS: $C_{20}H_{29}NO_3S$: m/z 308 (M+1)

I. 2-(6-Ethylamino-5,6,7,8-tetrahydronaphthalen-2-ylsulfanyl)-2-methylpropionic acid tert-butyl ester Scheme 3. To a solution of 2-(6-acetylamino-5,6,7,8-tetrahydronaphthalen-2-ylsulfanyl)-2-methylpoprionic acid tert-butyl ester (1.7 g; 4.64 mmol) in THF (42 mL) is added a solution of 1.0 M borane-THF (42 mL), dropwise at RT. The reaction was allowed to stir for 18 h at RT, carefully quenched with MeOH and the solvent was evaporated under reduced pressure. The residual oil was further azeotroped with MeOH (3×) to afford 1.9 g (100%) of a mixture of 2-(6-ethylamino-5,6,7,8-tetrahydronaphthalen-2-ylsulfanyl)-2-methylpropionic acid tert-butyl ester and it's borane complex as an oil.

LC/MS: $C_{20}H_{31}NO_2SBH_3$: m/z 308 ((M+$BH_3$)+1)

J. 2-{6-[1-Ethyl-3-(4-trifluoromethoxyphenyl)ureido]-5,6,7,8-tetrahydronaphthalen-2-ylsulfanyl}-2-methylpropionic acid tert butyl ester Scheme 4. To a mixture of 2-(6-ethylamino-5,6,7,8-tetrahydronaphthalen-2-ylsulfanyl)-2-methylpropionic acid tert-butyl ester and borane complex (1.9 g; 5.2 mmol)

dissolved in CH$_2$Cl$_2$ (15 mL) is added 4-trifluoromethoxyphenyl isocyanate (1.6 g; 7.8 mmol) and the reaction was stirred at RT for 18 h. The solvent was removed under reduced pressure and the crude residue was purified by flash chromatography (SiO$_2$) eluting with a hexanes-EtOAc gradient to provide 1.66 g (58%) of 2-{6-[1-ethyl-3-(4-trifluoromethoxyphenyl)ureido]-5,6,7,8-tetrahydronaphthalen-2-ylsulfanyl}-2-methylpropionic acid tert butyl ester as a white foam.

LC/MS: C$_{28}$H$_{35}$F$_3$N$_2$O$_4$S: m/z 497 ((M−C$_4$H$_8$)+1)

K. 2-{6-[1-Ethyl-3-(4-trifluoromethoxyphenyl)ureido]-5,6,7,8-tetrahydronaphthalen-2-ylsulfanyl}-2-methylpropionic acid Scheme 4. To 2-{6-[1-ethyl-3-(4-trifluoromethoxyphenyl)ureido]-5,6,7,8-tetrahydronaphthalen-2-ylsulfanyl}-2-methylpropionic acid tert butyl ester (1.66 g; 3.0 mmol) dissolved in CH$_2$Cl$_2$ (15 mL) is added TFA (15 mL) and the reaction was stirred at RT for 1.5 h. The solvent was removed under reduced pressure and the residue was purified by flash chromatography (SiO$_2$) eluting with a hexanes-EtOAc gradient to afford 0.643 g (43%) of 2-{6-[1-ethyl-3-(4-trifluoromethoxyphenyl)ureido]-5,6,7,8-tetrahydronaphthalen-2-ylsulfanyl}-2-methylpropionic acid as a white solid.

$^1$H NMR (300 MHz, CD$_3$OD): δ 7.45-7.48 (m, 2H), 7.06-7.24 (m, 5H), 4.44 (m, 1H), 3.43-3.45 (m, 2H), 2.96-3.02 (m, 4H), 2.00-2.05 (m, 2H), 1.41-1.46 (s, 6H), 1.21-1.29 (m,3H) LC/MS: C$_{24}$H$_{27}$F$_3$N$_2$O$_4$S: m/z 497 (M+1)

Route 2

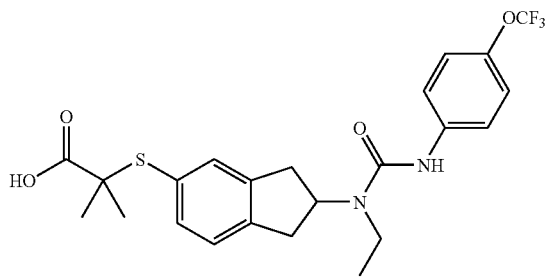

2-{2-[1-Ethyl-3-(4-trifluoromethoxyphenyl)ureido]indan-5-ylsulfanyl}-2-methylpropionic acid Compound 2.0

EXAMPLE 2

A. 5-Methoxyindan-1,2-dione-2-oxime

Scheme 2. To a solution of 5-methoxyindan-1-one (75.8 g; 0.467 mol) in MeOH (1.4 L) at 45° C. is added butyl nitrite (81 mL; 0.693 mol) dropwise over 45 min. Concentrated HCl (45 mL) is then added to the hot solution over 20 min and the reaction was allowed to stir at 45° C. for an additional 1.5-2 h. The reaction suspension is cooled, the precipitate filtered, washed several times with cold MeOH, and dried under vacuo to afford 55.8 g (62%) of 5-methoxyindan-1,2-dione-2-oxime as a beige solid.

$^1$H NMR (300 MHz, CD$_3$OD): δ 7.80-7.83 (m, 1H), 6.95 (bs, 2H), 3.92 (s, 3H), 3.78 (s, 2H), 3.47 (bs,1H) LC/MS: C$_{10}$H$_9$NO$_3$: m/z 192 (M+1)

B. 5-Methoxyindan-2-ylamine hydrochloride

Scheme 2. To 5-methoxyindan-1,2-dione-2-oxime (55.7 g; 0.291 mol), suspended in glacial acetic acid (0.99 L) is added concentrated H$_2$SO$_4$ (67 mL) followed by 10% Pd-C (27 g) and the reaction is mixed on a Parr apparatus under H$_2$ at 60 psi for 18 h. The reaction is purged with N$_2$, filtered through a pad of celite and washed with AcOH. The solvent is removed under reduced pressure to ⅕ volume and the remaining solvent is diluted with H$_2$O (500 mL), cooled to 0° C., and neutralized to pH 10 with 50% aqueous NaOH. The aqueous phase is extracted extensively with CHCl$_3$ several times and the extracts are combined, washed with H$_2$O, brine, dried over Na$_2$SO$_4$, filtered and evaporated under reduced pressure to provide 77.3 g (66%) of a crude oil. The oil was subjected to flash chromatography (SiO$_2$) eluting with 40:2.2:0.2 CHCl$_3$:MeOH:NH$_4$OH to provide 43.8 g (37%) of a dark oil. The oil is dissolved in ether (1 L), cooled to 0° C., and the solution is saturated with HCl (g). The solvent was removed under reduced pressure and the solid triturated with ether, filtered, and washed with ether to provide 43.8 g (30%) of 5-methoxyindan-2-ylamine hydrochloride as a white solid.

$^1$H NMR (300 MHz, CD$_3$OD): δ 7.08-7.11 (d, 1H), 6.77 (s, 1H), 6.69-6.72 (d, 1H), 3.78-3.85 (m, 1H), 3.77 (s, 3H), 3.08-3.19 (m, 2H), 2.57-2.68 (m, 2H), 1.51 (s, 2H) LC/MS: C$_{10}$H$_9$NO$_3$: m/z 192 (M+1) M.P. =240-241° C.

C. 2-(5-Methoxyindan-2-yl)isoindole-1,3-dione

Scheme 3. To a suspension of 60% NaH (8 g; 0.240 mol) in DMF (250 mL), cooled to 0° C., is added 5-methoxyindan-2-ylamine hydrochloride (40.0 g; 0.2 mol) and the suspension stirred for 1 h at RT. Phthalic anhydride (30 g; 0.2 mol) is added in 1-portion and the suspension stirred for an additional 1-1.5 h at RT followed by stirring at 120° C. for 96 h. The reaction is cooled and diluted with EtOAc. The organic phase is washed with H$_2$O, the resultant precipitate filtered, washed with EtOAc, MeOH and dried under vacuo to afford 25.2 g (43%) of 2-(5-methoxyindan-2-yl)isoindole-1,3-dione as a white solid. The organic phase is washed with H$_2$O, evaporated under reduced pressure and the solid is triturated with MeOH, filtered, and dried to afford an additional 19.7 (33%) g of 2-(5-methoxyindan-2-yl)isoindole-1,3-dione as a white solid.

$^1$H NMR (300 MHz, CD$_3$OD): δ 7.83-7.87 (m, 2H), 7.68-7.74 (m, 2H), 7.10-7.13 (d, 1H), 6.73-6.78 (m, 2H), 5.08-5.21 (m, 1H), 3.79 (s, 3H), 3.48-3.65 (m, 2H), 3.07-3.18 (m, 2H) LC/MS: C$_{18}$H$_{15}$NO$_3$: m/z 294 (M+1)

D. 2-(5-Hydroxyindan-2-yl)isoindole-1,3-dione

Scheme 3. To 2-(5-methoxyindan-2-yl)isoindole-1,3-dione (19.7 g; 67 mmol) dissolved in anhydrous CH$_2$Cl$_2$ (350 mL) and cooled to −60° C., is added a 1.0 M solution of boron tribromide-CH$_2$Cl$_2$ (340 mL), dropwise at a rate to maintain the internal temperature between −50 and −60° C. The reaction mixture is allowed to warm to RT and stirred for an additional 5 h. The reaction is cooled to 0° C., quenched with saturated NaHCO$_3$ (500 mL) and stirred for an additional 0.5 h at RT. The precipitate is filtered, washed with H$_2$O, suspended in ether, filtered and dried under vacuo to afford 14.8 g (79%) of 2-(5-hydroxyindan-2-yl)isoindole-1,3-dione as a beige solid.

$^1$H NMR (300 MHz, DMSO-d$_6$): δ 9.16 (s, 1H), 7.82-7.91 (m, 4 H), 6.98-7.01 (d, 1H), 6.56-6.62 (m, 2H), 4.91-5.03 (m, 1H), 3.27-3.43 (m, 3H), 2.99-3.10 (m, 2H) LC/MS: C$_{17}$H$_{13}$NO$_3$: m/z 280 (M+1)

F. Dimethylthiocarbamic acid O-[2-(1,3-dioxo-1,3-dihydroisoindol-2-yl)indan-5-yl] ester Scheme 3. To 2-(5-hydroxyindan-2-yl)isoindole-1,3-dione (31 g; 0.11 mol) dissolved in anhydrous DMF (400 mL) is added 1,4-diazabicyclo[2.2.2]-octane (62 g; 0.55 mol) followed by dimethylaminothiocarbamoyl chloride (68 g; 0.55 mol) and the solution was stirred at RT for 16 h. The reaction is poured over ice-water (1 L) and stirred for 18 h. The precipitate was filtered, washed with $H_2O$ and dried under vacuo to afford 41.6 g (100%) of dimethylthiocarbamic acid O-[2-(1,3-dioxo-1,3-dihydroisoindol-2-yl)indan-5-yl] ester as a beige solid.
$^1$H NMR (300 MHz, $CDCl_3$): δ 7.82-7.87 (m, 2 H), 7.69-7.75 (m, 2 H), 7.17-7.24 (d, 1H), 6.87-6.93 (m, 2H), 5.13-5.25 (m, 1H), 3.53-3.68 (m, 2H), 3.46 (s, 3H), 3.34 (s, 3H), 3.09-3.23 (m, 2H)

G. Dimethylthiocarbamic acid S-[2-(1,3-dioxo-1,3-dihydroisoindol-2-yl)indan-5-yl] ester Scheme 3. To a 50 mL round-bottom flask, equipped with a reflux condenser and stir bar, preheated to 330° C. in a sand-bath is added dimethylthiocarbamic acid O-[2-(1,3-dioxo-1,3-dihydroisoindol-2-yl)indan-5-yl]ester (6.30g; 18.7 mmol) in 1-portion. The melt is stirred for 12 min. at 338° C., rapidly cooled to RT with a $N_2$ stream and the crude residue purified by flash chromatography ($SiO_2$) eluting with a hexanes-EtOAc gradient to afford 3.88 g (61%) of dimethylthiocarbamic acid S-[2-(1,3-dioxo-1,3-dihydroisoindol-2-yl)indan-5-yl] ester as an off-white solid.
$^1$H NMR (300 MHz, $CDCl_3$): δ 7.81-7.87 (m, 2H), 7.69-7.74 (m, 2 H), 7.22-7.36 (m, 3H), 5.10-5.22 (m, 1H), 3.59-3.67 (m, 2H), 3.06-3.23 (m, 9H) LC/MS: $C_{20}H_{18}N_2O_3S$: m/z 367 (M+1)

H. Dimethylthiocarbamic acid S-(2-aminoindan-5-yl) ester

Scheme 3. A 3-neck flask, equipped with a reflux condensor and mechanical stirrer, is charged with EtOH (98 mL) and dimethylthiocarbamic acid S-[2-(1,3-dioxo-1,3-dihydroisoindol-2-yl)indan-5-yl] ester (6.9 g; 20.6 mmol). Hydrazine (5.8 mL; 186 mmol) is added in 1-portion at RT and the reaction was refluxed with mechanical stirring for 30 min. The reaction is cooled to RT and the gelatinous, white solid is filtered and washed with ether several times. The ether washes are combined, evaporated under reduced pressure and the crude residue was further triturated with ether, filtered and the ether evaporated under reduced pressure to afford 4.6 g (95%) of dimethylthiocarbamic acid S-[2-aminoindan-5-yl) ester as a brown oil.
$^1$H NMR (300 MHz, $CDCl_3$): δ 7.15-7.33 (m, 3H), 3.80-3.88 (m, 1 H), 3.05-3.22 (m, 8H), 2.64-2.72 (m, 1H), 2.17 (bs, 2H) LC/MS: $C_{12}H_{16}N_2OS$: m/z 237 (M+1)

I. 2-(2-Aminoindan-5-ylsulfanyl)-2-methylpronionic acid tert-butyl ester

Scheme 3. To dimethylthiocarbamic acid S-(2-aminoindan-5-yl) ester (4.9 g; 20.9 mmol), dissolved in MeOH (60 mL) is added a solution of KOH (11.8 g; 10 0.210 mol) in MeOH (110 mL) at RT. The solution is stirred at reflux for 5 h and cooled to RT. tert-Butyl 2-bromoisobutyrate (7.0 g; 31.3 mmol) is added to the solution and stirred for 18 h at RT. The solvent is evaporated under reduced pressure and the crude residue partitioned between $H_2O$ and EtOAc. The aqueous phase is extracted with EtOAc and the combined organic extracts were washed with $H_2O$, brine, dried over $Na_2SO_4$, filtered and evaporated under reduced pressure to afford 4.9 g (76%) of 2-(2-aminoindan-5-ylsulfanyl)-2-methylpropionic acid tert-butyl ester as a brown oil.
LC/MS: $C_{17}H_{25}NO_2S$: m/z 308 (M+1)

J. 2-(2-Acetylaminoindan-5-visulfanyl)-2-methylpropionic acid tert-butyl ester Scheme 3. To 2-(2-aminoindan-5-ylsulfanyl)-2-methylpropionic acid tert-butyl ester (14.6 g; 47.4 mmol), dissolved in $CH_2Cl_2$ (100 mL), is added TEA (8.6 mL; 61.7 mmol) and the reaction mixture is cooled to 0° C. Acetyl chloride (4.1 mL; 57.6 mmol) is added dropwise at a rate to maintain the temperature between 0-5° C. The reaction was allowed to warm to RT, stirred for 16 h, diluted with $CH_2Cl_2$, washed with $H_2O$, dried over $Na_2SO_4$ and evaporated under reduced pressure. The crude oil was purified by flash chromatography ($SiO_2$) eluting with a hexanes-EtOAc gradient to afford 11.7 g (71%) of 2-(2-acetylaminoindan-5-ylsulfanyl)-2-methylpropionic acid tert-butyl ester as a beige solid.
$^1$H NMR (300 MHz, $CDCl_3$): δ 7.31-7.35 (m, 2 H), 7.15-7.18 (d, 1 H), 5.73 (m,1 H), 4.68-4.78 (m, 1H), 3.25-3.39 (dd, 2H), 2.74-2.80 (d, 2H), 1.94 (s, 3H), 1.43 (s, 15H) LC/MS: $C_{19}H_{27}NO_3S$: m/z 294 (M+1)

K. 2-(2-Ethylaminoindan-5-ylsulfanyl)-2-methylpropionic acid tert-butyl ester Scheme 3. To a solution of 2-(2-acetylaminoindan-5-ylsulfanyl)-2-methylpropionic acid tert-butyl ester (11.7 g; 33.5 mmol) in THF (280 mL) is added a solution of 1.0 M borane-THF (226 mL), dropwise at RT. The reaction was allowed to stir for 5 h at RT, cooled to 0° C., quenched with MeOH (100 mL) and evaporated under reduced pressure. The residual oil was further azeotroped with MeOH (3×) to afford 11 g (100%) of a mixture of 2-(2-ethylaminoindan-5-ylsulfanyl)-2-methylpropionic acid tert-butyl ester and its borane complex as an oil.
LC/MS: $C_{19}H_{29}NO_2SBH_3$: m/z 336 ((M+$BH_3$)+1)

K. 2-[2-[1-Ethyl-3-(4-trifluoromethoxyphenyl)ureido]indan-5-ylsulfanyl]-2-methldpropionic acid tert butyl ester Scheme 4. To a mixture of 2-(2-ethylaminoindan-5-ylsulfanyl)-2-methylpropionic acid tert-butyl ester and borane complex (11.0 g; 33 mmol), dissolved in $CH_2Cl_2$ (100 mL), is added 4-trifluoromethoxyphenyl isocyanate (10.2 g; 50.2 mmol) and the reaction was allowed to stir at RT for 18 h. The solvent was removed under reduced pressure and the crude residue was purified by flash chromatography ($SiO_2$) eluting with a hexanes-EtOAc gradient to afford 11.2 g (62%) of 2-{2-[1-ethyl-3-(4-trifluoromethoxyphenyl)ureido]indan-5-ylsulfanyl}-2-methylpropionic acid tert butyl ester as a white foam.
$^1$H NMR (300 MHz, $CDCl_3$): δ 7.30-7.36 (m, 4H), 7.10-7.19 (m, 3H), 6.31 (s, 1 H), 4.97-5.08 (m, 1 H), 3.22-3.39 (m, 4H), 3.01-3.09 (dd, 2H), 1.42-1.44 (m, 15H), 1.23-1.28 (t, 3H) LC/MS: $C_{27}H_{33}F_3N_2O_4S$: m/z 483 ((M−$C_4H_8$)+1)

M. 2-[2-[1-Ethyl-3-(4-trifluoromethoxyphenyl)ureido]indan-5-ylsulfanyl]-2-methylpropionic acid Scheme 4. To 2-{2-[1-ethyl-3-(4-trifluoromethoxyphenyl)ureido]indan-5-ylsulfanyl}-2-methylpropionic acid tert butyl ester (4.8 g; 8.91 mmol) dissolved in $CH_2Cl_2$ (15 mL) is added TFA (15 mL) and the reaction was stirred at RT for 2 h. The solvent was removed under reduced pressure and the residue was purified by flash chromatography ($SiO_2$) eluting with a hexanes-EtOAc gradient to afford 3.13 g (73%) of 2-{2-[1-ethyl-3-(4-trifluoromethoxyphenyl)ure-ido]indan-5-ylsulfanyl}-2-methylpropionic acid as a white solid.

$^1$H NMR (300 MHz, CDCl$_3$): δ 7.29-7.35 (m, 4H), 7.15-7.17 (d, 1H), 7.08-7.11 (d, 2H), 6.45 (s, 1H), 4.94-5.04 (m, 1H), 3.18-3.36 (m, 4H), 2.98-3.07 (m, 2H), 1.48 (s, 6H), 1.19-1.28 (t, 3H) LC/MS: C$_{23}$H$_{25}$F$_3$N$_2$O$_4$S: m/z 483 (M+1) M.P. =73-77° C.

The following 14 compounds were prepared following Schemes 3 and 4 and Steps J, K, L and M of Route 2, substituting reagents and adjusting reaction conditions as needed:

(R)-2-{2-[1-Ethyl-3-(4-trifluoromethoxyphenyl)ureido]indan-5-ylsulfanyl}-2-methylpropionic acid Compound 2.1

EXAMPLE 3

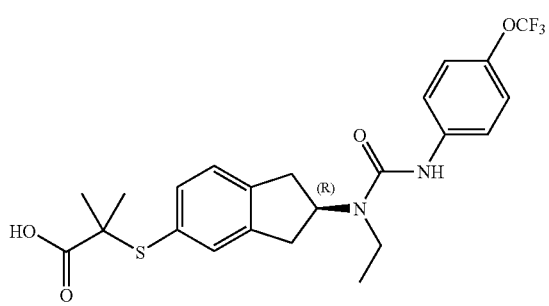

Intermediate L (11 g) of Route 2 was resolved by chiral chromatography (Chiralpak AD column 50 cm×160 mm; isocratic solvent system of hexane/methanol/ethanol: 92/4/4 at 80 mL/min, monitored at 220 nm). (R)-Intermediate L (4.8 g) came off the column first and provided Compound 2.1 (3.1 g) using Step M of Route 2. (S)-Intermediate L (4.2 g) provided the corresponding (S) final product (2.3 g).
LC/MS: C$_{23}$H$_{25}$F$_3$N$_2$O$_4$S: m/z 483 (M+1)

2-{2-[1-Ethyl-3-(4-trifluoromethylsulfanylphenyl)ureido]indan-5-ylsulfanyl}-2-methylpropionic acid Compound 2.2

EXAMPLE 4

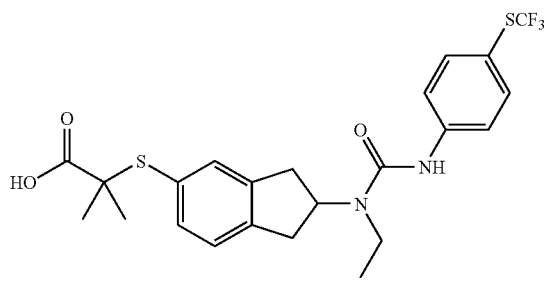

Compound 2.2 (0.33 g; 57% for 2 steps; white solid) was prepared following Route 2 by replacing 4-trifluoromethoxyphenyl isocyanate with 4-trifluorothiomethoxy isocyanate.

$^1$H NMR (CD$_3$OD); δ 1.16-1.20 (t, 3H), 1.38 (s, 6H), 3.09-3.23 (m, 4H), 3.37-3.44 (q, 2H), 4.95-5.06 (m, 1H), 7.14-7.17 (m, 1H), 7.32-7.35 (m, 1H), 7.40 (s, 1H), 7.55 (s, 4H) LC/MS: C$_{23}$H$_{25}$F$_3$N$_2$O$_3$S$_2$: m/z 499 (M+1)

2-Methyl-2-{2-[1-pentyl-3-(4-trifluoromethylsulfanylphenyl)ureido]indan-5-ylsulfanyl}propionic acid Compound 2.3

EXAMPLE 5

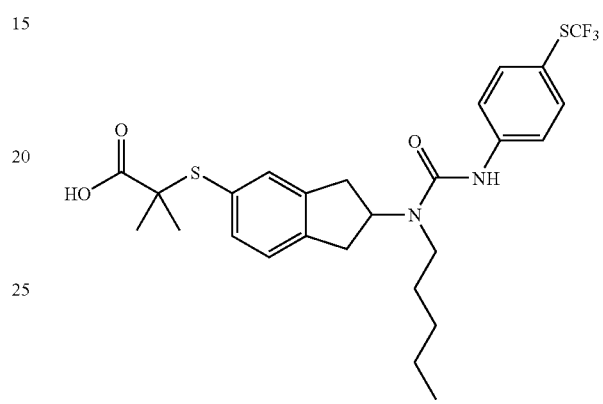

Compound 2.3 (0.22 g; 32% for 2 steps; white solid) was prepared following Route 2 and Compound 2.2 by replacing acetyl chloride with valeryl chloride.

$^1$H NMR (CD$_3$OD); δ 0.844-0.890 (t, 3H), 1.20-1.31 (m, 4H), 1.39 (s, 6H), 1.45-1.58 (m, 2H), 3.07-3.22 (m, 6H), 4.89-4.99 (m, 1H), 7.15-7.18 (m, 1H), 7.33-7.35 (m, 2H), 7.33-7.35 (m,1H), 7.40 (s,1H), 7.50-7.57 (m, 4H) LC/MS: C$_{26}$H$_{31}$F$_3$N$_2$O$_3$S$_2$: m/z 541 (M+1)

2-{2-[1-Ethyl-3-(4isopropyl phenyl)ureido]indan-5-ylsulfanyl}-2-methylpropionic acid Compound 2.4

EXAMPLE 6

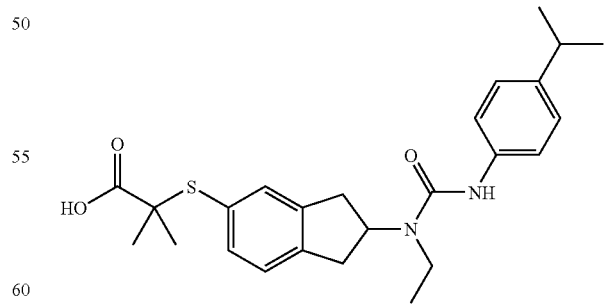

Compound 2.4 (0.18 g; 34% for 2 steps; white solid) was prepared following Route 2 by replacing 4-trifluoromethoxyphenyl isocyanate with 4-isopropylphenyl isocyanate.

$^1$H NMR (CD$_3$OD); δ 1.16-1.23 (m, 9H), 1.38 (s, 6H), 2.82-2.87 (m, 1H), 3.10-3.21 (m, 4H), 3.37-3.39 (m, 2H), 4.99-5.04 (m, 1H), 7.14-7.17 (m, 3H), 7.23-7.26 (m, 2H), 7.32-7.50 (m, 2H), 7.40 (s,1H) LC/MS: $C_{25}H_{32}N_2O_3S$: m/z 441 (M+1)

2-{2-[3-(4-Dimethylaminophenyl)-1-ethylureido]indan-5-ylsulfanyl}-2-methylpropionic acid Compound 2.5

EXAMPLE 7

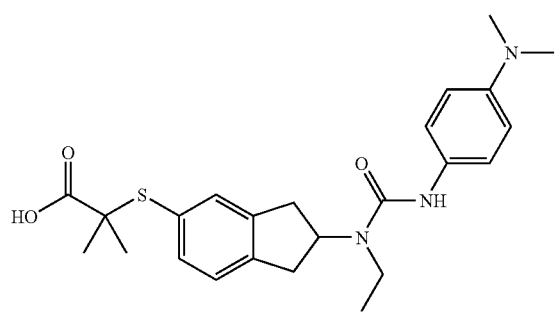

Compound 2.5 (0.34 g; 66% for 2 steps; white solid) was prepared following Route 2 by replacing 4-trifluoromethoxyphenyl isocyanate with 4-dimethylaminophenyl isocyanate.

$^1$H NMR (CD$_3$OD); δ 1.15-1.20 (t, 3H), 1.42 (s, 6H), 2.88 (s, 1H), 3.05-3.69 (m, 4H), 3.31-3.69 (m, 2H), 4.94-5.06 (m, 1H), 6.78-6.81 (m, 2H), 7.16-7.21 (m, 3H), 7.29-7.41 (m, 2H) LC/MS: $C_{24}H_{31}N_3O_3S$: m/z 442 (M+1)

2-Methyl-2-{2-[1-pentyl-3-(4-trifluoromethoxyphenyl)ureido]indan-5-ylsulfanyl}-2-methylpropionic acid Compound 2.6

EXAMPLE 8

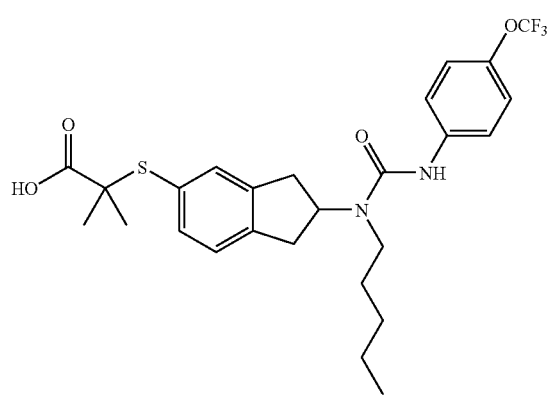

Compound 2.6 (0.29 g; 77% for 2 steps; white solid) was prepared following Route 2 by replacing acetyl chloride with valeryl chloride.

$^1$H NMR (CD$_3$OD); δ 0.847-0.893 (t, 3H), 1.20-1.29 (m, 4H), 1.39 (s, 6H), 1.58-1.60 (m, 2H), 3.04-3.29 (m, 6H), 4.89-4.99 (m, 1H), 7.14-7.17 (m, 3H), 7.32-7.34 (m, 1H), 7.40-7.45 (m, 3H) LC/MS: $C_{26}H_{31}F_3N_2O_4S$: m/z 525 (M+1)

2-{2-[3-(4-Dimethylaminophenyl)-1-pentylureido]indan-5-ylsulfanyl}-2-methylpropionic acid Compound 2.7

EXAMPLE 9

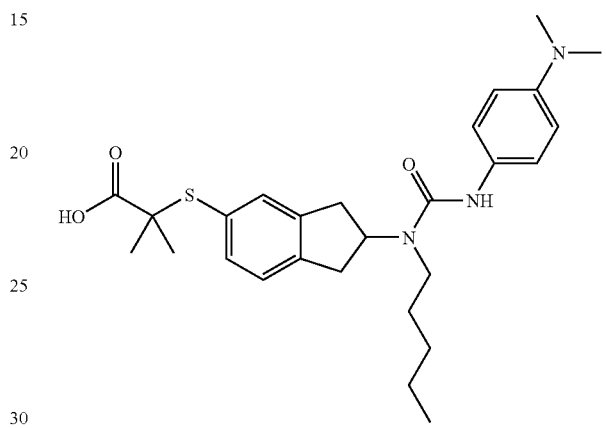

Compound 2.7 (0.25 g; 36% for 2 steps; white solid) was prepared following Route 2 and compound 2.5 by replacing acetyl chloride with valeryl chloride.

$^1$H NMR (CD$_3$OD); δ 0.869-0.915 (t, 3H), 1.17-1.31 (m, 4H), 1.44 (s, 6H), 1.57-1.65 (m, 2H), 2.91 (s, 6H), 3.12-3.29 (m, 6H), 4.94-5.02 (m, 1H), 6.80-6.83 (d, 2H), 7.17-7.23 (m, 3H), 7.32-7.38 (m, 2H) LC/MS: $C_{27}H_{37}N_3O_3S$: m/z 484 (M+1)

2-{2-[3-(4-Isopropylphenyl)-1-(pentyl)ureido]indan-5-ylsulfanyl}-2-methylpropionic acid Compound 2.8

EXAMPLE 10

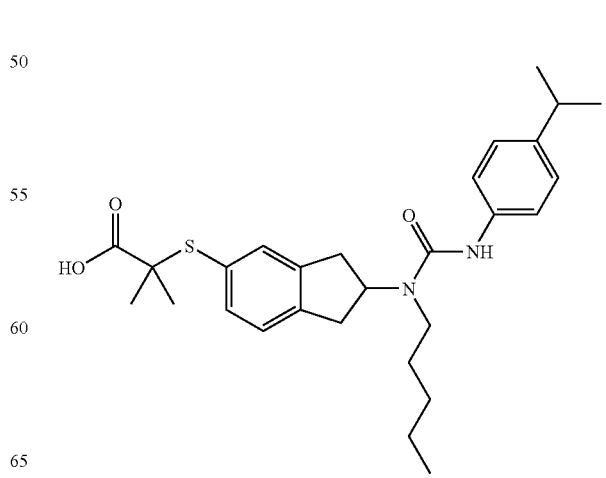

Compound 2.8 (5 mg; 14% for 2 steps; white solid) was prepared following Route 2 and compound 2.4 by replacing acetyl chloride with valeryl chloride.

LC/MS: $C_{28}H_{38}N_2O_3S$: m/z 483 (M+1)

2-{2-[3-(4-tert-butylphenyl)-1-(pentyl)ureido]indan-5-ylsulfanyl}-2-methylpropionic acid Compound 2.9

EXAMPLE 11

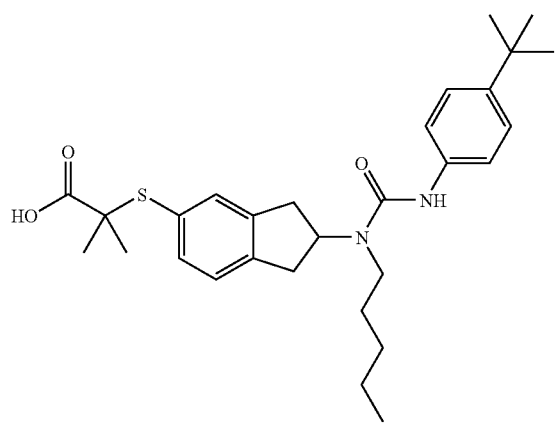

Compound 2.9 (4 mg; 9% for 2 steps; white solid) was prepared following Route 2 and compound 2.3 by replacing 4-trifluorothiophenyl isocyanate with 4-tert-butylphenyl isocyanate.

LC/MS: $C_{29}H_{40}N_2O_3S$: m/z 497 (M+1)

2-[2-(3-Biphenyl-4-yl-1-pentylureido)indan-5-ylsulfanyl]-2-methylpropionic acid

Compound 2.10

EXAMPLE 12

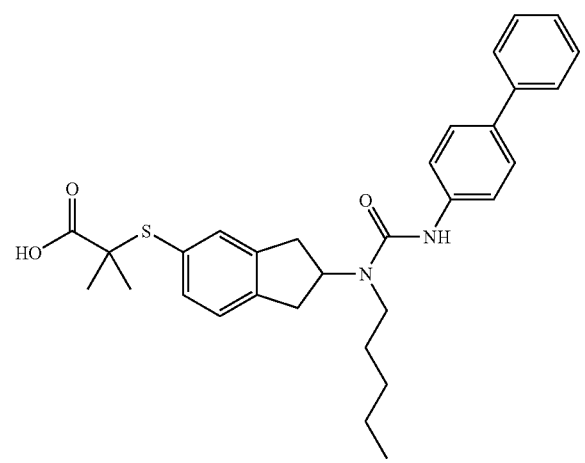

Compound 2.10 (3 mg; 7% for 2 steps; white solid) was prepared following Route 2 and compound 2.3 by replacing 4-trifluorothiophenyl isocyanate with 4-biphenylyl isocyanate.

LC/MS: $C_{31}H_{36}N_2O_3S$: m/z 517 (M+1)

2-{2-[3-(4-Isopropylphenyl)-1-(hexyl)ureido]indan-5-ylsulfanyl}-2-methylpropionic acid Compound 2.11

EXAMPLE 13

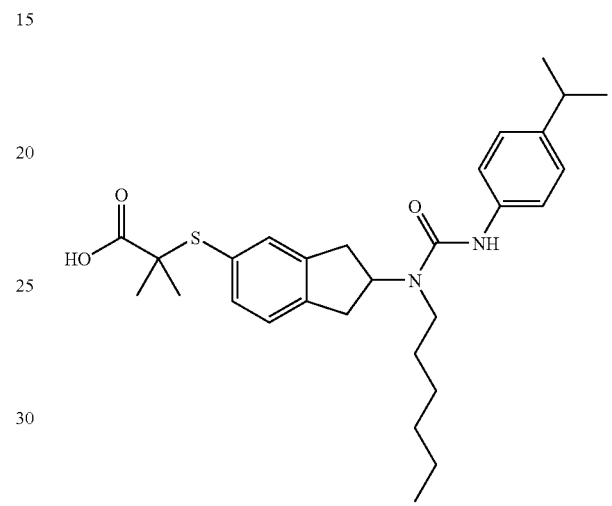

Compound 2.11 (13 mg; 44% for 2 steps; oil) was prepared following Route 2 and Compound 2.4 by replacing valeryl chloride with caproyl chloride.

LC/MS: $C_{29}H_{40}N_2O_3S$: m/z 497 (M+1)

2-Methyl-2-{2-[1-hexyl-3-(4-trifluoromethoxyphenyl)ureido]indan-5-ylsulfanyl}propionic acid Compound 2.12

EXAMPLE 14

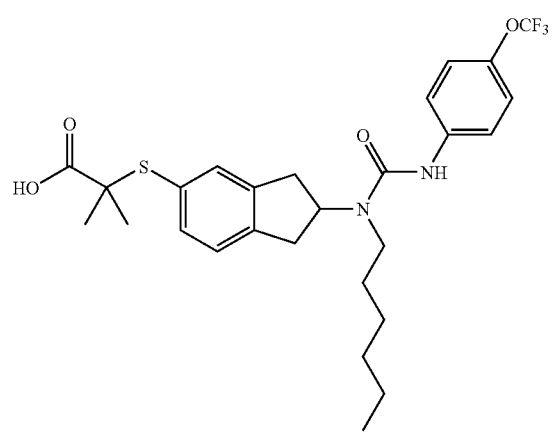

Compound 2.12 (18 mg; 54% for 2 steps; white solid) was prepared following Route 2 by replacing valeryl chloride with caproyl chloride.

LC/MS: $C_{27}H_{33}F_3N_2O_4S$: m/z 539 (M+1)

2-Methyl-2-{2-[1-hexyl-3-(4-trifluoromethylsulfanylphenyl)ureido]indan-5-ylsulfanyl}propionic acid Compound 2.13

EXAMPLE 15

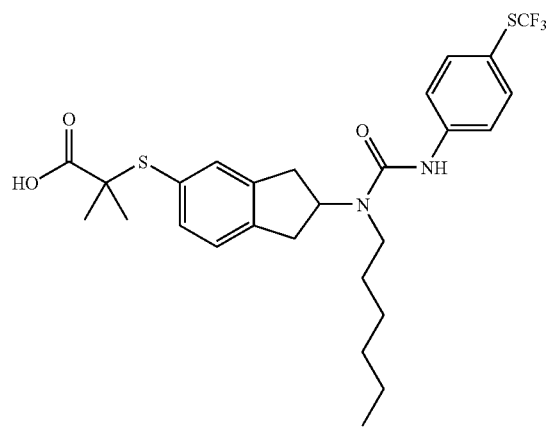

Compound 2.13 (14 mg; 36% for 2 steps; white solid) was prepared following Route 2 and Compound 2.2 by replacing valeryl chloride with caproyl chloride.

LC/MS: $C_{27}H_{33}F_3N_2O_3S_2$: m/z 555 (M+1)

2-Methyl-2-{2-[1-propyl-3-(4-trifluoromethoxyphenyl)ureido]indan-5-ylsulfanyl}propionic acid Compound 2.14

EXAMPLE 16

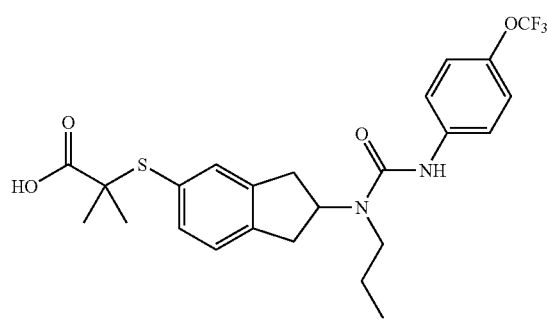

Compound 2.14 (1.2 mg; 3% for 2 steps; oil) was prepared following Route 2 by replacing acetyl chloride with propionyl chloride.

LC/MS: $C_{24}H_{27}F_3N_2O_4S$: m/z 497 (M+1)

2-Methyl-2-{2-[1-butyl-3-(4-trifluoromethylsulfanylphenyl)ureido]indan-5-ylsulfanyl}propionic acid Compound 2.15

EXAMPLE 17

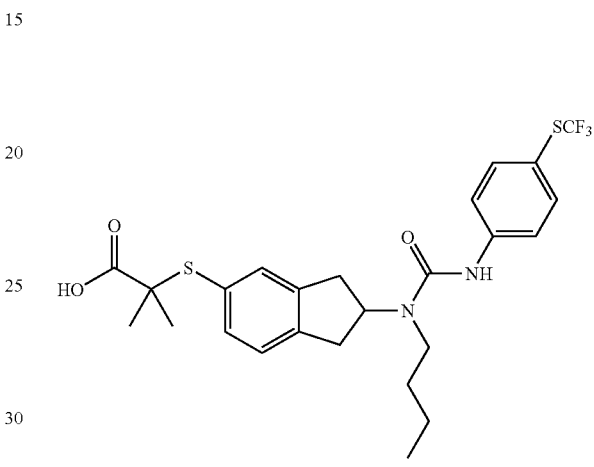

Compound 2.15 (11 mg; 32% for 2 steps; oil) was prepared following Route 2 and Compound 2.2 by replacing acetyl chloride with butyryl chloride.

LC/MS: $C_{25}H_{29}F_3N_2O_3S_2$: m/z 527 (M+1)

2-Methyl-2-{2-[3-(4-trifluoromethoxyphenyl)ureido]indan-5-ylsulfanyl}propionic acid Compound 2.16

EXAMPLE 18

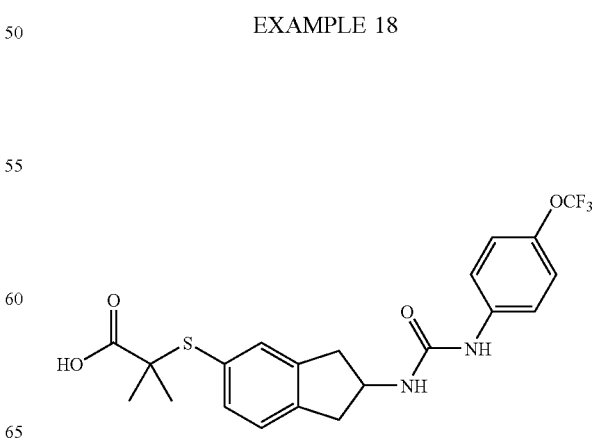

Compound 2.16 (11 mg; 49% for 2 steps; oil) was prepared following Route 2 by acylating with 4-trifluoromethoxyphenyl isocyanate.

LC/MS: $C_{21}H_{21}F_3N_2O_4S$: m/z 455 (M+1)

Route 3

2-Methy-2-{2-[1-pent-4-enyl-3-(4-trifluoromethoxyphenyl)ureido]indan-5-ylsulfanyl}propionic acid Compound 3.0

EXAMPLE 19

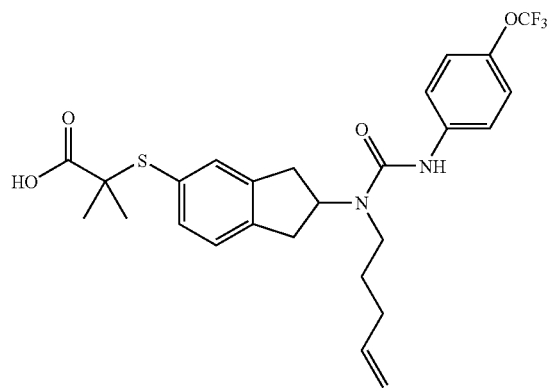

To 2-(2-aminoindan-5-ylsulfanyl)-2-methylpropionic acid tert-butyl ester (0.220 g; 0.72 mmol), dissolved in DCE (4 mL), is added pent-4-enal (0.060 mg; 0.72 mmol) followed by sodium triacetoxyborohydride (0.21 g; 1.0 mmol) and the reaction mixture stirred for 18 h at RT. The reaction mixture was diluted with $CH_2Cl_2$, washed with $H_2O$, brine, dried over $Na_2SO_4$, filtered and the solvent evaporated under reduced pressure to afford 2-methyl-2-(2-pent-4-enylaminoindan-5-ylsulfanyl)propionic acid tert-butyl ester as a crude oil.

Compound 3.0 (0.149 mg; 40% for 3 steps; white solid) was prepared following Route 2 and steps L and M by acylating with 4-trifluoromethoxyphenyl isocyanate.

LC/MS: $C_{26}H_{29}F_3N_2O_4S$: m/z 522 (M+1)

The following 2 compounds were prepared following Schemes 3 and 4, Route 3, Steps L and M of Route 2, substituting reagents and adjusting reaction conditions as needed:

2-Methyl-2-{2-[1-(3-methylbutyl)-3-(4-trifluoromethoxyphenyl)ureido]indan-5-ylsulfanyl}-2-methylpropionic acid Compound 3.1

EXAMPLE 20

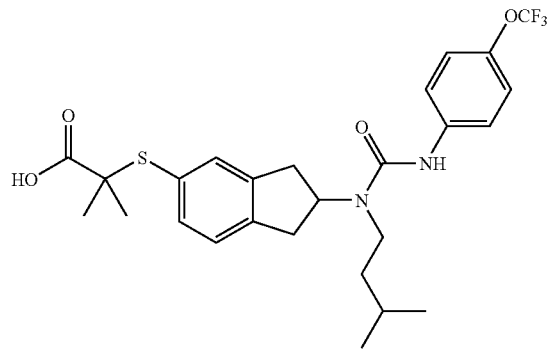

Compound 3.1 (13 mg; 29% for 3 steps; white solid) was prepared following Route 3 substituting pent-4-enal with isobutyraldehyde and acylating with 4-trifluoromethoxyphenyl isocyanate.

LC/MS: $C_{26}H_{31}F_3N_2O_4S$: m/z 525 (M+1)

2-{2-[3-(4-Isopropylphenyl)-1-(3-methylbutyl)ureido]indan-5-ylsulfanyl}-2-methylpropionic acid Compound 3.2

EXAMPLE 21

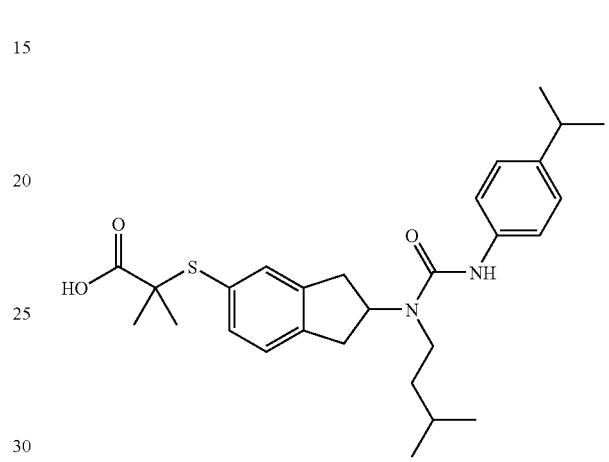

Compound 3.2 (11 mg; 27% for 3 steps; white solid) was prepared following Route 3 and compound 3.1 by replacing 4-trifluoromethoxyphenyl isocyanate with 4-isopropylphenyl isocyanate.

$^1$H NMR (CD$_3$OD); δ 0.877-0.895 (dd, 6H), 1.19-1.22 (dd, 6H), 1.42-1.53 (m, 9H), 2.80-2.89 (m, 1H), 2.99-3.08 (m, 2H), 3.17-3.48 (m, 4H), 4.98-5.03 (m, 1H), 6.26 (s, 1H), 7.10-7.22 (m, 5H), 7.32-7.35 (m, 2H) LC/MS: $C_{28}H_{38}N_2O_3S$: m/z 483 (M+1)

The following 3 compounds were prepared following Schemes 1 and 3 and Steps J and K of Route 1, substituting reagents and adjusting reaction conditions as needed:

2-{6-[1-Butyl-3-(4-trifluoromethoxyphenyl)ureido]-5,6,7,8-tetrahydronaphthalen-2-ylsulfanyl}-2-methylpropionic acid Compound 1.1

EXAMPLE 22

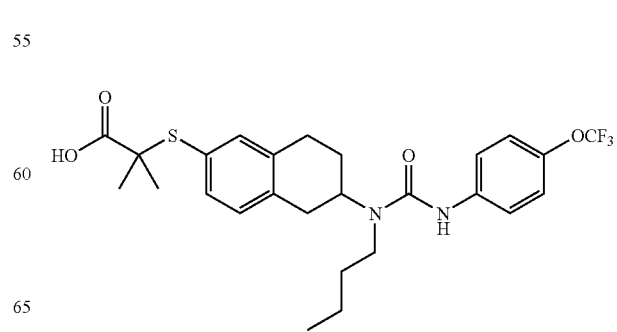

Compound 1.1 (41 mg; 68% for 2 steps; white solid) was prepared following Route 1 by replacing acetyl chloride with butyryl chloride.

LC/MS: $C_{26}H_{31}F_3N_2O_4S$: m/z 525 (M+1)

2-{6-[1-Butyl-3-(4-trifluoromethylsulfanylphenyl)ureido]-5,6,7,8-tetrahydronaphthalen-2-ylsulfanyl}-2-methylpropionic acid Compound 1.2

EXAMPLE 23

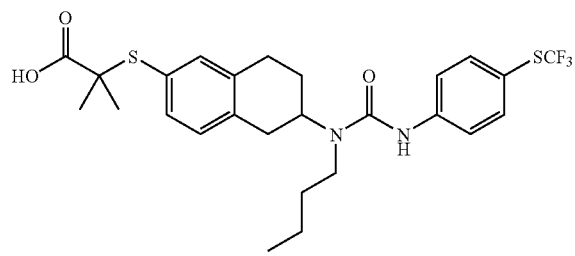

Compound 1.2 (23 mg; 34% for 2 steps; white solid) was prepared following Route 1 and compound 1.1 by replacing acetyl chloride with butyryl chloride and 4-trifluoromethoxyphenyl isocyanate with 4-trifluorothiophenyl isocyanate.

LC/MS: $C_{26}H_{31}F_3N_2O_3S_2$: m/z 541 (M+1)

2-{6-[1-Hexyl-3-(4-trifluoromethoxyphenyl)ureido]-5,6,7,8-tetrahydronaphthalen-2-ylsulfanyl}-2-methylpropionic acid Compound 1.3

EXAMPLE 24

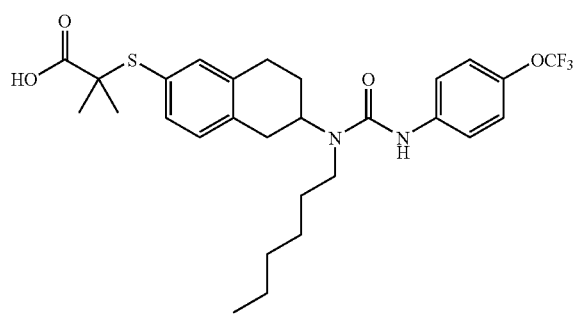

Compound 1.3 (36 mg; 57% for 2 steps; white solid) was prepared following Route 1 by replacing acetyl chloride with caproyl chloride.

LC/MS: $C_{28}H_{35}F_3N_2O_4S$: m/z 553 (M+1)

The following 2 compounds were prepared following Schemes 3 and 4 and Steps L and M of Route 2, substituting reagents and adjusting reaction conditions as needed:

2-{2-[3-(3-Bromo-4-trifluoromethoxyphenyl)-1-ethylureido]indan-5-ylsulfanyl}-2-methylpropionic acid Compound 2.17

EXAMPLE 25

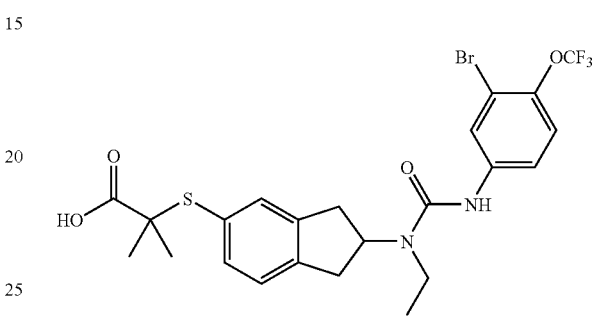

Compound 2.17 (0.018 g; 19% for 3 steps; white solid) was prepared following Route 2 by replacing 4-trifluoromethoxy phenyl isocyanate with 3-bromo4-trifluoromethoxyphenyl isocyanate. To 3-bromo-4-trifluoromethoxy aniline (0.214 g; 0.836 mmol) in THF (1 mL) is added di-tert-butyl dicarbonate (0.255 g; 1.17 mmol) followed by 4-dimethylaminopyridine (0.102 g; 0.835 mmol). After the effervesence ceases (30 min.), a solution of 2-(2-ethylaminoindan-5-ylsulfanyl)-2-methylpropionic acid tert-butyl ester (0.058 g; 0.167 mmol) in THF (1 mL) is added and the reaction mixture stirred for 18 h at RT. Using Steps K and L of Route 2, the titled compound was prepared.

LC/MS: $C_{23}H_{24}BrF_3N_2O_4S$: m/z 563 (M+1)

2-{2-[1-Ethyl-3-(3-trifluoromethoxyphenyl)ureido]indan-5-ylsulfanyl}-2-methylpropionic acid Compound 2.18

EXAMPLE 26

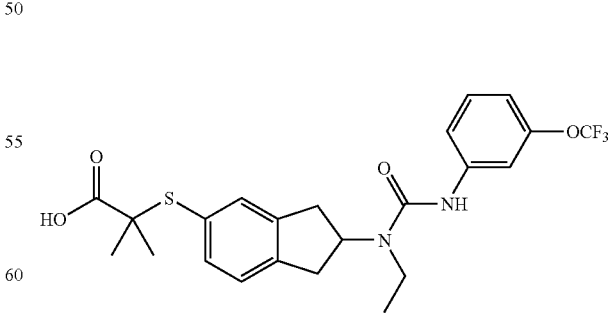

Compound 2.18 (13 mg; 12% for 3 steps; white solid) was prepared following Example 2.0 by replacing 4-trifluoromethoxyphenyl isocyanate with 3-trifluoromethoxyphenyl isocyanate. To a solution of carbonyldiimidazole (0.454 g;

2.8 mmol) in THF (2 mL), heated to 50° C., is added 3-trifluoromethoxyaniline (0.522 g; 2.94 mmol), dropwise. After 15 min. the reaction is cooled and added to a solution of 2-(2-ethylaminoindan-5-ylsulfanyl)-2-methylpropionic acid tert-butyl ester (0.077 g; 0.22 mmol) in THF (1 mL).

LC/MS: $C_{23}H_{25}F_3N_2O_4S$: m/z 483 (M+1)

2-{2-[3-(4-Dimethylaminophenyl)-1-methylureido] indan-5-ylsulfanyl}-2-methylpropionic acid Compound 2.19

EXAMPLE 27

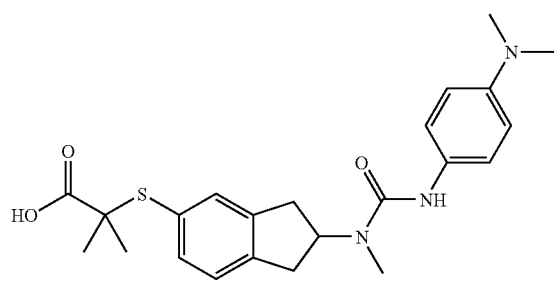

A. Dimethylthiocarbamic acid S-(2-formylamino-indan-5-yl)ester

Scheme 6. To dimethylthiocarbamic acid-S-[2-aminoindan-5-yl] ester (2.0 g; 8.46 mmol) in $CHCl_3$ (10 mL) is added ethyl formate (50 mL) and the reaction heated at 55° C. for 24 h. The reaction is cooled, the solvent removed under reduced pressure, and the crude oil purified by flash chromatography ($SiO_2$) eluting with an ethyl acetate-methanol gradient to afford 0.77 g (35%) of dimethylthiocarbamic acid-S-(2-formylaminoindan-5-yl)ester as a white solid.

LC/MS: $C_{13}H_{16}N_2O_2$: m/z 264 (M+1)

B. 2-Methyl-2-(2-methylaminoindan-5-ylsulfanyl)-propionic acid tert-butyl ester

Scheme 6. To dimethylthiocarbamic acid S-(2-formylaminoindan-5-yl)ester (0.772 g; 2.9 mmol) in THF (9 mL) under $N_2$ is added a solution of 1.0 M lithium aluminum hydride (9 mL) at 0° C. The reaction is warmed to RT then stirred at reflux for 24 h. The reaction is cooled to 0° C., quenched with $H_2O$, and the solvent removed under reduced pressure. The residue is dissolved in MeOH (4 mL), to which is added $Cs_2CO_3$ (0.304 g; 0.93 mmol), tert-butyl 2-bromoisobutyrate (0.311 mL; 1.39 mmol), and $NaBH_4$ (2.0 g; 52.8 mmol). The reaction mixture is stirred for 18 h, the removed under reduced pressure and the residue partitioned between EtOAc and $H_2O$. The layers are separated, the aqueous phase extracted with EtOAc, the organic extracts combined, washed with brine, dried over $Na_2SO_4$, filtered and evaporated under reduced pressure. The crude residue is purified by flash chromatography ($SiO_2$) eluting with a $CH_2Cl_2$-MeOH gradient to afford 0.186 g (20%) of 2-methyl-2-(2-methylaminoindan-5-ylsulfanyl)propionic acid tert-butyl ester as an oil.

LC/MS: $C_{18}H_{27}NO_2S$: m/z 321 (M+1)

Compound 2.19 (44 mg; 65% for 2 steps; white solid) was prepared following Route 2 and Steps L and M by replacing 4-trifluoromethoxyphenyl isocyanate with 4-dimethylaminophenyl isocyanate.

LC/MS: $C_{23}H_{29}N_3O_3S$: m/z 428 (M+1)

2-{2-[1-(3-Cyclopentylpropyl)-3-(4-trifluoromethoxyphenyl)ureido]indan-5-ylsulfanyl}-2-methylpropionic acid Compound 2.20

EXAMPLE 28

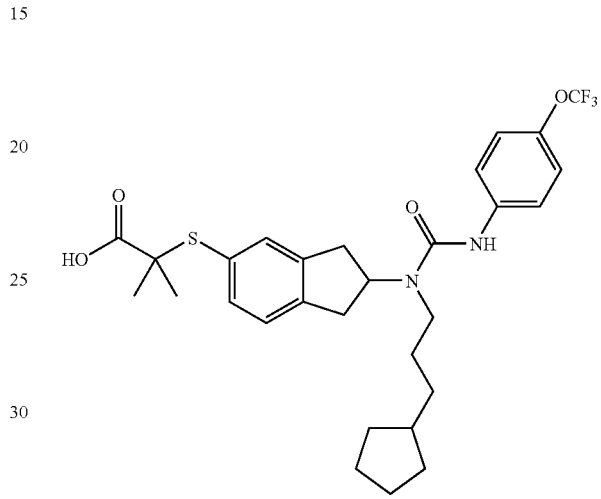

Compound 2.20 (39 mg; 49% for 2 steps; white solid) was prepared following Route 2 by replacing acetyl chloride with 3-cyclopentylpropionyl chloride.

LC/MS: $C_{29}H_{35}F_3N_2O_4S$: m/z 565 (M+1)

2-[2-(3-Indan-5-yl-1-pentyl ureido)indan-5-ylsulfanyl}-2-methylpropionic acid

Compound 2.21

EXAMPLE 29

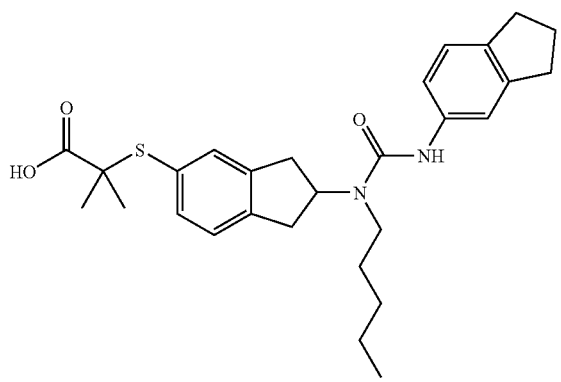

Compound 2.21 (9.3 mg; 24% for 2 steps; white solid) was prepared following Route 2 and Compound 2.3 by replacing acetyl chloride with valeryl chloride and 4-trifluoromethoxyphenyl isocyanate with indanyl isocyanate.

LC/MS: $C_{28}H_{36}N_2O_3S$: m/z 481 (M+1)

2-Methyl-2-{2-[3-(4-methyl-3-nitrophenyl)-1-pentylureido]indan-5-ylsulfanyl} propionic acid Compound 2.22

EXAMPLE 30

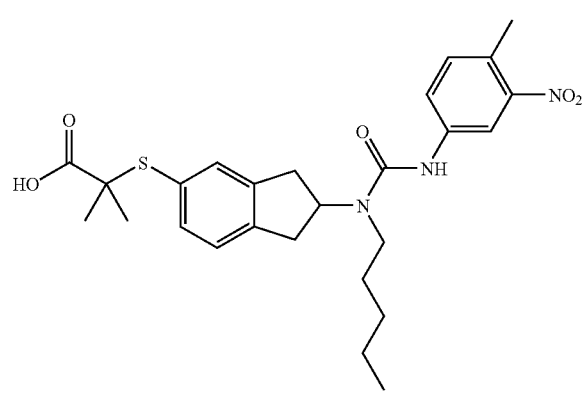

Compound 2.22 (5.0 mg; 12% for 2 steps; white solid) was prepared following Route 2 and compound 2.3 by replacing 4-trifluoromethoxyphenyl isocyanate with 4-methyl-3-nitrophenyl isocyanate.

LC/MS: $C_{26}H_{33}N_3O_5S$: m/z 500 (M+1)

2-Methyl-2-{2-[1-naphthalen-1ylmethyl-3-(4-trilfuoromethoxyphenyl)-ureido]indan-5-ylsulfanyl}-propionic acid Compound 3.4

EXAMPLE 31

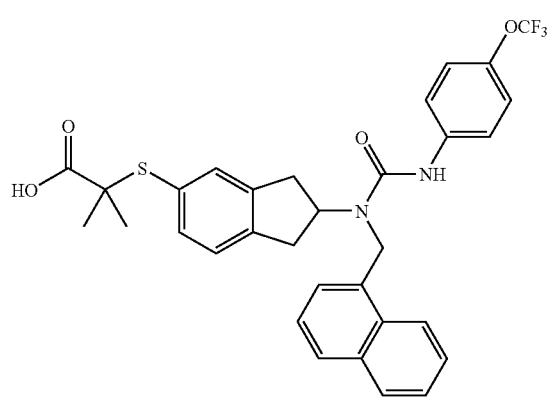

Compound 3.4 (2.9 mg; 4% for 2 steps; white solid) was prepared following Route 3 by replacing pent-4-enal with 1-naphthaldehyde.

LC/MS: $C_{32}H_{29}F_3N_2O_4S$: m/z 595 (M+1)

2-{2-[3-(4-Methoxyphenyl)-1-propylureido]indan-5-ylsulfanyl}-2-methylpropionic acid Compound 2.23

EXAMPLE 32

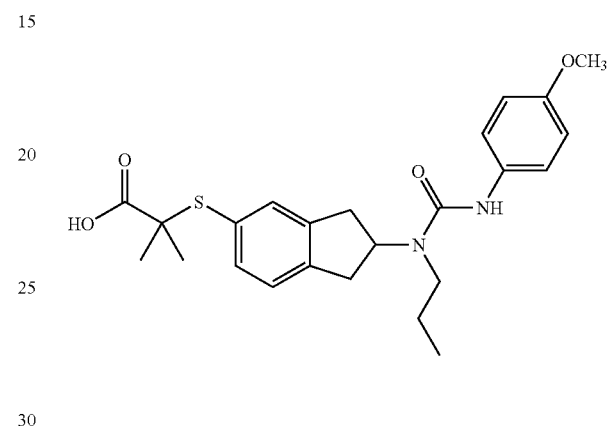

Compound 2.23 (21 mg; 64% for 2 steps; white solid) was prepared following Route 2 and Compound 2.14 by replacing 4-trifluoromethoxyphenyl isocyanate with 4-methoxyphenyl isocyanate.

LC/MS: $C_{24}H_{27}F_3N_2O_4S$: m/z 443 (M+1)

2-{2-[3-(3,5-Dimethylphenyl)-1-propylureido]indan-5-ylsulfanyl}-2-methylpropionic acid Compound 2.24

EXAMPLE 33

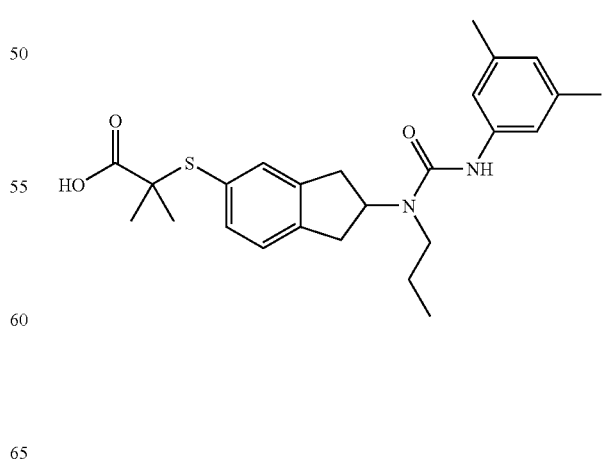

Compound 2.24 (19 mg; 57% for 2 steps; white solid) was prepared following Route 2 and Compound 2.14 by replacing 4-trifluoromethoxyphenyl isocyanate with 3,5-dimethylphenyl isocyanate.

LC/MS: $C_{25}H_{32}N_2O_3S$: m/z441 (M+1)

2-{2-[1-(2-Methoxyethyl)-3-(4-trifluoromethylsulfanylphenyl)ureido]indan-5-ylsulfanyl}-2-methylpropionic acid Compound 2.25

EXAMPLE 34

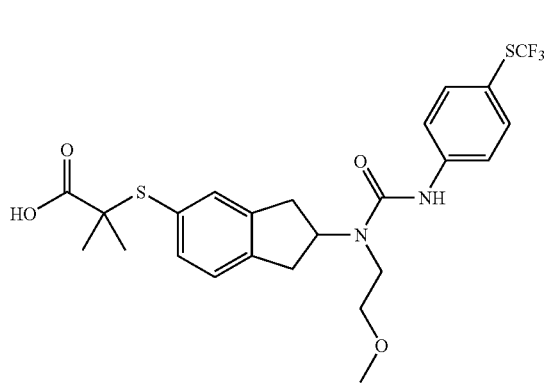

Compound 2.25 (7.0 mg; 16% for 2 steps; oil) was prepared following Route 2 and Compound 2.2 by replacing acetyl chloride with methoxyacetyl chloride.

LC/MS: $C_{24}H_{27}F_3N_2O_4S_2$: m/z 529 (M+1)

2-Methyl-2-{2-[1-propyl-3-(4-trifluoromethylphenyl)ureido]indan-5-ylsulfanyl}-propionic acid Compound 2.26

EXAMPLE 35

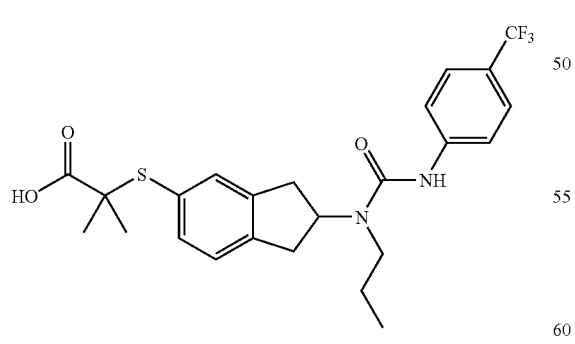

Compound 2.26 (20 mg; 56% for 2 steps; white solid) was prepared following Route 2 and Compound 2.14 by replacing 4-trifluoromethoxyphenyl isocyanate with 4-trifluoromethylphenyl isocyanate.

LC/MS: $C_{24}H_{27}F_3N_2O_3S_2$: m/z481 (M+1)

2-Methyl-2-{2-[1-(4,4,4-trifluorobutyl)-3-(4-trifluoromethoxyphenyl)ureido]indan-5-ylsulfanyl}propionic acid Compound 2.27

EXAMPLE 36

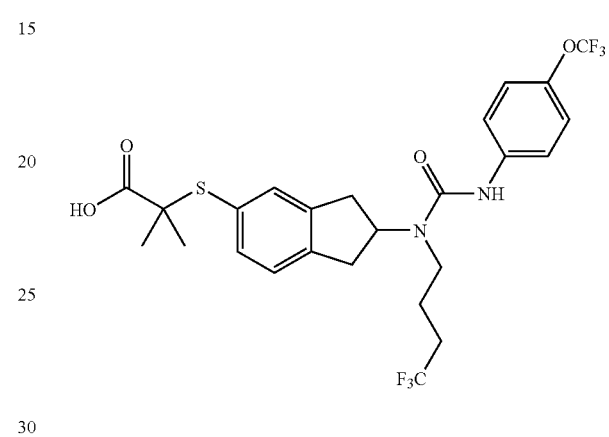

Compound 2.27 (10 mg; 26% for 2 steps; oil) was prepared following Route 2 and Compound 2.0 by replacing acetyl chloride with trifluoromethylbutyryl chloride.

LC/MS: $C_{25}H_{26}F_6N_2O_4S$: m/z 564 (M+1)

2-{2-[1-(3-Cyclopentylpropyl)-3-phenylureido]indan-5-ylsulfanyl}-2-methylpropionic acid Compound 2.28

EXAMPLE 37

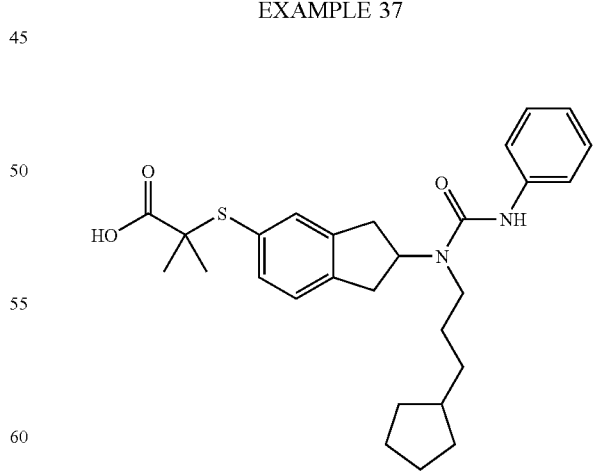

Compound 2.28 (38 mg; 56% for 2 steps; oil) was prepared following Route 2 and Compound 2.0 by replacing acetyl chloride with cyclopentylpropionyl chloride and 4-trifluoromethoxyphenyl isocyanate with phenyl isocyanate.

LC/MS: $C_{28}H_{36}N_2O_3S$: m/z 481 (M+1)

6-[1-[5-(1-Carboxy-1-methylethylsulfanyl)indan-2-yl]-3-(4-isopropylphenyl)-ureido]hexanoic acid methyl ester Compound 2.29

EXAMPLE 38

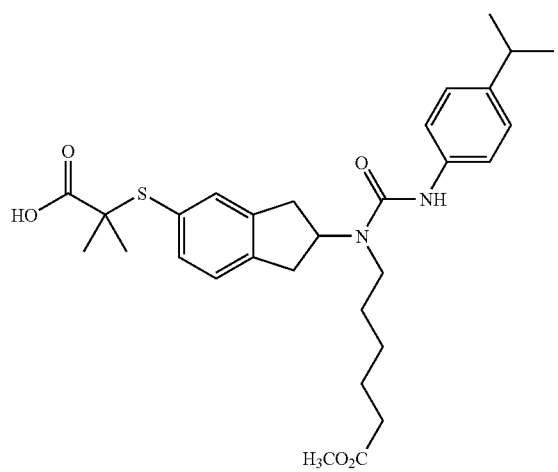

Compound 2.29 (12 mg; 38% for 2 steps; white solid) was prepared following Route 2 and Compound 2.4 by replacing acetyl chloride with 5-chlorocarbonyl-pentanoic acid methyl ester.

LC/MS: $C_{30}H_{40}N_2O_5S$: m/z 541 (M+1)

2-Methyl-2-[2-(3-naphthalen-2-yl-1-pentylureido)indan-5-ylsulfanyl]propionic acid Compound 2.30

EXAMPLE 39

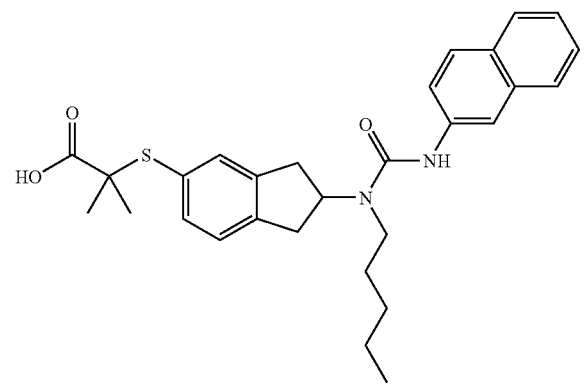

Compound 2.30 (15 mg; 39% for 2 steps; white solid) was prepared following Route 2 and Compound 2.3 by replacing 4-trifluorothiomethoxyphenyl isocyanate with 2-naphthyl isocyanate.

LC/MS: $C_{29}H_{34}N_2O_3S$: m/z 491 (M+1)

2-{2-[1-Cyclohexylmethyl-3-(4-trifluoromethoxyphenyl)ureido]indan-5-ylsulfanyl]-2-methylpropionic acid Compound 2.31

EXAMPLE 40

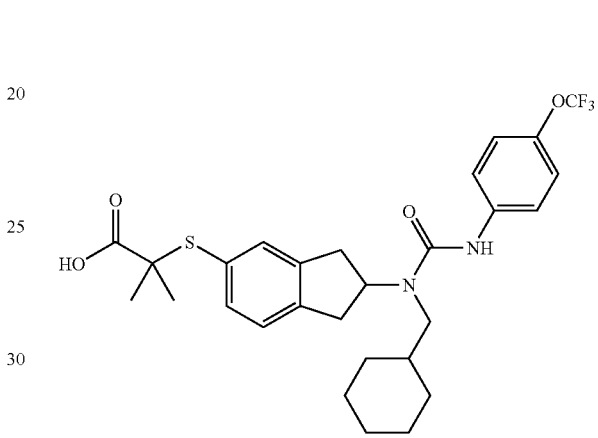

Compound 2.31 (15 mg; 25% for 2 steps; white solid) was prepared following Route 2 and Compound 2.0 by replacing acetyl chloride with cyclohexylacetyl chloride.

LC/MS: $C_{28}H_{33}F_3N_2O_4S$: m/z 551 (M+1)

2-{2-[1-Isobutyl-3-(4-trifluoromethoxyphenyl)ureido]indan-5-ylsulfanyl}-2-methylpropionic acid Compound 3.5

EXAMPLE 41

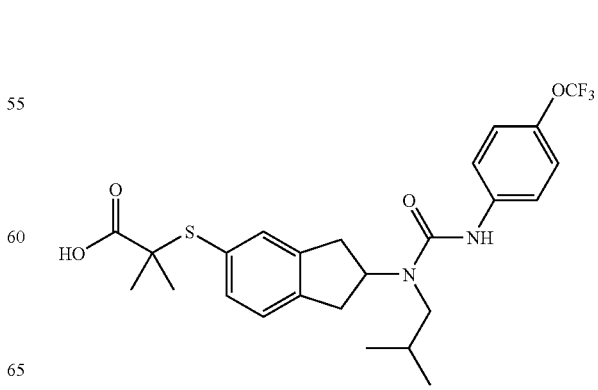

Compound 3.5 (10 mg; 12% for 2 steps; oil) was prepared following Route 3 and Compound 3.0 by replacing pent-5-enal with 2-methylpropionaldehyde.
LC/MS: $C_{25}H_{29}F_3N_2O_4S$: m/z 511 (M+1)

2-{2-[3-(3,4-Dichlorophenyl)-1-heptylureido]indan-5-ylsulfanyl}-2-methylpropionic acid Compound 2.32

EXAMPLE 42

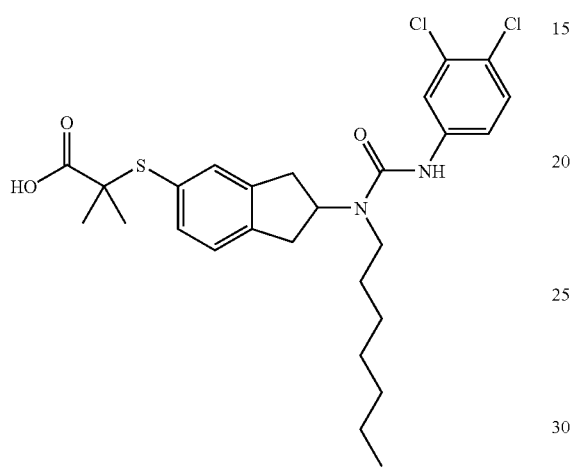

Compound 2.32 (6.7 mg; 12% for 2 steps; oil) was prepared following Route 2 and Compound 2.0 by replacing acetyl chloride with heptanoyl chloride and 4-trifluoromethoxyphenyl isocyanate with 3,4-dichlorophenyl isocyanate.
LC/MS: $C_{27}H_{34}Cl_2N_2O_3S$: m/z 538 (M+1)

2-{2-[1-(2-Dimethylaminoethyl)-3-(4-trifluoromethylsulfanylphenyl)ureido]indan-5-ylsulfanyl}-2-methylpropionic acid Compound 2.33

EXAMPLE 43

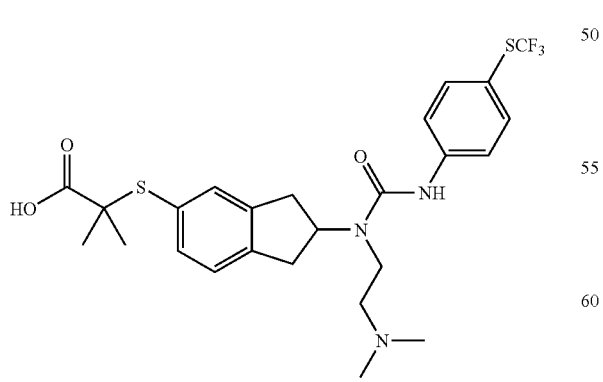

Compound 2.33 (1.9 mg; 4% for 2 steps; oil) was prepared following Route 2 and Compound 2.2 by replacing acetyl chloride with dimethylamino acetyl chloride and 4-trifluoromethoxyphenyl isocyanate with 4-trifluoromethylthiophenyl isocyanate. LC/MS: $C_{25}H_{30}F_3N_3O_3S_2$: m/z 542 (M+1)

2-{2-[3-(3-Chlorophenyl)-1-heptylureido]indan-5-ylsulfanyl}-2-methylpropionic acid Compound 2.34

EXAMPLE 44

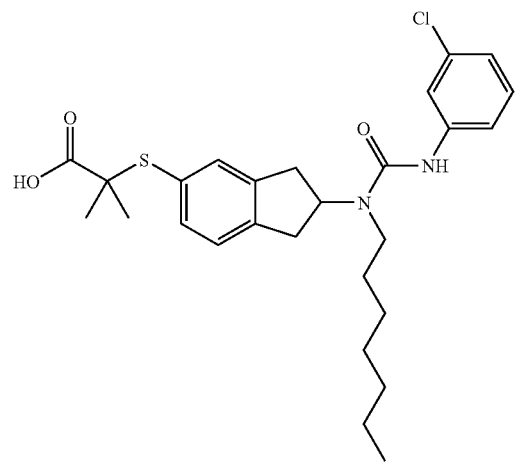

Compound 2.34 (7.4 mg; 14% for 2 steps; white solid) was prepared following Route 2 and Compound 2.32 and 4-trifluoromethoxyphenyl isocyanate with 3-chlorophenyl isocyanate.
LC/MS: $C_{27}H_{35}ClN_2O_3S$: m/z 542 (M+1)

1-{2-[1-Heptyl-3-(4-trifluoromethoxyphenyl)ureido]indan-5-ylsulfanyl}-cyclobutanecarboxylic acid Compound 2.35

EXAMPLE 45

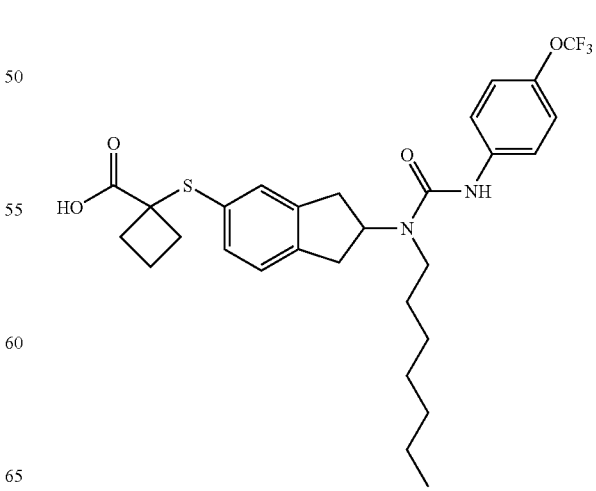

Compound 2.35 (1.0 mg; 1.3% for 2 steps; white solid) was prepared following Route 2 and Compound 2.32 by replacing tert-butyl 2-bromoisobutyrate with ethyl 1-bromocyclobutanecarboxylate.

LC/MS: $C_{29}H_{35}F_3N_2O_4S$: m/z 565 (M+1)

2-Methyl-2-{7-[1-propyl-3-(4-trifluoromethoxyphenyl)ureido]-5,6,7,8-tetrahydronaphthalen-2-ylsulfanyl}propionic acid Compound 1.4

EXAMPLE 46

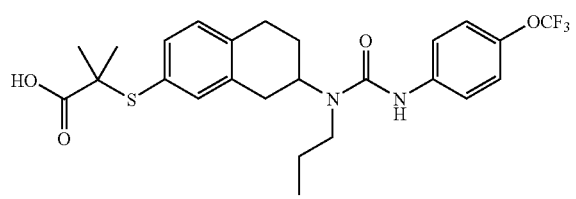

Compound 1.4 (53 mg; 25% for 2 steps; oil) was prepared following Route 1 and Compound 1.0 by replacing acetyl chloride with propionyl chloride.

LC/MS: $C_{25}H_{29}F_3N_2O_4S$: m/z 511 (M+1)

The following two compounds can be prepared following Schemes 10 and 4, Steps I, J and K of Route 1, substituting reagents and adjusting reaction conditions as needed:

2-{6-[1-Ethyl-3-(4-trifluoromethoxyphenyl)ureido]-3-methoxy-5,6,7,8-tetrahydronaphthalen-2-ylsulfanyl}-2-methylpropionic acid Compound 1.5

EXAMPLE 47

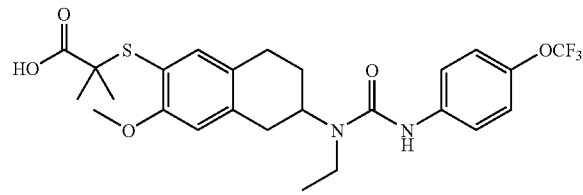

Compound 1.5 (9.8 mg; oil) can be prepared following Route 1, steps I, J, and K and Schemes 4 and 10.

$^1$H NMR (300 MHz, CD$_3$OD): δ 7.45-7.48 (d, 2H), 7.15-7.18 (m, 3H), 6.71 (s, 1H), 4.43-4.79 (m, 1H), 3.75 (s, 3H), 3.43-3.45 (m, 2H), 2.88-3.08 (m, 4H), 1.99-2.03 (m, 2H), 1.38 (s, 6H), 1.25-1.52 (t, 3H) LC/MS: $C_{25}H_{29}F_3N_2O_5S$: m/z 527 (M+1)

Route 4

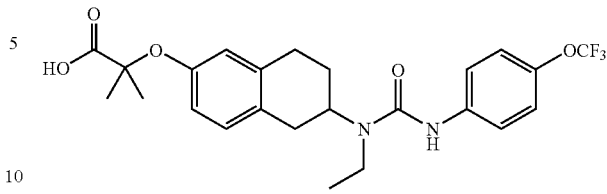

2-{6-[1-Ethyl-3-(4-trifluoromethoxyphenyl)ureido]-5,6,7,8-tetrahydronaphthalen-2-yloxy}-2-methylpropionic acid. Compound 4.0

EXAMPLE 48

A. N-(6-Methoxy-1,2,3,4-tetrahydronaphthalen-2-yl)acetamide

Scheme 7. To a stirred suspension of 6-methoxy-1,2,3,4-tetrahydronaphthalen-2-ylamine (2.54 g; 14.3 mmol) in CH$_2$Cl$_2$ (20 mL) is added DIEA (3.4 mL) and the reaction mixture was cooled to 0° C. Acetyl chloride (1.22 mL; 17.1 mmol) is added dropwise at 0° C. and the reaction is allowed to warm to RT and stirred for 18 h. The reaction mixture was diluted with CH$_2$Cl$_2$, washed with H$_2$O, dried over Na$_2$SO$_4$, filtered and the solvent removed under reduced pressure to provide a crude solid. Purification by flash chromatography (SiO$_2$) eluting with hexanes-EtOAc affords 1.57 g (50%) of N-(6-methoxy-1,2,3,4-tetrahydronaphthalen-2-yl)acetamide as a white solid.

LC/MS: $C_{13}H_{17}NO_2$: m/z 220 (M+1)

B. N-(6-Hydroxy-1,2,3,4-tetrahydronaphthalen-2-yl)acetamide

Scheme 7. To a suspension of N-(6-methoxy-1,2,3,4-tetrahydronaphthalen-2-yl)acetamide (1.57 g; 7.2 mmol) in CH$_2$Cl$_2$ (70 mL), cooled to −60° C., is added a solution of boron tribromide-CH$_2$Cl$_2$ (36 mL), dropwise to maintain the reaction temperature between −50 to −60° C. The gelatinous suspension is allowed to warm to RT and stir for 30 min. The reaction is cooled to 0° C., quenched with satd NaHCO$_3$ and stirred for 30 min at RT. The mixture is extracted with CH$_2$Cl$_2$ (2×), the extracts combined, dried over Na$_2$SO$_4$, filtered and evaporated under reduced pressure to provide a crude solid, which was purified by flash chromatography (SiO$_2$) eluting with a CH$_2$Cl$_2$-MeOH gradient to afford 1.13 g (76%) of N-(6-hydroxy-1,2,3,4-tetrahydronaphthalen-2-yl)acetamide as a beige solid.

LC/MS: $C_{12}H_{15}NO_2$: m/z 206 (M+1)

C. 2-(6-Acetylamino-5,6,7,8-tetrahydronaphthalen-2-yloxy)-2-methylpropionic acid tert-butyl ester Scheme 7. To a suspension of N-(6-hydroxy-1,2,3,4-tetrahydronaphthalen-2-yl)acetamide (0.439 g; 2.1 mmol) in DMF (6 mL) is added Cs$_2$CO$_3$ (1.7 g; 5.2 mmol) and tert-butyl 2-bromoisobutyrate (2.1 mL; 9.4 mmol) and the reaction mixture was stirred at 100° C. for 18 h. The reaction was cooled to RT, diluted with EtOAc, washed with H$_2$O, brine, dried over Na$_2$SO$_4$, filtered, and the solvent removed under reduced pressure to provide a crude oil, which was purified by flash chromatography (SiO$_2$) eluting with a hexanes-EtOAc gradient to afford 0.51 g (69%) of 2-(6-acetylamino-5,6,7,8-tetrahydronaphthalen-2-yloxy)-2-methylpropionic acid tert-butyl ester as an oil.

¹H NMR (300 MHz, CDCl₃): δ 6.89-6.92 (d, 1H), 6.58-6.65 (m, 2H), 5.85-5.88 (m, 1H), 4.24-4.30 (m, 1H), 2.99-3.06 (dd, 1H), 2.76-2.86 (m, 2H), 2.51-2.59 (dd,1H), 2.04 (s, 2H), 1.98-2.02 (m, 1H), 1.74-1.79 (m, 1H), 1.54 (s, 6H), 1.46 (s, 9H) LC/MS: $C_{20}H_{29}NO_4$: m/z 292 (M+1)

The following compound was completed following Schemes 3 and 4 and Steps I, J and K of Route 1, substituting reagents and adjusting reaction conditions as needed:

Compound 4.0 (0.0168 g; 23% for 2 steps; oil) was prepared following Route 1 and Compound 1.0.

LC/MS: $C_{24}H_{27}F_3N_2O_5$: m/z 481 (M+1)

2-{6-[3-(4-tert-Butyl phenyl)1-ethylureido]-3-methoxy-5,6,7,8-tetrahydronaphthalen-2-ylsulfanyl}-2-methyl propionic acid Compound 1.6

EXAMPLE 49

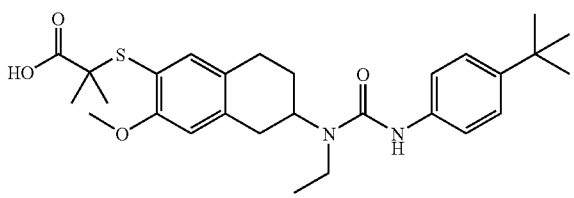

Compound 1.6 (10 mg; oil) can be prepared by replacing 4-trifluoromethoxyphenyl isocyanate with 4-tert-butylphenyl isocyanate and using Route 1, steps I, J, and K and Schemes 4 and 10.

LC/MS: $C_{28}H_{38}N_2O_4S$: m/z 499 (M+1)

2-{6-[1-Ethyl-3-(4-trifluoromethoxyphenyl)ureido]-3-fluoro-5,6,7,8-tetrahydronaphthalen-2-ylsulfanyl}-2-methylpropionic acid Compound 1.7

EXAMPLE 50

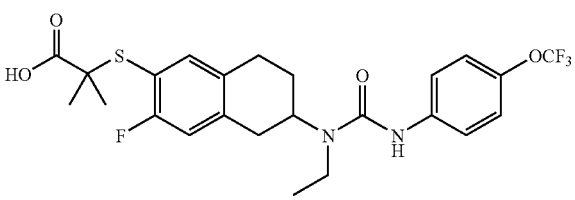

Compound 1.7 (16 mg; 30% after 2 steps; white solid) can be prepared following Route 1, steps I, J, and K and Schemes 4 and 10.

¹H NMR (300 MHz, CDCl₃): δ 7.46-7.51 (m, 2H), 7.25-7.28 (d, 1H), 7.17-7.20 (d, 2H), 6.92-6.95 (d, 1H), 4.43 (m, 1H), 3.42-3.49 (m, 2H), 2.90-3.11 (m, 4H), 2.02-2.07 (m, 2H), 1.45 (s, 6H), 1.25-1.31 (t, 3H) LC/MS: $C_{25}H_{29}F_3N_2O_5S$: m/z 515 (M+1)

2-{6-[1-Ethyl-3-(4-trifluoromethoxyphenyl)ureido]-3-chloro-5,6,7,8-tetrahydronaphthalen-2-ylsulfanyl}-2-methylpropionic acid Compound 1.8

EXAMPLE 51

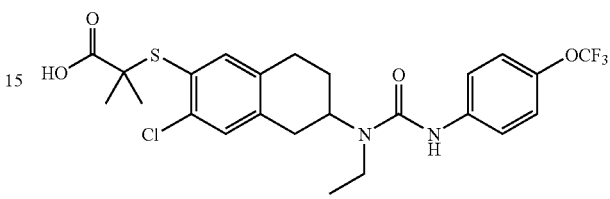

Compound 1.8 (15 mg; 22% after 2 steps; white solid) can be prepared following Route 1, steps I, J, and K and Schemes 4 and 10.

LC/MS: $C_{25}H_{29}F_3N_2O_5S$: m/z 532 (M+1)

2-{6-[1-Ethyl-3-(4-trifluoromethoxyphenyl)ureido]-3-bromo-5,6,7,8-tetrahydronaphthalen-2-ylsulfanyl}-2-methylpropionic acid Compound 1.9

EXAMPLE 52

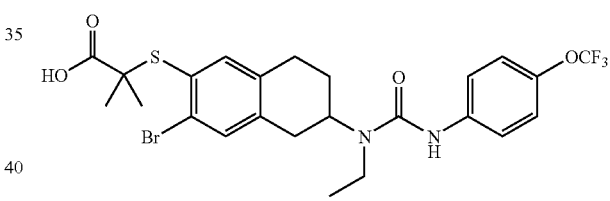

Compound 1.9 (55 mg; 43% for 2 steps; white solid) can be prepared following Route 1, steps I, J, and K and Schemes 4 and 10.

¹H NMR (300 MHz, CDCl₃): δ 7.45-7.48 (m, 3H), 7.36 (s, 1H), 7.15-7.18 (d, 2H), 4.41-4.79 (m,1H), 3.40-3.47 (m, 2H), 2.90-3.07 (m, 4H), 2.01-2.03 (m, 2H), 1.45 (s, 6H), 1.24-1.29 (t, 3H) LC/MS: $C_{25}H_{29}F_3N_2O_5S$: m/z 576 (M+1)

2-{6-[1-Ethyl-3-(4-trifluoromethoxyphenyl)ureido]-3-methyl-5,6,7,8-tetrahydronaphthalen-2-ylsulfanyl}-2-methylpropionic acid Compound 1.10

EXAMPLE 53

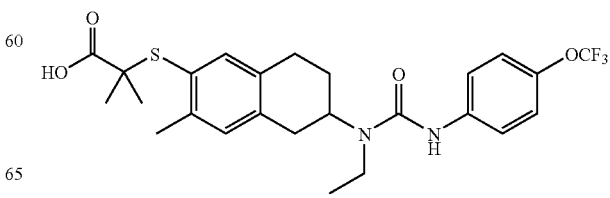

Compound 1.10 (73 mg; 26% for 2 steps; white solid) can be prepared following Route 1, steps I, J, and K and Schemes 4 and 10.

$^1$H NMR (300 MHz, CDCl$_3$): δ 7.45-7.48 (m, 2H), 7.22 (s, 1H), 7.15-7.18 (d, 2H), 7.02 (s, 1H), 4.41-4.79 (m, 1H), 3.40-3.47 (m, 2H), 2.85-3.03 (m, 4H), 2.39 (s, 3H), 2.01-2.03 (m, 2H), 1.41 (s, 6H), 1.24-1.29 (t, 3H) LC/MS: C$_{25}$H$_{29}$F$_3$N$_2$O$_5$S: m/z 511 (M+1)

2-{6-[1-Ethyl-3-(4-trifluoromethoxyphenyl)ureido]-3-trifluoromethoxy-5,6,7,8-tetrahydronaphthalen-2-ylsulfanyl}-2-methylpropionic acid Compound 1.11

EXAMPLE 54

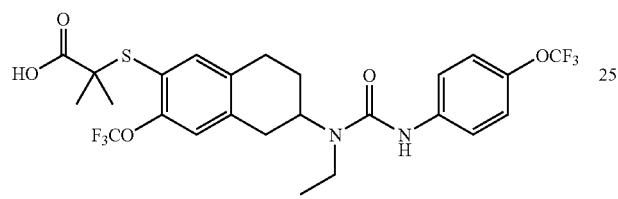

Compound 1.11 (118 mg; 58% for 2 steps; white solid) can be prepared following Route 1, steps I, J, and K and Schemes 4 and 10.

$^1$H NMR (300 MHz, CDCl$_3$): δ 7.45-7.48 (d, 2H), 7.37 (s, 1H), 7.12-7.18 (m, 3H), 4.44 (m, 1H), 3.43-3.48 (m, 2H), 2.97-3.21 (m, 4H), 2.03-2.05 (m, 2H), 1.42 (s, 6H), 1.25-1.30 (t, 3H) LC/MS: C$_{25}$H$_{29}$F$_3$N$_2$O$_5$S: m/z 580 (M+1)

2-{6-[1-Ethyl-3-(4-trifluoromethoxyphenyl)ureido]-3-phenyl-5,6,7,8-tetrahydronaphthalen-2-ylsulfanyl}-2-methylpropionic acid Compound 1.12

EXAMPLE 55

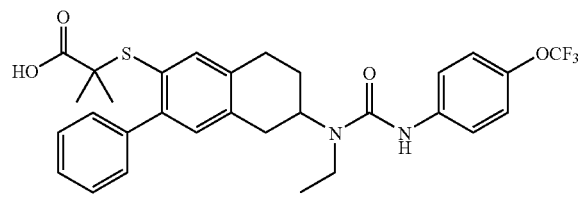

Compound 1.12 (118 mg; 58% for 2 steps; white solid) can be prepared following Route 1, steps I, J, and K and Schemes 4 and 10.

$^1$H NMR (300 MHz, CDCl$_3$): δ 7.45-7.48 (d, 2H), 7.29-7.38 (m, 6H), 7.15-7.18 (d, 2H), 7.10 (s, 1H), 4.46 (m, 1H), 3.44-3.49 (m, 2H), 2.98-3.06 (m, 4H), 2.04-2.06 (m, 2H), 1.26-1.30 (t, 3H), 1.14 (s, 6H) LC/MS: C$_{25}$H$_{29}$F$_3$N$_2$O$_5$S: m/z 573 (M+1)

2-{6-[1-Ethyl-3-(4-hydroxyphenyl)ureido]-5,6,7,8-tetrahydronaphthalen-2-ylsulfanyl}-2-methylpropionic acid

EXAMPLE 56

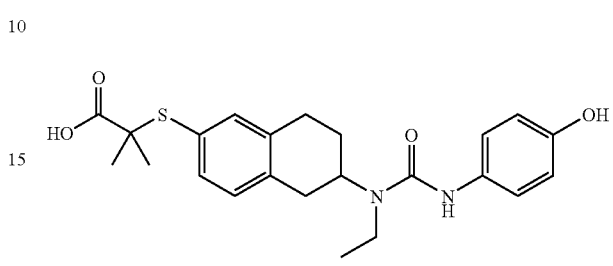

2-{6-[4-Aminophenyl)-1-ethyl ureido]-5,6,7,8-tetrahydronaphthalen-2-ylsulfanyl}-2-methylpropionic acid

EXAMPLE 57

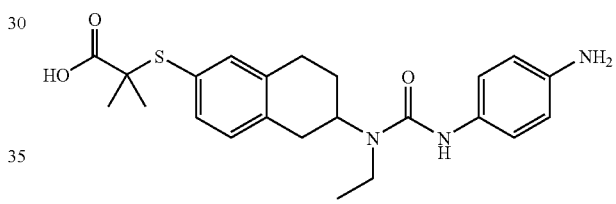

Route 5

2-[3-Chloro-6-(ethyl-p-tolyloxycarbonyl-amino)-5,6,7,8-tetrahydro-naphthalen-2-ylsulfanyl]-2-methylpropionic acid tert-butyl ester Compound 5.0

EXAMPLE 58

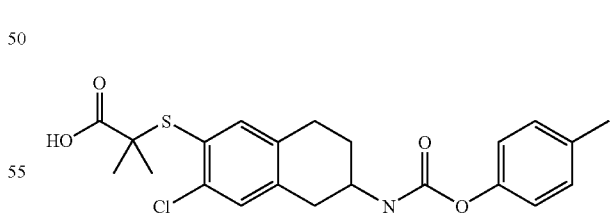

To a mixture of 2-(3-chloro-6-ethylamino-5,6,7,8-tetrahydro-naphthalen-2-ylsulfanyl)-2-methyl-propionic acid tert-butyl ester and borane complex (80 mg; 201 μmol), dissolved in CH$_2$Cl$_2$ (2 mL), at 0° C. is added p-tolyl chloroformate (35 μL; 241 μmol). The reaction was slowly warmed to RT and allowed to stir at RT for 6 days. The solvent was removed under reduced pressure and the crude residue was purified by flash chromatography (SiO$_2$) eluting with a hexanes-EtOAc gradient to afford 30 mg (29%) of 2-[3-chloro-6-(ethyl-p-tolyloxycarbonyl-amino)-5,6,7,8-tetrahydro-naphthalen-2-ylsulfanyl]-2-methyl-propionic acid tert-butyl ester as a clear oil.

$^1$H NMR (300 MHz, CDCl$_3$): δ 6.67-7.29 (m, 6H), 4.28 (m, 1H), 3.40 (m, 2H), 2.87-2.97 (m, 4H), 2.33 (s, 3H), 1.89-2.06 (m, 2H), 1.39-1.46 (m, 15H), 1.21-1.31 (m, 3H)

Compound 5.0 (23 mg; 59%) was prepared following Step M of Route 2.

$^1$H NMR (300 MHz, CD$_3$OD): δ 6.96-7.34 (m, 6H), 4.27 (m,1 H), 3.49 (m, 2H), 2.91-3.14 (m, 4H), 2.32 (s, 3H), 2.10 (m, 2H), 1.45 (m, 6H), 1.28 (m, 3H) LC/MS: C$_{24}$H$_{28}$ClNO$_4$S: m/z462 (M+1)

2-{3-Chloro-6-[(4-chloro-phenoxycarbonyl)-ethyl-amino]-5,6,7,8-tetrahydro-naphthalen-2-ylsulfanyl}-2-methyl-propionic acid Compound 5.1

EXAMPLE 59

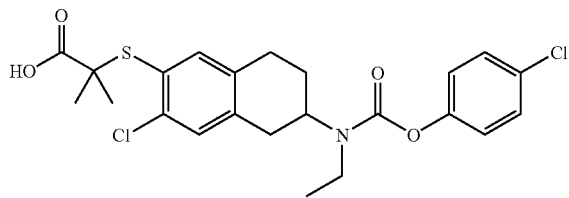

Compound 5.1 (34 mg; 35% for 2 steps; white solid) was prepared following Route 5, substituting 4-chlorophenyl chloroformate for p-tolyl chloroformate and Step M of Route 2.

$^1$H NMR (300 MHz, CD$_3$OD): δ 7.11-7.39 (m, 6H), 4.30 (m, 1H), 3.47 (m, 2H), 2.91-3.15 (m, 4H), 2.06 (m, 2H), 1.45 (m, 6H), 1.28 (m, 3H) LC/MS: C$_{23}$H$_{25}$Cl$_2$NO$_4$S: m/z 482 (M+1)

2-{6-[Ethyl-(4-trifluoromethoxy-phenoxycarbonyl)-amino]-5,6,7,8-tetrahydro-naphthalen-2-ylsulfanyl}-2-methyl-propionic acid Compound 5.2

EXAMPLE 60

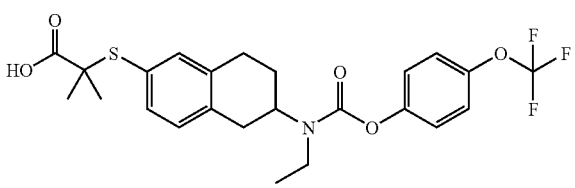

Compound 5.2 can be prepared prepared following Route 5, substituting carbonic acid 1-chloro-ethyl ester 4-trifluoromethoxy phenyl ester for p-tolyl chloroformate and Step M of Route 2.

Alternatively, compound 5.2 can be prepared using the following procedure:

A. Carbonic acid 1-chloro-ethyl ester 4-trifluoromethoxy-phenyl ester

Scheme 1. A solution of 1-chloroethyl chloroformate (1.03 g; 7.20 mmol) in CH$_2$Cl$_2$ (10 mL) was cooled to 0° C., trifluoromethoxyphenol (1.09 g; 6.0 mmol) and triethylamine were added, and the resulting solution was warmed to RT. After stirred for 3 h, the reaction was quenched with saturated NaHCO$_3$, and extracted with EtOAc (3 times). The combined organic extracts were washed with water, brine, dried over Na$_2$SO$_4$, and the solvent was removed under reduced pressure. The crude residue was purified by flash chromatography eluting with Hexane-EtOAc (10:1) to provide 1.54 g (90%) of carbonic acid 1-chloro-ethyl ester 4-trifluoromethoxy-phenyl ester as a colorless oil.

$^1$H NMR (400 MHz, CDCl$_3$): δ 7.26 (m, 4 H), 6.49 (q,1 H), 1.91 (d, 3H)

B. Ethyl-(6-methoxy-1,2,3,4-tetrahydro-naphthalen-2-yl)-carbamic acid 4-trifluoromethoxy-phenyl ester Scheme 1. To a mixture of 6-methoxy-2-tetralone (950 mg; 5.39 mmol), 2 M of ethylamine in THF (5.4 mL; 10.78 mmol) and acetic acid (648 mg; 10.78 mmol) in CH$_2$Cl$_2$ (5 mL) was added sodium triacetoxyborohydride (2.29 g; 10.78 mmol). The reaction mixture was stirred at RT for 3 h, then 1N solution of NaOH was added, and extracted with ether (3 times). The combined organic extracts were dried over Na$_2$SO$_4$, and the solvent was removed under reduced pressure to give a light-yellow oil. This oil was added to a solution of carbonic acid 1-chloro-ethyl ester 4-trifluoromethoxy-phenyl ester (1.23g; 4.31 mmol) in toluene(8 mL), and the reaction mixture was stirred for 1 h at RT followed by 1 h at 90° C. The reaction was allowed to cool to RT, diluted with Et$_2$O and washed with 1 N of aqueous HCl and saturated NaHCO$_3$. The organic extract was dried over Na$_2$SO$_4$, and the solvent was removed under reduced pressure. Flash chromatography of the residue with a gradient of hexane-CH$_2$Cl$_2$ gave 1.05 g (48%) of ethyl-(6-methoxy-1,2,3,4-tetrahydro-naphthalen-2-yl)-carbamic acid 4-trifluoromethoxy-phenyl ester as a white solid.

$^1$H NMR (400 MHz, CDCl$_3$): δ 7.10-7.30 (m, 4 H), 6.99 (d, 1H), 6.71 (d, 1H), 6.64 (s, 1H), 4.33 (m, 1H), 3.77 (s, 3H), 3.41 (m, 2 H), 2.93 (m, 4H), 2.04 (m, 2H), 1.31 (m, 3H) LC/MS: C$_{21}$H$_{23}$F$_3$NO$_4$: m/z410 (M+1)

C. Ethyl-(6-hydroxy-1,2,3,4-tetrahydro-naphthalen-2-yl)-carbamic acid 4-trifluoromethoxy-phenyl ester Scheme 1. A solution of ethyl-(6-methoxy-1,2,3,4-tetrahydro-naphthalen-2-yl)-carbamic acid 4-trifluoromethoxy-phenyl ester (898.6 mg; 2.19 mmol) in anhydrous CH$_2$Cl$_2$ (8 mL) was cooled to −78° C., a 1.0 M solution of boron tribromide-CH$_2$Cl$_2$ (6.57 mL, 6.57 mmol) was added slowly. Upon completion of the addition, the reaction mixture was allowed to warm to RT, quenched with MeOH (10 mL) and stirred for an additional 2 h. The solvents were evaporated, and the residue was purified by flash chromatography with hexane-EtOAc (2.5:1) to give 649.4 mg (75%) of ethyl-(6-hydroxy-1,2,3,4-tetrahydro-naphthalen-2-yl)-carbamic acid 4-trifluoromethoxy-phenyl ester as a white solid.

$^1$H NMR (300 MHz, CDCl$_3$): δ 7.05-7.30 (m, 4 H), 6.90 (m, 1H), 7.41-7.60 (m, 2H), 5.05 (s, 1H), 4.30 (m, 1 H), 3.41

(m, 2H), 2.90 (m, 4H), 1.99 (m, 2H), 1.31 (m, 3H) LC/MS: $C_{20}H_{21}F_3NO_4$: m/z 396 (M+1)

D. Ethyl-(6-triisopropylsilanylsulfanyl-1,2,3.4-tetrahydro-naphthalen-2-yl)-carbamic acid 4-trifluoromethoxy-phenyl ester Scheme 1. A solution of ethyl-(6-hydroxy-1,2,3,4-tetrahydro-naphthalen-2-yl)-carbamic acid 4-trifluoromethoxy-phenyl ester (245.1 mg; 0.62 mmol) in anhydrous $CH_2Cl_2$ (3 mL) and THF (3 mL) was cooled to −30° C., triethylamine (216 uL,1.55 mmol) and triflic anhydride (125 uL, 0.74 mmol) were successively added. The resulting mixture was stirred at RT for 2 h, then quenched with water, and extracted with $Et_2O$ (3 times). The combined organic extracts were washed with water, brine, dried over $Na_2SO_4$, and the solvent was removed under reduced pressure. Flash chromatography of the residue with hexane-EtOAc (5:1) yielded 301.6 mg (92%) of the triflate. This triflate (279.8 mg; 0.53 mmol) and tetrakis(triphenylphosphine)palladium (61.2 mg; 0.053 mmol) were added to a toluene solution generated from triisopropylsilanethiol (126 uL, 0.58 mmol) and NaH (13.9 mg; 0.58 mmol) at RT. The resulting mixture was vacuumed twice, and refluxed for 4 h, and concentrated under reduced pressure. Flash chromatography of the residue with hexane-EtOAc (10:1) afforded 261.8 mg (87%) of ethyl-(6-triisopropylsilanylsulfanyl-1,2,3,4-tetrahydro-naphthalen-2-yl)-carbamic acid 4-trifluoromethoxy-phenyl ester as a light-color oil.

$^1$H NMR (300 MHz, $CDCl_3$): δ 6.82-7.29(m, 7 H), 4.32 (m, 1H), 3.40 (m, 2H), 2.81-3.05 (m, 4H), 2.05 (m, 2H), 1.12-1.34 (m, 6H), 1.03-1.10 (m, 18H) LC/MS: $C_{29}H_{41}F_3NO_3SSi$: m/z 568 (M+1)

E. 2-{6-[Ethyl-(4-trifluoromethoxy-phenoxycarbonyl)-amino]-5,6,7,8-tetrahydronaphthalen-2-ylsulfanyl}-2-methyl-propionic acid tert-butyl ester Scheme 1. A solution of ethyl-(6-triisopropylsilanylsulfanyl-1,2,3,4-tetrahydro-naphthalen-2-yl)-carbamic acid 4-trifluoromethoxy-phenyl ester (260.0 mg; 0.46 mmol) and tert-butyl 2-bromoisobutylrate (130 uL, 0.69 mmol) in anhydrous THF (2 mL) was cooled to 0° C., a 1.0 M solution of TBAF (690 uL, 0.69 mmol) was added, then the reaction was warmed to RT, stirred for 1 h, and then diluted with water, extracted with $Et_2O$ (3 times). The combined organic extracts were dried over $Na_2SO_4$, and the solvent removed under reduced pressure. The crude residue was purified by flash chromatography eluting with Hexane-EtOAc (7:1) to provide 229.2 mg (90%) of 2-{6-[ethyl-(4-trifluoromethoxy-phenoxycarbonyl)-amino]-5,6,7,8-tetrahydronaphthalen-2-ylsulfanyl}-2-methyl-propionic acid tert-butyl ester as a light-color oil.

$^1$H NMR (300 MHz, $CDCl_3$): δ 6.95-7.28 (m, 7 H), 4.34 (m, 1H), 3.41 (m, 2H), 2.96 (m, 2H), 2.91 (m, 2H), 3.41 (m, 2H), 2.06 (m, 2H), 1.44 (s, 6H), 1.42 (s, 9H), 1.28 (m, 3H) LC/MS: $C_{28}H_{34}F_3NO_5SNa$: m/z 576 (M+Na)

F. 2-{6-[Ethyl-(4-trifluoromethoxy-phenoxycarbonyl)-amino]-5,6,7,8-tetrahydro-naphthalen-2-ylsulfanyl}-2-methyl-propionic acid Scheme 1. A solution of 2-{6-[ethyl-(4-trifluoromethoxy-phenoxycarbonyl)-amino]-5,6,7,8-tetrahydro-naphthalen-2-ylsulfanyl}-2-methyl-propionic acid (120.8 mg; 0.22 mmol) in $CH_2Cl_2$ (4 mL) was cooled to −78° C., and trifluoroacetic acid (4 mL) was added slowly. The reaction mixture was allowed to warm to RT, and stirred for 1.5 h. The solvents were then evaporated, and the residue was purified by flash chromatography with $CH_2Cl_2$-MeOH (94:6) to give 2-{6-[ethyl-(4-trifluoromethoxy-phenoxycarbonyl)-amino]-5,6,7,8-tetrahydro-naphthalen-2-ylsulfanyl}-2-methyl-propionic acid as a white solid.

$^1$H NMR (400 MHz, $CDCl_3$): δ 6.96-7.28 (m, 7H), 4.30 (m, 1H), 3.39 (m, 2H), 2.85-3.10 (m, 4H), 2.06 (m, 2H), 1.49 (s, 6H), 1.28 (m, 3H) LC/MS: $C_{24}H_{27}F_3NO_5S$: m/z 498 (M+1)

D. Formulation and Administration

The present compounds are PPAR alpha agonists and are therefore useful in treating or inhibiting the progression of PPAR alpha mediated diseases and conditions, such as diabetes, and complications thereof, such as neuropathy, nephropathy, and retinopathy.

The invention features a method for treating a subject with a PPAR alpha-mediated disease, said method comprising administering to the subject a therapeutically effective amount of a pharmaceutical composition comprising a compound of the invention. The invention also provides a method for treating or inhibiting the progression of diabetes or impaired glucose tolerance in a subject, wherein the method comprises administering to the subject a therapeutically effective amount of a pharmaceutical composition comprising a compound of the invention.

The compounds of the present invention may be formulated into various pharmaceutical forms for administration purposes. To prepare these pharmaceutical compositions, an effective amount of a particular compound, in base or acid addition salt form, as the active ingredient is intimately mixed with a pharmaceutically acceptable carrier.

A carrier may take a wide variety of forms depending on the form of preparation desired for administration. These pharmaceutical compositions are desirably in unitary dosage form suitable, preferably, for oral administration or parenteral injection. For example, in preparing the compositions in oral dosage form, any of the usual pharmaceutical media may be employed. These include water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. In view of their ease in administration, tablets and capsules represent the most advantageous oral dosage unit form, in which case solid pharmaceutical carriers are generally employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Such additives may facilitate the administration to the skin and/or may be helpful for preparing the desired compositions. These compositions may be administered in various ways, e.g., as a transdermal patch, as a spot-on, as an ointment. Acid addition salts of the compounds of formula I, due to their increased water solubility over the corresponding base form, are more suitable in the preparation of aqueous compositions.

It is especially advantageous to formulate the aforementioned pharmaceutical compositions in dosage unit form for ease of administration and uniformity of dosage. Dosage unit form as used in the specification herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Pharmaceutically acceptable acid addition salts include the therapeutically active non-toxic acid addition salt forms which the disclosed compounds are able to form. The latter can conveniently be obtained by treating the base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, palmoic and the like acids. The term addition salt also comprises the solvates which the disclosed componds, as well as the salts thereof, are able to form. Such solvates are for example hydrates, alcoholates and the like. Conversely the salt form can be converted by treatment with alkali into the free base form.

Stereoisomeric forms define all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the (R)- or (S)-configuration; substituents on bivalent cyclic saturated radicals may have either the cis- or trans-configuration. The invention encompasses stereochemically isomeric forms including diastereoisomers, as well as mixtures thereof in any proportion of the disclosed compounds. The disclosed compounds may also exist in their tautomeric forms. Such forms although not explicitly indicated in the above and following formulae are intended to be included within the scope of the present invention. For example, in compound 2.1 or Example 3, there is a chiral center on the C-2 of the indane ring. For this compound, the (R) isomer is more active than the (S) isomer.

E. Use

Those of skill in the treatment of disorders or conditions mediated by the PPAR alpha could easily determine the effective daily amount from the test results presented hereinafter and other information. In general it is contemplated that a therapeutically effective dose would be from 0.001 mg/kg to 5 mg/kg body weight, more preferably from 0.01 mg/kg to 0.5 mg/kg body weight. It may be appropriate to administer the therapeutically effective dose as two, three, four or more sub-doses at appropriate intervals throughout the day. Said sub-doses may be formulated as unit dosage forms, for example, containing 0.05 mg to 250 mg or 750 mg, and in particular 0.5 to 50 mg of active ingredient per unit dosage form. Examples include 2 mg, 4 mg, 7 mg, 10 mg, 15 mg, 25 mg, and 35 mg dosage forms. Compounds of the invention may also be prepared in time-release or subcutaneous or transdermal patch formulations. Disclosed compound may also be formulated as a spray or other topical or inhalable formulations.

The exact dosage and frequency of administration depends on the particular compound of formula (I) used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned herein are therefore only guidelines.

The next section includes detailed information relating to the use of the disclosed compounds and compositions.

The compounds of the present invention are pharmaceutically active, for example, as PPAR alpha agonists. According to one aspect of the invention, the compounds are preferably selective PPAR alpha agonists, having an activity index (e.g., PPAR alpha potency over PPAR gamma potency) of 10 or more, and preferably 15, 25, 30, 50 or 100 or more.

PPAR alpha agonists are useful for the treatment, prevention, or inhibiting the progression of one or more of the following conditions or diseases: Type II diabetes, impaired glucose tolerance, impaired fasting glucose, neuropathy, nephropathy, retinopathy, insulin resistance, hyperglycemia, and hyperinsulinemia.

Combination Therapy

The compounds of the present invention may be used in combination with other pharmaceutically active agents. These agents include anti-diabetic agents, such as mefformin, insulin, and insulin sensitizers (such as TZD's; blood-pressure lowering agents; lipid lowering agents; and Acrp30 or Adiponectin modulators such as Famoxin.

Methods are known in the art for determining effective doses for therapeutic and prophylactic purposes for the disclosed pharmaceutical compositions or the disclosed drug combinations, whether or not formulated in the same composition. For therapeutic purposes, the term "jointly effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term ""jointly effective amount" refers to that amount of each active compound or pharmaceutical agent, alone or in combination, that treats or inhibits in a subject the onset or progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both drugs are administered in an amount that is sub-therapeutic or sub-prophylactic if administered alone, but are therapeutic or prophylactic when administered together.

Anti-diabetic agents include thiazolidinedione and non-thiazolidinedione insulin sensitizers, which decrease peripheral insulin resistance by enhancing the effects of insulin at target organs and tissues.

Some of the following agents are known to bind and activate the nuclear receptor peroxisome proliferator-activated receptor-gamma (PPARγ) which increases transcription of specific insulin-responsive genes. Examples of PPAR-gamma agonists are thiazolidinediones such as:
  (1) rosiglitazone (2,4-thiazolidinedione,5-((4-(2-(methyl-2-pyridinylamino) ethoxy) phenyl) methyl)-, (Z)-2-butenedioate (1:1) or 5-((4-(2-(methyl-2-pyridinylamino)ethoxy)phenyl)methyl)-2,4-thiazolidinedione, known as AVANDIA; also known as BRL 49653, BRL 49653C, BRL 49653c, SB 210232, or rosiglitazone maleate);
  (2) pioglitazone (2,4-thiazolidinedione, 5-((4-(2-(5-ethyl-2-pyridinyl)ethoxy)phenyl)methyl)-, monohydrochloride, (+−)- or 5-((4-(2-(5-ethyl-2-pyridyl)ethoxy)phenyl)methy)-2,4-thiazolidinedione, known as ACTOS, ZACTOS, or GLUSTIN; also known as AD 4833, U 72107, U 72107A, U 72107E, pioglitazone hydrochloride (USAN));
  (3) troglitazone (5-((4-((3,4-dihydro-6-hydroxy-2,5,7,8-tetramethyl-2H-1-benzopyran-2-yl)methoxy)phenyl) methyl)-2,4-thiazolidinedione, known as NOSCAL, REZULIN, ROMOZIN, or PRELAY; also known as Cl 991, CS 045, GR 92132, GR 92132X);
  (4) isaglitazone ((+)-5-[[6-[(2-fluorophenyl)methoxy]-2-naphthalenyl]methyl]-2,4-thiazolidinedione or 5-((6-((2-fluorophenyl) methoxy)-2-naphthalenyl) methyl-2,4-thiazolidinedione or 5-(6-(2-fluorobenzyloxy) naphthalen-2-ylmethyl) thiazolidine-2,4-dione, also known as MCC-555 or neoglitazone); and
  (5) 5-BTZD.

Additionally, the non-thiazolidinediones that act as insulin sensitizing agents include, but are not limited to:
  (1) JT-501 (JTT 501, PNU-1827, PNU-716-MET-0096, or PNU 182716: isoxazolidine-3,5-dione, 4-((4-(2-phenyl-5-methyl)-1,3-oxazolyl) ethylphenyl-4) methyl-);
  (2) KRP-297 (5-(2,4-dioxothiazolidin-5-ylmethyl)-2-methoxy-N-(4-(trifluoromethyl)benzyl)benzamide or 5-((2,4-dioxo-5-thiazolidinyl) methyl)-2-methoxy-N-((4-(trifluoromethyl)phenyl)methyl)benzamide); and
  (3) Farglitazar (L-tyrosine, N-(2-benzoylphenyl)-o-(2-(5-methyl-2-phenyl-4-oxazolyl)ethyl)- or N-(2-benzoylphenyl)-O-(2-(5-methyl-2-phenyl-4-oxazolyl) ethyl)-L-tyrosine, or GW2570 or GI-262570).

Other agents have also been shown to have PPAR modulator activity such as PPAR gamma, SPPAR gamma, and/or PPAR delta/gamma agonist activity. Examples are listed below:
  (1) AD 5075;
  (2) R 119702((+−)-5-(4-(5-Methoxy-1H-benzimidazol-2-ylmethoxy)benzyl)thiazolin-2,4-dione hydrochloride, or Cl 1037 or CS 011);
  (3) CLX-0940 (peroxisome proliferator-activated receptor alpha agonist/peroxisome proliferator-activated receptor gamma agonist);
  (4) LR-90 (2,5,5-tris (4-chlorophenyl)-1,3-dioxane-2-carboxylic acid, PPARdelta/γ agonist);
  (5) Tularik (PPARγ agonist);
  (6) CLX-0921 (PPARγ agonist);
  (7) CGP-52608 (PPAR agonist);
  (8) GW409890 (PPAR agonist);
  (9) GW-7845 (PPAR agonist);
  (10) L-764406 (PPAR agonist);
  (11) LG-101280 (PPAR agonist);
  (12) LM-4156 (PPAR agonist);
  (13) Risarestat (CT-112);
  (14) YM 440 (PPAR agonist);
  (15) AR-H049020 (PPAR agonist);
  (16) GW 0072 (4-(4-((2S,5S)-5-(2-(bis (phenylmethyl) amino)-2-oxoethyl)-2-heptyl-4-oxo-3-thiazo lidinyl) butyl) benzoic acid);
  (17) GW 409544 (GW-544 or GW409544);
  (18) NN 2344 (DRF 2593);
  (19) NN 622 (DRF 2725);
  (20) AR-H039242 (AZ-242);
  (21) GW 9820 (fibrate);
  (22) GW 1929 (N-(2-benzoylphenyl)-O-(2-(methyl-2-pyridinylamino) ethyl)-L-tyrosine, known as GW 2331, PPAR alpha/γ agonist);
  (23) SB 219994 ((S)-4-(2-(2-benzoxazolylmethylamino) ethoxy)-alpha-(2,2,2-trifluoroethoxy) benzen epropanoic acid or 3-(4--(2-(N-(2-benzoxazolyl)-N-methylamino)ethoxy)phenyl)-2(S)-(2,2,2-trifluoroethoxy) propionic acid or benzenepropanoic acid,4-(2-(2-benzoxazolylmethylamino)ethoxy)-alpha-(2,2,2-trifluoroethoxy)-, (alphaS)-, PPARalpha/γ agonist);
  (24) L-796449 (PPAR alpha/γ agonist);
  (25) Fenofibrate (Propanoic acid, 2-[4-(4-chlorobenzoyl) phenoxy]-2-methyl-, 1-methylethyl ester, known as TRICOR, LIPCOR, LIPANTIL, LIPIDIL MICRO PPAR alpha agonist);
  (26) GW-9578 (PPAR alpha agonist);
  (27) GW-2433 (PPAR alpha/γ agonist);
  (28) GW-0207 (PPARγ agonist);
  (29) LG-100641 (PPARγ agonist);
  (30) LY-300512 (PPARγ agonist);
  (31) NID525-209 (NID-525);
  (32) VDO-52 (VDO-52);
  (33) LG 100754 (peroxisome proliferator-activated receptor agonist);
  (34) LY-510929 (peroxisome proliferator-activated receptor agonist);
  (35) bexarotene (4-(1-(3,5,5,8,8-pentamethyl-5,6,7,8-tetrahydro-2-naphthalenyl)ethenyl)benzoic acid, known as TARGRETIN, TARGRETYN, TARGREXIN; also known as LGD 1069, LG 100069, LG 1069, LDG 1069, LG 69, RO 264455); and
  (36) GW-1536 (PPAR alpha/γ agonist).

(B) Other insulin sensitizing agents include, but are not limited to:
  (1) INS-1 (D-chiro inositol or D-1,2,3,4,5,6-hexahydroxycyclohexane);
  (2) protein tyrosine phosphatase 1 B (PTP-1B) inhibitors;
  (3) glycogen synthase kinase-3 (GSK3) inhibitors;
  (4) beta 3 adrenoceptor agonists such as ZD 2079 ((R)-N-(2-(4-(carboxymethyl) phenoxy) ethyl)-N-(2-hydroxy-2-phenethyl) ammonium chloride, also known as ICl D 2079) or AZ 40140;
  (5) glycogen phosphorylase inhibitors;
  (6) fructose-1,6-bisphosphatase inhibitors;
  (7) chromic picolinate, vanadyl sulfate (vanadium oxysulfate);
  (8) KP 102 (organo-vanadium compound);
  (9) chromic polynicotinate;
  (10) potassium channel agonist NN 414;
  (11) YM 268 (5,5'-methylene-bis(1,4-phenylene)bismethylenebis(thiazolidine-2,4-dione);
  (12) TS 971;

(13) T 174 ((+−)-5-(2,4-dioxothiazolidin-5-ylmethyl)-2-(2-naphthylmethyl)benzoxazole);
(14) SDZ PGU 693 ((+)-trans-2(S-((4-chlorophenoxy)methyl)-7alpha-(3,4-dichlorophenyl)tetrahydropyrrolo (2,1-b)oxazol-5 (6H)-one);
(15) S 15261 ((−)-4-(2-((9H-fluoren-9-ylacetyl)amino)ethyl)benzoic acid 2-((2-methoxy-2-(3-(trifluoromethyl)phenyl)ethyl)amino)ethyl ester);
(16) AZM 134 (Alizyme);
(17) ARIAD;
(18) R 102380;
(19) PNU 140975 (1-(hydrazinoiminomethyl)hydrazino) acetic acid;
(20) PNU 106817 (2-(hydrazinoiminomethyl)hydrazino) acetic acid;
(21) NC 2100 (5-((7-(phenylmethoxy)-3-quinolinyl)methyl)-2,4-thiazolidinedione;
(22) MXC 3255;
(23) MBX 102;
(24) ALT 4037;
(25) AM 454;
(26) JTP 20993 (2-(4-(2-(5-methyl-2-phenyl-4-oxazolyl) ethoxy) benzyl)-malonic acid dimethyl diester);
(27) Dexlipotam (5 (R)-(1,2-dithiolan-3-yl) pentanoic acid, also known as (R)-alpha lipoic acid or (R)-thioctic acid);
(28) BM 170744 (2,2-Dichloro-12-(p-chlorophenyl) dodecanoic acid); (29) BM 152054 (5-(4-(2-(5-methyl-2-(2-thienyl)oxazol-4-yl) ethoxy)benzothien-7-ylmethyl)thiazolidine-2,4-dione);
(30) BM 131258 (5-(4-(2-(5-methyl-2-phenyloxazol-4-yl)ethoxy) benzothien-7-ylmethyl)thiazolidine-2,4-dione);
(31) CRE 16336 (EML 16336);
(32) HQL 975 (3-(4-(2-(5-methyl-2-phenyloxazol-4-yl) ethoxy) phenyl)-2 (S)-(propylamino)propionic acid);
(33) DRF 2189 (5-((4-(2-(1-Indolyl)ethoxy)phenyl)methyl)thiazolidine-2,4-dione);
(34) DRF 554158;
(35) DRF-NPCC;
(36) CLX 0100, CLX 0101, CLX 0900, or CLX 0901;
(37) IkappaB Kinase (IKK B) Inhibitors
(38) mitogen-activated protein kinase (MAPK) inhibitors 38 MAPK Stimulators
(39) phosphatidyl-inositide triphosphate
(40) insulin recycling receptor inhibitors
(41) glucose transporter 4 modulators
(42) TNF-α antagonists
(43) plasma cell differentiation antigen-1 (PC-1) Antagonists
(44) adipocyte lipid-binding protein (ALBP/aP2) inhibitors
(45) phosphoglycans
(46) Galparan;
(47) Receptron;
(48) islet cell maturation factor;
(49) insulin potentiating factor (IPF or insulin potentiating factor-1);
(50) somatomedin C coupled with binding protein (also known as IGF-BP3, IGF-BP3, SomatoKine);
(51) Diab II (known as V411) or Glucanin, produced by Biotech Holdings Ltd. or Volque Pharmaceutical;
(52) glucose-6 phosphatase inhibitors;
(53) fatty acid glucose transport protein;
(54) glucocorticoid receptor antagonists; and
(55) glutamine:fructose-6-phosphate amidotransferase (GFAT) modulators.

(C) Biguanides, which decrease liver glucose production and increases the uptake of glucose. Examples include metformin such as:
(1) 1,1-dimethylbiguanide (e.g., Metformin-DepoMed, Metformin-Biovail Corporation, or METFORMIN GR (metformin gastric retention polymer)); and
(2) metformin hydrochloride (N,N-dimethylimidodicarbonimidic diamide monohydrochloride, also known as LA 6023, BMS 207150, GLUCOPHAGE, or GLUCOPHAGE XR.

(D) Alpha-glucosidase inhibitors, which inhibit alpha-glucosidase. Alpha-glucosidase converts fructose to glucose, thereby delaying the digestion of carbohydrates. The undigested carbohydrates are subsequently broken down in the gut, reducing the post-prandial glucose peak. Examples include, but are not limited to:
(1) acarbose (D-glucose, O-4,6-dideoxy-4-(((1 S-(1alpha,4alpha,5beta,6alpha))-4,5,6-trihydroxy-3-(hydroxymethyl)-2-cyclohexen-1-yl)amino)-alpha-D-glucopyranosyl-(1-4)-O-alpha-D-glucopyranosyl-(1-4)-, also known as AG-5421, Bay-g-542, BAY-g-542, GLUCOBAY, PRECOSE, GLUCOR, PRANDASE, GLUMIDA, or ASCAROSE);
(2) Miglitol (3,4,5-piperidinetriol, 1-(2-hydroxyethyl)-2-(hydroxymethyl)-, (2R (2alpha, 3beta, 4alpha, 5beta))- or (2R,3R,4R,5S)-1-(2-hydroxyethyl)-2-(hydroxymethyl-3,4,5-piperidinetriol, also known as BAY 1099, BAY M 1099, BAY-m-1099, BAYGLITOL, DIASTABOL, GLYSET, MIGLIBAY, MITOLBAY, PLUMAROL);
(3) CKD-711 (0-4-deoxy-4-((2,3-epoxy-3-hydroxymethyl-4,5,6-trihydroxycyclohexane-1-yl) amino)-alpha-b-glucopyranosyl-(1-4)-alpha-D-glucopyranosyl-(1-4)-D-glucopyranose);
(4) emiglitate (4-(2-((2R,3R,4R,5S)-3,4,5-trihydroxy-2-(hydroxymethyl)-1-piperidinyl) ethoxy) benzoic acid ethyl ester, also known as BAY o 1248 or MKC 542);
(5) MOR 14 (3,4,5-piperidinetriol, 2-(hydroxymethyl)-1-methyl-, (2R-(2alpha,3beta,4alpha,5beta))-, also known as N-methyideoxynojirimycin or N-methylmoranoline); and
(6) Voglibose (3,4-dideoxy-4-((2-hydroxy-1-(hydroxymethyl)ethyl)amino)-2-C-(hydroxymethyl)-D-epi-inositol or D-epi-Inositol,3,4-dideoxy-4-((2-hydroxy-1-(hydroxymethyl)ethyl)amino)-2-C-(hydroxymethyl)-, also known as A 71100, AO 128, BASEN, GLUSTAT, VOGLISTAT.

(E) Insulins include regular or short-acting, intermediate-acting, and long-acting insulins, non-injectable or inhaled insulin, tissue selective insulin, glucophosphokinin (D-chiroinositol), insulin analogues such as insulin molecules with minor differences in the natural amino acid sequence and small molecule mimics of insulin (insulin mimetics), and endosome modulators. Examples include, but are not limited to:
(1) Biota;
(2) LP 100;
(3) (SP-5-21)-oxobis (1-pyrrolidinecarbodithioato-S,S') vanadium,
(4) insulin aspart (human insulin (28B-L-aspartic acid) or B28-Asp-insulin, also known as insulin X14, INA-X14, NOVORAPID, NOVOMIX, or NOVOLOG);
(5) insulin detemir (Human 29B-(N6-(1-oxotetradecyl)-L-lysine)-(1A-21A), (1 B-29B)-Insulin or NN 304);
(6) insulin lispro ("28B-L-lysine-29B-L-proline human insulin, or Lys(B28), Pro(B29) human insulin analog, also known as lys-pro insulin, LY 275585, HUMA-LOG, HUMALOG MIX 75/25, or HUMALOG MIX 50/50);

(7) insulin glargine (human (A21-glycine, B31-arginine, B32-arginine) insulin HOE 901, also known as LANTUS, OPTISULIN);

(8) Insulin Zinc Suspension, extended (Ultralente), also known as HUMULIN U or ULTRALENTE;

(9) Insulin Zinc suspension (Lente), a 70% crystalline and 30% amorphous insulin suspension, also known as LENTE ILETIN II, HUMULIN L, or NOVOLIN L;

(10) HUMULIN 50/50 (50% isophane insulin and 50% insulin injection);

(11) HUMULIN 70/30 (70% isophane insulin NPH and 30% insulin injection), also known as NOVOLIN 70/30, NOVOLIN 70/30 PenFill, NOVOLIN 70/30 Prefilled;

(12) insulin isophane suspension such as NPH ILETIN II, NOVOLIN N, NOVOLIN N PenFill, NOVOLIN N Prefilled, HUMULIN N;

(13) regular insulin injection such as ILETIN II Regular, NOVOLIN R, VELOSULIN BR, NOVOLIN R PenFill, NOVOLIN R Prefilled, HUMULIN R, or Regular U-500 (Concentrated);

(14) ARIAD;

(15) LY 197535;

(16) L-783281; and

(17) TE-17411.

(F) Insulin secretion modulators such as:

(1) glucagon-like peptide-1 (GLP-1) and its mimetics;

(2) glucose-insulinotropic peptide (GIP) and its mimetics;

(3) exendin and its mimetics;

(4) dipeptyl protease (DPP or DPPIV) inhibitors such as (4a) DPP-728 or LAF 237 (2-pyrrolidinecarbonitrile, 1-(((2-((5-cyano-2-pyridinyl)amino)ethyl)amino) acetyl), known as NVP-DPP-728, DPP-728A, LAF-237);

(4b) P 3298 or P32/98 (di-(3N-((2S, 3S)-2-amino-3-methyl-pentanoyl)-1,3-thiazolidine) fumarate);

(4c) TSL 225 (tryptophyl-1,2,3,4-tetrahydroisoquinoline-3-carboxylic acid);

(4d) Valine pyrrolidide (valpyr);

(4e) 1-aminoalkylisoquinolinone-4-carboxylates and analogues thereof;

(4f) SDZ 272-070 (1-(L-Valyl) pyrrolidine);

(4g) TMC-2A, TMC-2B, or TMC-2C;

(4h) Dipeptide nitriles (2-cyanopyrrolodides);

(4i) CD26 inhibitors; and (4j) SDZ 274-444;

(5) glucagon antagonists such as AY-279955; and (6) amylin agonists which include, but are not limited to, pramlintide (AC-137, Symlin, tripro-amylin or pramlintide acetate).

The present compounds may also increase insulin sensitivity with a smaller increase in body weight than that found with the use of existing PPAR gamma agonists. Oral antidiabetic agents may include insulin, sulfonylureas, biguanides, meglitinides, AGI's, PPAR alpha agonists, and PPAR gamma agonists, and dual PPAR alpha/gamma agonists.

PPAR alpha agonists are useful for the treatment, prevention, or inhibiting the progression of one or more of the following conditions or diseases: phase I hyperlipidemia, pre-clinical hyperlipidemia, phase II hyperlipidemia, hypertension, coronary artery disease (CAD), and hypertriglyceridemia. Preferred compounds of the invention are useful in lowering serum levels of low-density lipoproteins (LDL), IDL, and/or small-density LDL and other atherogenic molecules, or molecules that cause atherosclerotic or dyslipidemic complications, thereby reducing cardiovascular complications. Preferred compounds also are useful in elevating levels of high-density lipoproteins (HDL), in lowering levels of triglycerides, LDL, and/or free fatty acids. It is also desirable to lower FPG/HbA1c.

As PPAR alpha agonists, the compounds of the invention may be more potent and efficacious for lowering triglycerides than known fibrates. The present compounds also may increase fat and/or lipid metabolism, providing a method for losing weight, losing fat weight, lowering body mass index, lowering lipids (such as lowering triglycerides), or treating obesity or the condition of being overweight. Examples of lipid lowering agents include bile acid sequestrants, fibric acid derivatives, nicotinic acid, and HMGCoA reductase inhibitors. Specific examples include statins such as LIPITOR™, ZOCOR™, PRAVACHOL™, LESCOL™, and MEVACOR™, and pitavastatin (nisvastatin) (Nissan, Kowa Kogyo, Sankyo, Novartis) and extended release forms thereof, such as ADX-159 (extended release lovastatin), as well as Colestid, Locholest, Questran, Atromid, Lopid, and Tricor.

Examples of blood pressure lowering agents include anti-hypertensive agents, such as angiotensin-converting enzyme (ACE) inhibitors (Accupril, Altace, Captopril, Lotensin, Mavik, Monopril, Prinivil, Univasc, Vasotec, and Zestril), adrenergic blockers (such as Cardura, Dibenzyline, Hylorel, Hytrin, Minipress, and Minizide) alph/beta adrenergic blockers (such as Coreg, Normodyne, and Trandate), calcium channel blockers (such as Adalat, Calan, Cardene, Cardizem, Covera-HS, Dilacor, DynaCirc, Isoptin, Nimotop, Norvace, Plendil, Procardia, Procardia XL, Sula, Tiazac, Vascor, and Verelan), diuretics, antiotensin II receptor antagonists (such as Atacand, Avapro, Cozaar, and Diovan), beta adrenergic blockers (such as Betapace, Blocadren, Brevibloc, Cartrol, Inderal, Kerlone, Lavatol, Lopressor, Sectral, Tenormin, Toprol-XL, and Zebeta), vasodilators (such as Deponit, Dilatrate, SR, lmdur, Ismo, Isordil, Isordil Titradose, Monoket, Nitro-Bid, Nitro-Dur, Nitrolingual Spray, Nitrostat, and Sorbitrate), and combinations thereof (such as Lexxel, Lotrel, Tarka, Teczem, Lotensin HCT, Prinzide, Uniretic, Vaseretic, Zestoretic).

F. Examples

The following chemical and biological examples are intended to illustrate, not limit, the invention.

Example 1

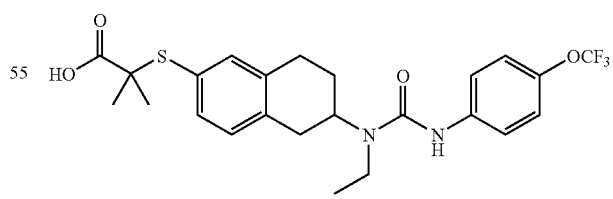

2-{6-[1-Ethyl-3-(4-trifluoromethoxyphenyl)ureido]-5,6,7,8-tetrahydronaphthalen-2-ylsulfanyl}-2-methylpropionic acid $EC_{50}=0.023$ μM Example 2

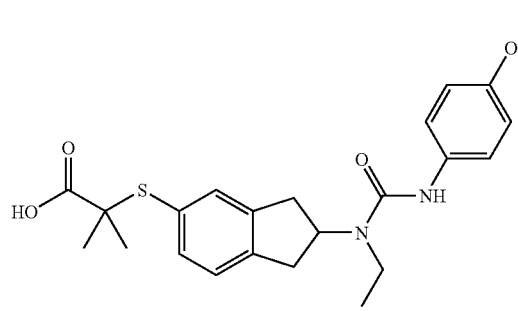

2-{2-[1-Ethyl-3-(4-trifluoromethoxyphenyl)ureido]indan-5-ylsulfanyl}-2-methylpropionic acid $EC_{50}$=0.027 μM Example 3

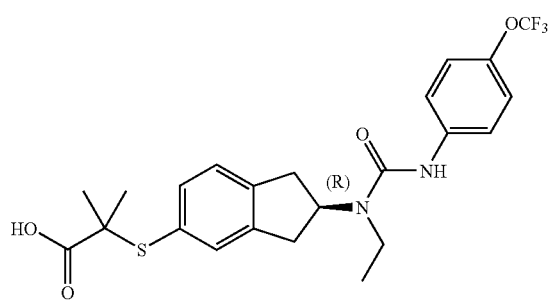

(R)-2-{2-[1-Ethyl-3-(4-trifluoromethoxyphenyl)ureido]indan-5-ylsulfanyl}-2-methylpropionic acid $EC_{50}$=0.008 μM Example 4

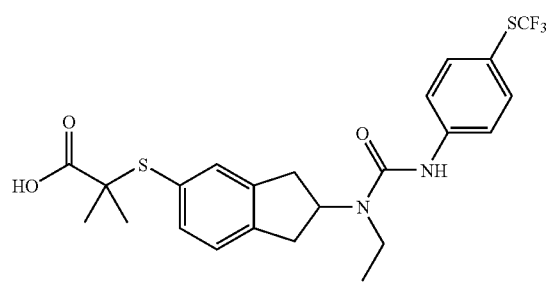

2-{2-[1-Ethyl-3-(4-trifluoromethylsulfanylphenyl)ureido]indan-5-ylsulfanyl}-2-methylpropionic acid $EC_{50}$=0.037 μM Example 5

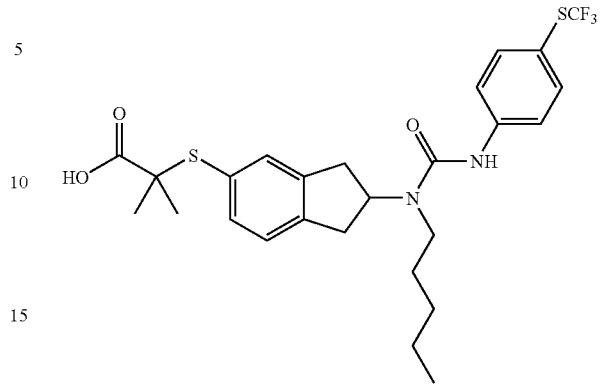

2-Methyl-2-{2-[1-pentyl-3-(4-trifluoromethylsulfanylphenyl)ureido]indan-5-ylsulfanyl}propionic acid $EC_{50}$=0.053 μM Example 6

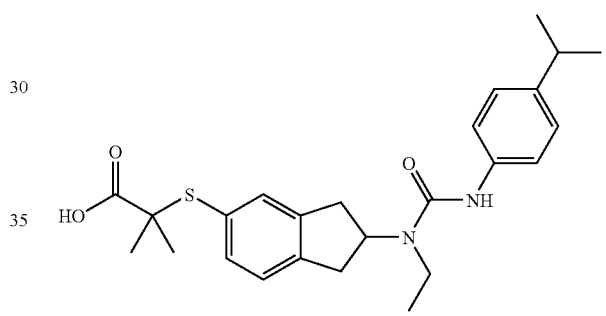

2-{2-[1-Ethyl-3-(4-isopropylphenyl)ureido]indan-5-ylsulfanyl}-2-methylpropionic acid $EC_{50}$=0.056 μM Example 7

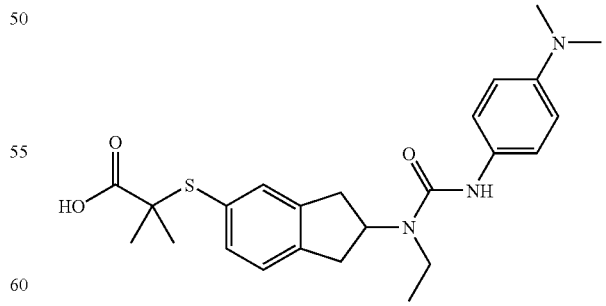

2-{2-[3-(4-Dimethylaminophenyl)-1-ethylureido]indan-5-ylsulfanyl}-2-methylpropionic acid $EC_{50}$=0.075 μM

Example 8

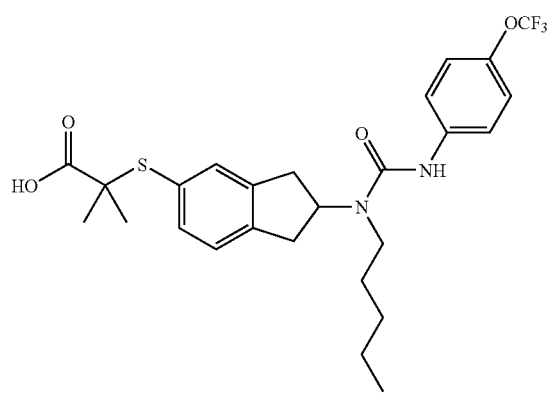

2-Methyl-2-{2-[1-pentyl-3-(4-trifluoromethoxyphenyl)ureido]indan-5-ylsulfanyl}-2-methylpropionic acid $EC_{50}$=0.073 µM

Example 9

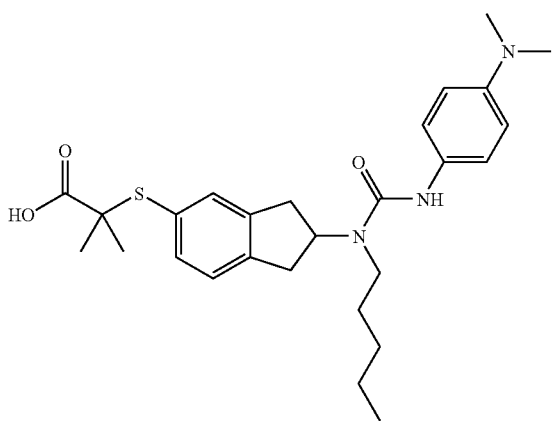

2-{2-[3-(4-Dimethylaminophenyl)-1-pentylureido]indan-5-ylsulfanyl}-2-methylpropionic acid $EC_{50}$=0.131 µM

Example 10

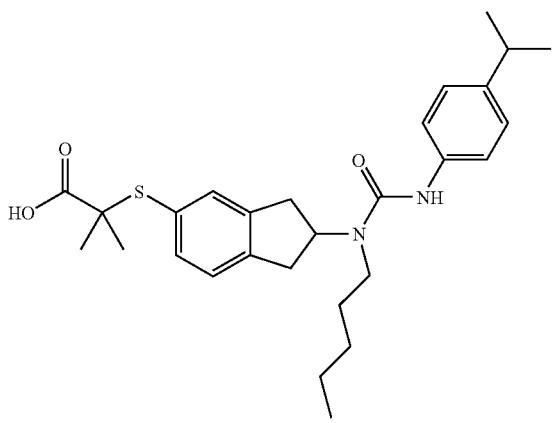

2-{2-[3-(4-Isopropylphenyl)-1-pentylureido]indan-5-ylsulfanyl}-2-methylpropionic acid $EC_{50}$ =0.165 µM

Example 11

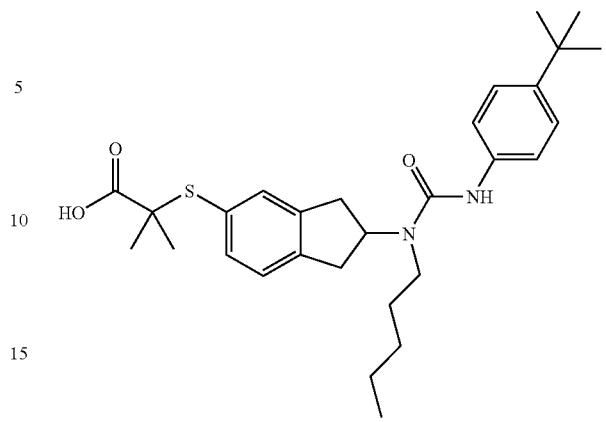

2-{2-[3-(4-tert-Butyl phenyl)-1-pentylureido]indan-5-ylsulfanyl}-2-methyl propionic acid $EC_{50}$=0.173 µM

Example 12

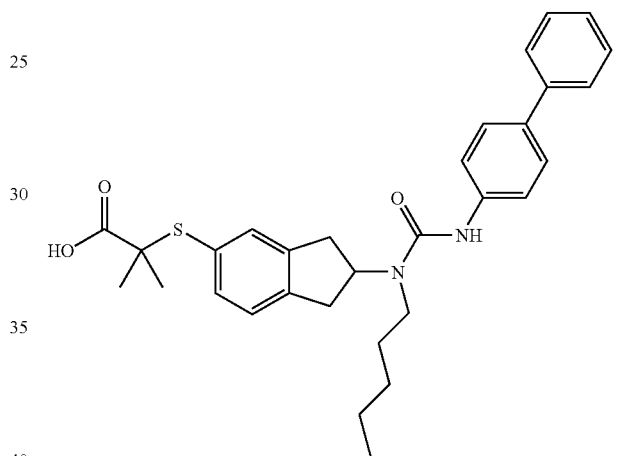

2-[2-(3-Biphenyl-4-yl-1-pentylureido)indan-5-ylsulfanyl]-2-methylpropionic acid $EC_{50}$=0.183 µM

Example 13

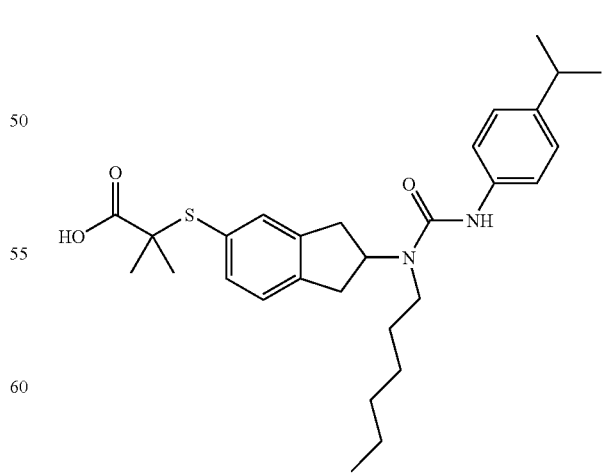

2-{2-[3-(4-Isopropylphenyl)-1-hexylureido]indan-5-ylsulfanyl}-2-methylpropionic acid $EC_{50}$=0.184 µM

Example 14

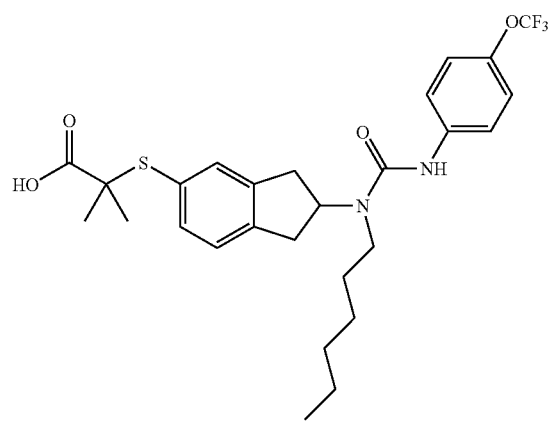

2-Methyl-2-{2-[1-hexyl-3-(4-trifluoromethoxyphenyl)ureido]indan-5-ylsulfanyl}propionic acid

EC$_{50}$=0.213 μM

Example 15

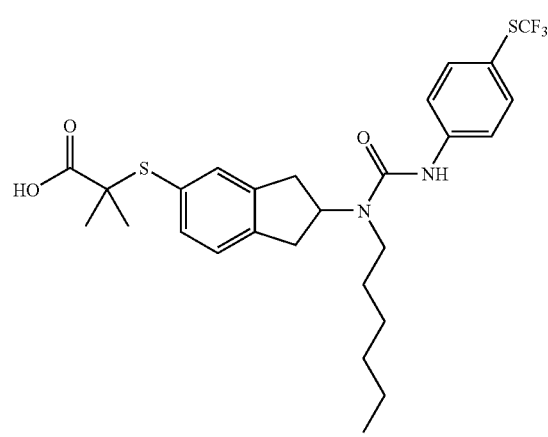

2-Methyl-2-{2-[1-hexyl-3-(4-trifluoromethylsulfanylphenyl)ureido]indan-5-ylsulfanyl}propionic acid

EC$_{50}$=0.123 μM

Example 16

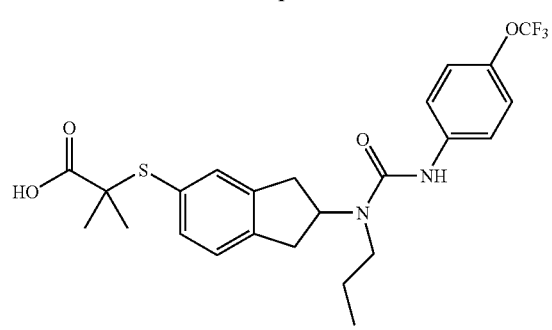

2-Methyl-2-{2-[1-propyl-3-(4-trifluoromethoxyphenyl)ureido]indan-5-ylsulfanyl}propionic acid

EC$_{50}$=0.158 μM

Example 17

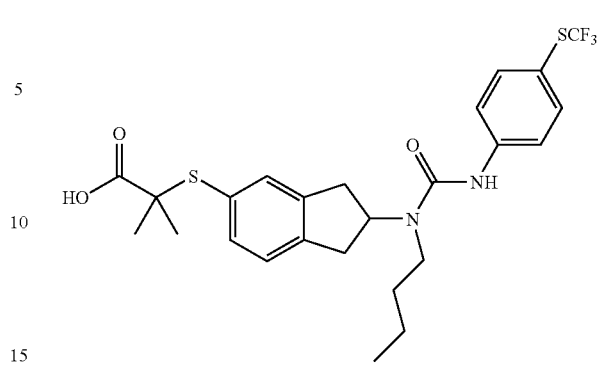

2-Methyl-2-{2-[1-butyl-3-(4-trifluoromethylsulfanylphenyl)ureido]indan-5-ylsulfanyl}propionic acid

EC$_{50}$=0.160 μM

Example 18

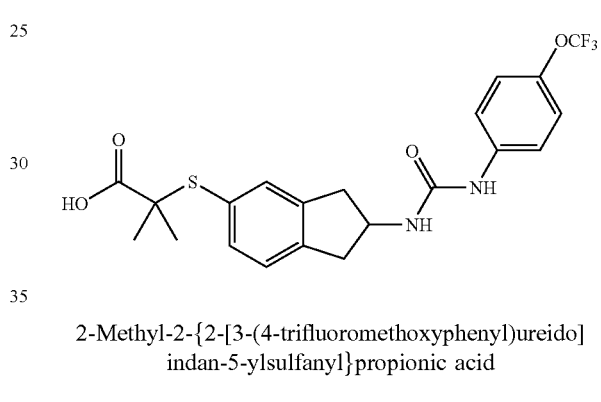

2-Methyl-2-{2-[3-(4-trifluoromethoxyphenyl)ureido]indan-5-ylsulfanyl}propionic acid

EC$_{50}$=0.135 μM

Example 19

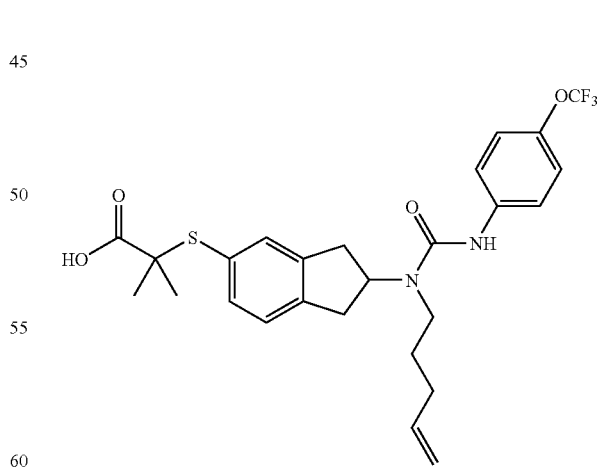

2-Methy-2-{2-[1-pent-4-enyl-3-(4-trifluoromethoxyphenyl)ureido]indan-5-ylsulfanyl}propionic acid

EC$_{50}$=0.125 μM

Example 20

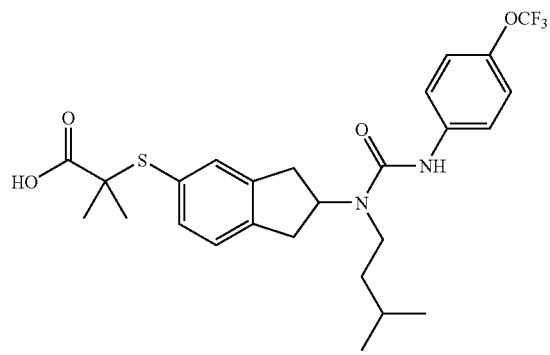

2-Methyl-2-{2-[1-(3-methylbutyl)-3-(4-trifluoromethoxyphenyl)ureido]indan-5-ylsulfanyl}-2-methylpropionic acid $EC_{50}$=0.106 µM Example 21

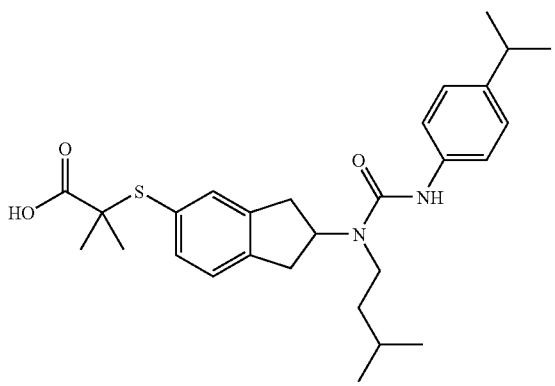

2-{2-[3-(4-Isopropyl phenyl)-1-(3-methylbutyl)ureido]indan-5-ylsulfanyl}-2-methylpropionic acid $EC_{50}$=0.106 µM Example 22

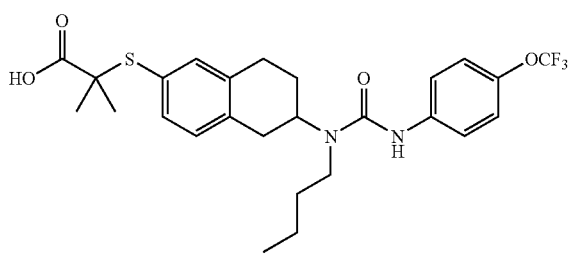

2-{6-[1-Butyl-3-(4-trifluoromethoxyphenyl)ureido]-5,6,7,8-tetrahydronaphthalen-2-ylsulfanyl}-2-methylpropionic acid $EC_{50}$=0.219 µM Example 23

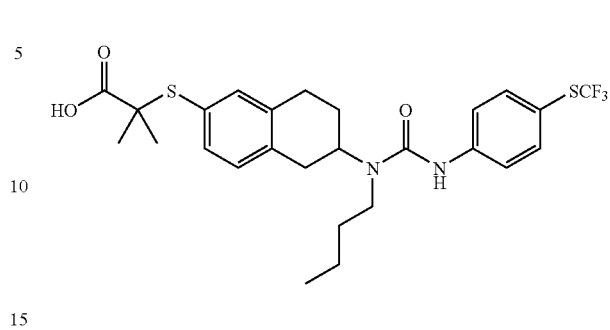

2-{6-[1-Butyl-3-(4-trifluoromethylsulfanylphenyl)ureido]-5,6,7,8-tetrahydronaphthalen-2-ylsulfanyl}-2-methylpropionic acid $EC_{50}$=0.244 µM Example 24

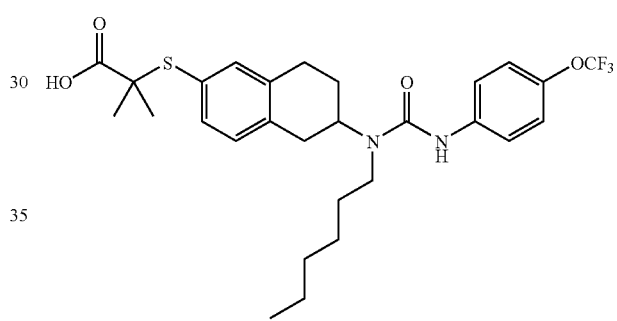

2-{6-[1-Hexyl-3-(4-trifluoromethoxyphenyl)ureido]-5,6,7,8-tetrahydronaphthalen-2-ylsulfanyl}-2-methylpropionic acid $EC_{50}$=0.235 µM Example 47

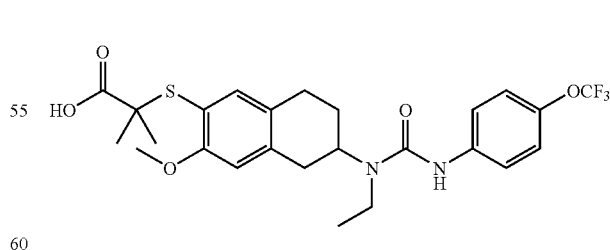

2-{6-[1-Ethyl-3-(4-trifluoromethoxyphenyl)ureido]-3-methoxy-5,6,7,8-tetrahydronaphthalen-2-ylsulfanyl}-2-methylpropionic acid $EC_{50}$=0.045 µM Example 49

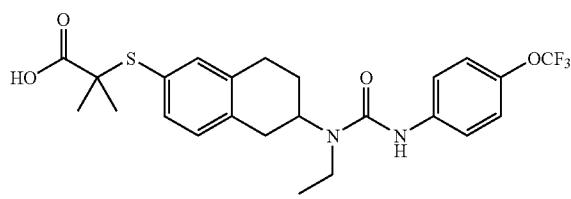

2-{6-[1-Ethyl-3-(4-trifluoromethoxy-phenyl)-ureido]-5,6,7,8-tetrahydro-naphthalen-2-yloxy}-2-methyl-propionic acid $EC_{50}$=0.309 µM Example 50

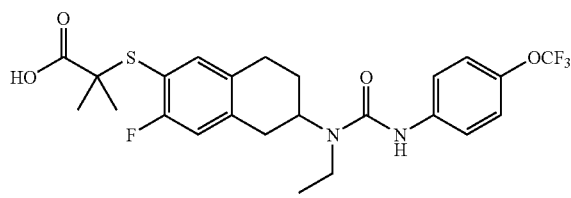

2-{6-[1-Ethyl-3-(4-trifluoromethoxyphenyl)ureido]-3-fluoro-5,6,7,8-tetrahydronaphthalen-2-ylsulfanyl}-2-methylpropionic acid $EC_{50}$=0.010 µM Example 51

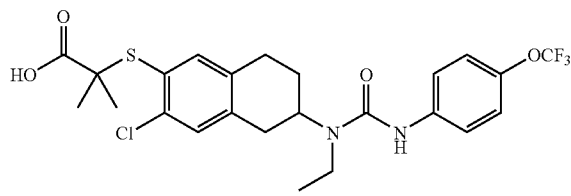

2-{6-[1-Ethyl-3-(4-trifluoromethoxyphenyl)ureido]-3-chloro-5,6,7,8-tetrahydronaphthalen-2-ylsulfanyl}-2-methylpropionic acid $EC_{50}$=0.027 µM Example 52

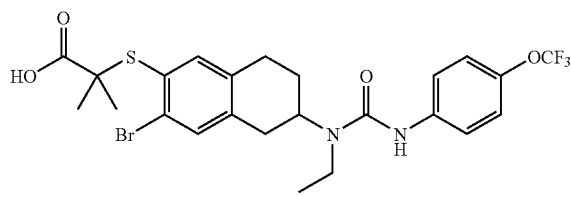

2-{6-[1-Ethyl-3-(4-trifluoromethoxyphenyl)ureido]-3-bromo-5,6,7,8-tetrahydronaphthalen-2-ylsulfanyl}-2-methylpropionic acid $EC_{50}$=0.017 µM Example 53

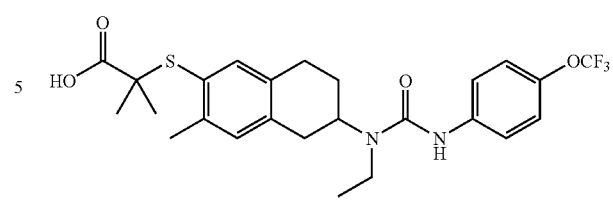

2-{6-[1-Ethyl-3-(4-trifluoromethoxyphenyl)ureido]-3-methyl-5,6,7,8-tetrahydronaphthalen-2-ylsulfanyl}-2-methylpropionic acid $EC_{50}$=0.042 µM Example 54

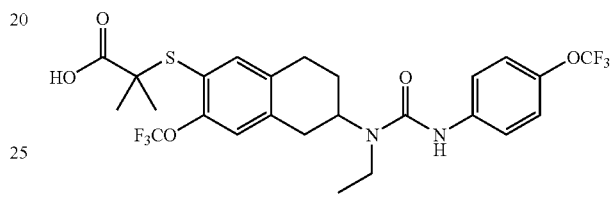

2-{6-[1-Ethyl-3-(4-trifluoromethoxyphenyl)ureido]-3-trifluoromethoxy-5,6,7,8-tetrahydronaphthalen-2-ylsulfanyl}-2-methylpropionic acid $EC_{50}$=0.131 µM Example 55

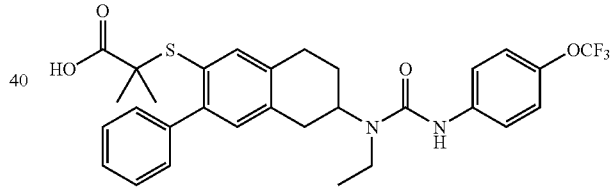

2-{6-[1-Ethyl-3-(4-trifluoromethoxyphenyl)ureido]-3-phenyl-5,6,7,8-tetrahydronaphthalen-2-ylsulfanyl}-2-methylpropionic acid $EC_{50}$=0.545 µM Example 56

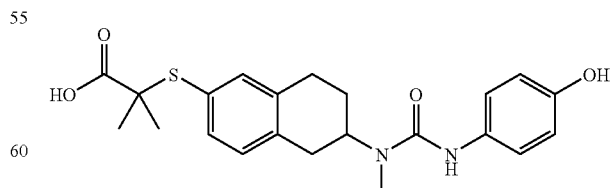

2-{6-[1-Ethyl-3-(4-hydroxyphenyl)ureido]-5,6,7,8-tetrahydronaphthalen-2-ylsulfanyl}-2-methylpropionic acid

Example 57

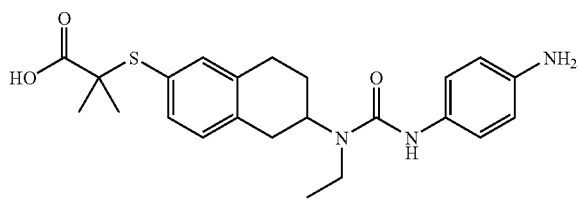

2-{6-[4-Aminophenyl)-1-ethyl-ureido]-5,6,7,8-tetrahydronaphthalen-2-ylsulfanyl}-2-methylpropionic acid

Example 58

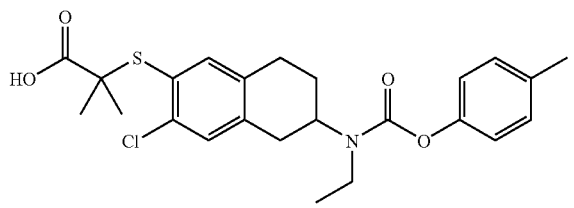

2-{3-Chloro-6-[(4-methyl-phenoxycarbonyl)-ethyl-amino]-5,6,7,8-tetrahydronaphthalen-2-ylsulfanyl}-2-methyl-propionic acid $EC_{50}$=0.340 µM

Example 59

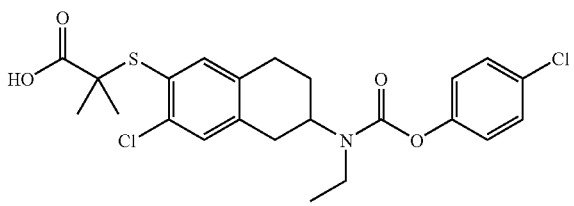

2-{3-Chloro-6-[(4-chloro-phenoxycarbonyl)-ethyl-amino]-5,6,7,8-tetrahydronaphthalen-2-ylsulfanyl}-2-methyl-propionic acid $EC_{50}$=0.390 µM

Example 60

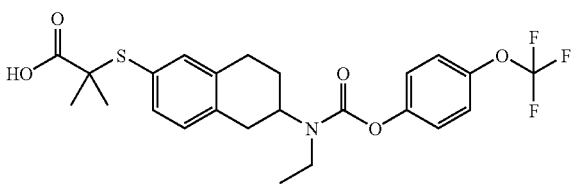

2-{6-[Ethyl-(4-trifluoromethoxy-phenoxycarbonyl)-amino]-5,6,7,8-tetrahydronaphthalen-2-ylsulfanyl}-2-methyl-propionic acid $EC_{50}$=0.002 µM

Biological Example 1

HD bDNA Assay

H4IIE rat hepatoma cell line was obtained from ATCC. Cells were cultured in 175 cm² tissue culture flask or seeded in 96-well plate with (high serum content, 10% fetal bovine serum and 10% calf serum) culture medium and maintained at 37° C. and 5% CO2 throughout study. Twenty-four hours after the initial seeding of the 96-well plate by hand (approximate 100,000/well), the HD gene induction assay was initiated. Media was removed and replaced with 100 ul of low serum culture media (5% charcoal/dextran treated calf serum) containing vehicle (DMSO) or test compounds or standard. Cells returned to incubator for 24 hours culture. At the termination of the challenge, 50 ul lysis buffer with HD gene specific CE, LE, BL probes was added directly into each well to initiate the bDNA HD mRNA assay. The branched DNA assay was performed according to the manufacturer's protocol (Bayer Diagnostics; Emeryville, Calif.). At the end of the assay, the luminescence was quantitated in Dynex MLX microtiter plate luminometer. $EC_{50}$'s were determined by non-linear regression with a sigmoidal fit utilizing Graphpad Prism.

Biological Example 2

Transfection Assay for PPARδ Receptors

HEK293 cells were grown in DMEM/F-12 Media supplemented with 10% FBS and glutamine (GIBCOBRL). The cells were co-transfected with DNA for PPAR-Gal4 receptor and Gal4-Luciferase Reporter using the DMRIE-C Reagent. On the following day, the DNA-containing medium were replaced with 5% Charcoal treated FBS growth medium. After six hours, cells were seeded in 96 well plate and incubated at 37° C. in $CO_2$ incubator overnight. Cells were challenged by test compounds and incubated for 24 hours at 37° C. in 5% $CO_2$ incubator. Luciferase activity was assayed using the Steady-Glo Luciferase Assay Kit from Promega. DMRIE-C Reagent was purchased from GIBCO Cat. No. 10459-014. OPTI-MEM I Reduced Serum Medium was purchased from GIBCO Cat. No. 31985. Steady-Glo Luciferase Assay Kit was obtained from Promega Part# E254B.

| | In Vitro Data | | |
|---|---|---|---|
| Example | PPARα $EC_{50}$ (µM) | PPARδ FI*[1] [$EC_{50}$ (µM)] | PPARγ FI*[2] [$EC_{50}$ (µM)] |
| 1 | 0.023 | | |
| 2 | 0.027 | 4.2 | 0.24 |
| 3 | 0.008 | [>10] | [>10] |
| 4 | 0.037 | | 3.7 |
| 5 | 0.053 | 2.5 | 4.0 |
| 6 | 0.056 | 3.6 | 1.9 |
| 7 | 0.075 | 0.8 | 0 |
| 8 | 0.073 | 5.9 | 1.9 |
| 9 | 0.131 | 1.0 | 2.9 |
| 10 | 0.165 | | 5.1 |
| 11 | 0.173 | | 6.1 |
| 12 | 0.183 | | 11 |
| 13 | 0.184 | | 1.2 |

-continued

In Vitro Data

| Example | PPARα EC$_{50}$ (μM) | PPARδ FI*[1] [EC$_{50}$ (μM)] | PPARγ FI*[2] [EC$_{50}$ (μM)] |
|---|---|---|---|
| 14 | 0.213 | 1.3 | 0.3 |
| 15 | 0.123 | 1.2 | |
| 16 | 0.158 | | 0.37 |
| 17 | 0.160 | | 0.43 |
| 18 | 0.135 | | 0.31 |
| 19 | 0.125 | 1.4 | |
| 20 | 0.106 | | 0.44 |
| 21 | 0.106 | | 0.05 |
| 22 | 0.219 | | |
| 23 | 0.244 | | |
| 24 | 0.235 | | |
| 25 | 0.208 | 4.5 | |
| 26 | 0.130 | 2.1 | |
| 27 | 0.294 | | |
| 28 | 0.323 | 8.2 | |
| 29 | 0.382 | | |
| 30 | 0.385 | | |
| 31 | 0.497 | | |
| 32 | 0.497 | 1.5 | |
| 33 | 0.537 | 0.8 | |
| 34 | 0.657 | | |
| 35 | 0.772 | 5.6 | |
| 36 | 0.796 | | |
| 37 | 0.838 | 1.9 | |
| 38 | 0.950 | | |
| 39 | 1.00 | 9.3 | |
| 40 | 1.30 | | |
| 41 | 2.21 | | |
| 42 | 2.34 | | |
| 43 | 2.99 | | |
| 44 | 2.09 | | |
| 45 | 0.780 | | |
| 46 | 1.39 | 6.0 | |
| 47 | 0.045 | [>3] | |
| 48 | 0.014 | [>3] | |
| 49 | 0.309 | [>3] | |
| 50 | 0.010 | [>3] | [>3] |
| 51 | 0.027 | [>10] | |
| 52 | 0.017 | [>3] | |
| 53 | 0.042 | [0.873] | |
| 54 | 0.131 | [>3] | |
| 55 | 0.545 | [1.72] | |
| 58 | 0.340 | [0.613] | [>3] |
| 59 | 0.390 | [0.655] | [1.11] |
| 60 | 0.002 | [>3] | [>3] |

*[1]Fold induction for PPARδ standard: FI = 36.1
*[2]Fold induction for PPARγ standard: FI = 70.3

Biological Example 3 aP2 Assay for PPAR Gamma Agonists

The procedure is described in detail in Burris et al., Molecular Endocrinology, 1999, 13:410, which is hereby incorporated by reference in its entirety, and aP2 assay results of agonist intrinsic activity may be presented as fold increase over vehicle in induction of aP2 mRNA production.

Twenty-four hours after the initial seeding of the 96-well plates by hand (around 20,000/well), the differentiation assay may be initiated. Medium may be removed and replaced with 150 μl of differentiation medium containing vehicle (DMSO) or test compounds. Cells may be returned to incubator for 24 hours culture. At the termination of the challenge, medium may be removed and 100 ul of lysis buffer may be added to initiate the bDNA aP2 mRNA assay. The branched DNA assay may be performed according to the manufacturer's protocol (Bayer Diagnostics; Emeryville, Calif.). Result may be expressed as the fold increase of aP2 mRNA production activated over vehicle controls. EC$_{50}$'s and Emax may be determined by non-linear regression with a sigmoidal fit curve.

Following the challenge of the preadipocytes, cells may be lysed with lysis buffer (Bayer Diagnostics) containing the aP2 oligonucleotides. After a 15 minute incubation at 53° C. or 30 minutes at 37° C. incubator, 70 ul of the lysis buffer from each well may be added to a corresponding capture well (preincubated with 70 ul of blocking buffer (Bayer Diagnostics)). The capture plate may be incubated overnight at 53° C. in a plate incubator (Bayer Diagnostics). After this incubation, the bDNA and labeled probes may be annealed as directed by the manufacturer. Following a 30-minute incubation with the luminescent alkaline phosphatase substrate, dioxitane, the luminescence may be quantitated in a Dynex MLX microtiter plate luminometer. Oligonucleotide probes designed to anneal to the aP2 mRNA and function in the bDNA mRNA detection system are designed with Probe-Designer software (Bayer Diagnostics). This software package analyzes a target sequence of interest with a series of algorithms in order to determine which regions of the sequence can perform as locations for capture, label, or spacer probe annealing. The sequences of the oligonucleotides are as follows:

```
CATTTTGTGAGTTTTCTAGGATTATTCTTTTCTCTTGGAAAGAAAGT    SEQ ID NO.1

ATGTTAGGTTTGGCCATGCCTTTCTCTTGGAAAGAAAGT           SEQ ID NO.2

CCTCTCGTTTTCTCTTTATGGTTTTCTCTTGGAAAGAAAGT         SEQ ID NO.3

GCTTATGCTCTCTCATAAACTCTCGTGGTTTCTCTTGGAAAGAAAGT   SEQ ID NO.4

CCAGGTACCTACAAAAGCATCACATTTAGGCATAGGACCCGTGTCT    SEQ ID NO.5

GCCCACTCCTACTTCTTTCATATAATCATTTAGGCATAGGACCCGTGTCT SEQ ID NO.6

AGCCACTTTCCTGGTGGCAAATTTAGGCATAGGACCCGTGTCT       SEQ ID NO.7

CATCCCCATTCACACTGATGATCTTTAGGCATAGGACCCGTGTCT     SEQ ID NO.8

GTACCAGGACACCCCCATCTAAGGTTTTTAGGCATAGGACCCGTGTCT  SEQ ID NO.9

GGTTGATTTTCCATCCCATTTCTGCACATTTTAGGCATAGGACCCGTGTCT SEQ ID NO.10

GCATTCCACCACCAGTTTATCATTTTAGGCATAGGACCCGTGTCT     SEQ ID NO.11
```

```
                                                    -continued
GCGAACTTCAGTCCAGGTCAACGTCCCTTGTTTAGGCATAGGACCCGTGTCT    SEQ ID NO.12

TCCCACAGAATGTTGTAGAGTTCAATTTTAGGCATAGGACCCGTGTCT        SEQ ID NO.13

AAAACAACAATATCTTTTTGAACAATATATTTAGGCATAGGACCCGTGTCT     SEQ ID NO.14

TCAAAGTTTTCACTGGAGACAAGTTT                              SEQ ID NO.15

AAAGGTACTTTCAGATTTAATGGTGATCA                           SEQ ID NO.16

CTGGCCCAGTATGAAGGAAATCTCAGTATTTTT                       SEQ ID NO.17

TCTGCAGTGACTTCGTCAAATTC                                 SEQ ID NO.18

ATGGTGCTCTTGACTTTCCTGTCA                                SEQ ID NO.19

AAGTGACGCCTTTCATGAC                                     SEQ ID NO.20
```

Biological Example 4

11 Day Dosing of Example 3 in Female, 6-7 Week Old db/db Mice (Female db/db mice (C57 BLK S/J-m+/+Lepr$^{db}$, Jackson Labs, Bar Harbor, Me.), 6-7 weeks of age, were housed four per cage in solid-bottomed shoe box cages. Room temperature was maintained at 68-72° F. and humidity at 50-65%. Room lighting was on a 12-hour light/12-hour dark cycle. Mice were fed a certified NIH Rat and Mouse/Auto 6F reduced fat diet #5K52 (P M I Nutrition Int'l, St. Louis, Mo., via W. F. Fisher and Son, Inc., Bound Brook, N.J.). Food and water were supplied ad libitum.

The compound was prepared as suspensions in 0.5% hydroxypropyl-methylcellulose (Dow Chemical, Midland, Mich.). The dosing volume was 10 mL/kg of body weight. Female db/db diabetic mice (8/group) were orally gavaged once daily for 11 days with either 0.5% methylcellulose in dH$_2$O (vehicle) or PPARagonist at either 0.03, 0.1, 0.3, 1, 3, 10 mg/kg/day. Body weight was measured in the mornings on Day 1, prior to dosing, and on Day 12 before bleeding. 18-24 hours after the final dose for each group, the mice were anesthetized with CO$_2$/O$_2$ (70:30) and bled by retro-orbital sinus puncture into micro-tubes containing clog activator and then put in ice. The serum samples were prepared by centrifugation. Serum glucose and triglycerides were determined by using COBAS Mira Plus blood chemistry analyzer (Roche Diagnostics, N.J.). Serum insulin was measured by using ALPCO insulin ELISA kit.

Statistical analysis was performed using the program Prism (Graphpad, Monrovia, Calif.) and performing one-way ANOVA with a Dunnett's multiple comparison test.

| | In Vivo data | | |
|---|---|---|---|
| Example[1] | Δ Plasma TG | Δ Plasma Glucose | Δ Plasma Insulin |
| 1[2] | −52% | −73% | −46% |
| 2[3] | −56% | −60% | −53% |
| 3[4] | −66% | −66% | −69% |
| 4[4] | −47% | −49% | −13% |
| 5[4] | −19% | −31% | −43% |
| 6[4] | −50% | −49% | −19% |
| 7[4] | −63% | −44% | −40% |
| 8[4] | −27% | −28% | −38% |
| 9[4] | −6% | −13% | −40% |

[1]db/db Mice dosed @ 1.0 mpk. Data is represented as a % change compared to vehicle treated animals;
NC = no change
[2]10 day oral dosing
[3]11 day oral dosing
[4]5 day oral dosing Biological Example 5

11 Day Dosing of Example in Female, 7 Week Old ob/ob Mice (Female ob/ob mice (C57 BU6J-Lep$^{ob}$, Jackson Labs, Bar Harbor, Me.), 7 weeks of age, were housed two per cage in solid-bottomed shoe box cages. Room temperature was maintained at 68-72° F. and humidity at 50-65%. Room lighting was on a 12-hour light/12-hour dark cycle. Mice were fed a certified NIH Rat and Mouse diet #5K50 (P M I Nutrition Int'l, St. Louis, Mo., via W. F. Fisher and Son, Inc., Bound Brook, N.J.). Food and water were supplied ad libitum.

The compound was prepared as suspensions in 0.5% hydroxypropyl-methylcellulose (Dow Chemical, Midland, Mich.). The dosing volume was 10 mL/kg of body weight. Female ob/ob diabetic mice (8/group) were orally gavaged once daily for 11 days with either 0.5% methylcellulose in dH$_2$O (vehicle) or PPAR agonist at 0.003, 0.01, 0.03, 0.1, 0.3, 1 mg/kg/day. Body weight was measured in the mornings on Day 1, prior to dosing, and on Day 12 before bleeding. 18 hours after the final dose for each group, the mice were anesthetized with CO$_2$/O$_2$ (70%:30%) and bled by retro-orbital sinus puncture into micro-tubes containing clog activator and then put in ice. The serum samples were prepared by centrifugation. Serum glucose and triglycerides were determined by using COBAS Mira Plus blood chemistry analyzer (Roche Diagnostics, N.J.). Serum insulin and free fatty acids were measured by using ALPCO insulin ELISA kit and Wako NEFA kit, respectively.

Statistical analysis was performed using the program Prism (Graphpad, Monrovia, Calif.) with one-way ANOVA and a Dunnett's multiple comparison test.

In Vivo data

| Example[1] | Δ Plasma TG | Δ Plasma Glucose | Δ Plasma Insulin |
|---|---|---|---|
| 50 | −86% | −74% | −93% |

[1]ob/ob Mice dosed @ 1.0 mpk. Data is represented as a % change compared to vehicle treated animals.

E. Other Embodiments

The features and principles of the invention are illustrated in the discussion, examples, and claims herein. Various adaptations and modifications of the invention will be apparent to a person of ordinary skill in the art and such other embodiments are also within the scope of the invention. Publications cited herein are incorporated in their entirety by reference.

What is claimed is:

1. A compound of Formula I

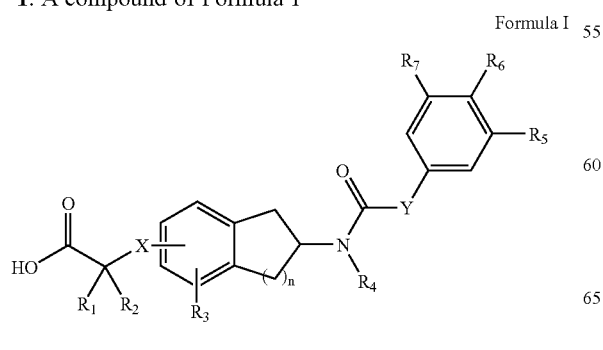

Formula I or a pharmaceutically acceptable salt, $C_{1-6}$ ester or $C_{1-6}$ amide thereof, wherein each of $R_1$ and $R_2$ is independently H, $C_{1-6}$ alkyl, $(CH_2)_m NR_a R_b$, $(CH_2)_m OR_8$, $(CH_2)_m NH(CO)R_8$, or $(CH_2)_m CO_2 R_8$, where each of $R_a$, $R_b$, and $R_8$ is independently H or $C_{1-6}$ alkyl, or $R_1$ and $R_2$ taken together with the carbon atom to which they are attached are a $C_{3-7}$ cycloalkyl;

m is between 1 and 6;

n is 1 or 2;

X is O or S; wherein X is at the 5 or 6 position when n is 1; and wherein X is at the 6 or 7 position when n is 2;

R$_3$ is H, phenyl, C$_{1-3}$ alkoxy, C$_{1-3}$ alkylthio, halo, cyano, C$_{1-6}$ alkyl, nitro, NR$_9$R$_{10}$, NHCOR$_{10}$, CONHR$_{10}$; and COOR$_{10}$; and R$_3$ is ortho or meta to X;

R$_4$ is H or —(C$_{1-5}$ alkylene)R$_{15}$, where R$_{15}$ is H, C$_{1-7}$ alkyl, [di(C$_{1-2}$ alkyl)amino](C$_{1-6}$ alkylene), (C$_{1-3}$ alkoxyacyl)(C$_{1-6}$ alkylene), C$_{1-6}$ alkoxy, C$_{3-7}$ alkenyl, or C$_{3-8}$ alkynyl, wherein R$_4$ has no more than 9 carbon atoms; R$_4$ can also be —(C$_{1-5}$ alkylene)R$_{15}$ wherein R$_{15}$ is C$_{3-6}$ cycloalkyl, phenyl, phenyl-O—, phenyl-S—, or a 5-6 membered heterocyclyl with between 1 and 2 heteroatoms selected from N, O, and S;

Y is NH, NH—CH$_2$, and O;

each of R$_5$ and R$_7$ is independently selected from H, C$_{1-6}$ alkyl, halo, cyano, nitro, COR$_{11}$, COOR$_{11}$, C$_{1-4}$ alkoxy, C$_{1-4}$ alkylthio, hydroxy, phenyl, NR$_{11}$R$_{12}$ and 5-6 membered heterocyclyl with between 1 and 2 heteroatoms selected from N, O, and S;

R$_6$ is selected from C$_{1-6}$ alkyl, halo, cyano, nitro, COR$_{13}$, COOR$_{13}$, C$_{1-4}$ alkoxy, C$_{1-4}$ alkylthio, hydroxy, phenyl, NR$_{13}$R$_{14}$ and 5-6 membered heterocyclyl with between 1 and 2 heteroatoms selected from N, O, and S;

in addition, either R$_5$ and R$_6$ or R$_6$ and R$_7$ may be taken together to be a bivalent moiety, saturated or unsaturated, selected from —(CH$_2$)$_3$—, —(CH$_2$)$_4$—, and (CH$_{1-2}$)$_p$N(CH$_{1-2}$)$_q$, p is 0-2 and q is 1-3, where the sum (p+q) is at least 2;

each of R$_9$ and R$_{10}$ is independently C$_{1-6}$ alkyl;

each of R$_{11}$, R$_{12}$, R$_{13}$ and R$_{14}$ is independently H or C$_{1-6}$ alkyl;

wherein each of the above hydrocarbyl and heterocarbyl moieties may be substituted with between 1 and 3 substituents independently selected from F, Cl, Br, I, amino, methyl, ethyl, hydroxy, nitro, cyano, and methoxy.

2. A compound of claim 1, wherein one of R$_1$ and R$_2$ is methyl or ethyl.

3. A compound of claim 2, wherein each of R$_1$ and R$_2$ is methyl.

4. A compound of claim 1, wherein R$_1$ and R$_2$ taken together are cyclobutyl or cyclopentyl.

5. A compound of claim 1, wherein R$_3$ is H.

6. A compound of claim 1, wherein R$_3$ is C$_{1-3}$ alkoxy, C$_{1-3}$ alkylthio, halo, cyano, C$_{1-6}$ alkyl, nitro, NR$_9$R$_{10}$, NHCOR$_{10}$, CONHR$_{10}$; or COOR$_{10}$.

7. A compound of claim 1, wherein R$_4$ is H or C$_{2-7}$ alkyl.

8. A compound of claim 7, wherein R$_4$ is H or C$_{2-5}$ alkyl.

9. A compound of claim 8, wherein R$_4$ is ethyl.

10. A compound of claim 8, wherein R$_4$ is H.

11. A compound of claim 1, wherein n is 1.

12. A compound of claim 1, wherein n is 2.

13. A compound of claim 1, wherein Y is NH—CH$_2$.

14. A compound of claim 1, wherein Y is NH.

15. A compound of claim 1, wherein X is S.

16. A compound of claim 1, wherein X is O.

17. A compound of claim 1, wherein at least one of R$_5$ and R$_7$ is H.

18. A compound of claim 17, wherein R$_6$ is C$_{1-4}$ alkyl, halomethoxy, halomethylthio, or di(C$_{1-3}$ alkyl)amino.

19. A compound of claim 18, wherein R$_6$ is trifluoromethoxy, difluoromethoxy, trifluoromethyl, trifluoromethylthio, t-butyl, isopropyl, or dimethylamino.

20. A compound of claim 3, wherein R$_3$ is H, R$_4$ is C$_{2-7}$ alkyl, and Y is NH.

21. A compound of claim 20, wherein X is S.

22. A compound of claim 20, wherein n is 1.

23. A compound of claim 20, wherein n is 2.

24. A compound of claim 20, wherein R$_4$ is C$_{2-5}$ alkyl.

25. A compound of claim 24, wherein R$_4$ is ethyl.

26. A compound of claim 20, wherein R$_6$ is trifluoromethoxy, difluoromethoxy, trifluoromethyl, trifluoromethylthio, t-butyl, isopropyl, or dimethylamino.

27. A compound of claim 1, wherein each of R$_1$ and R$_2$ is independently H, C$_{1-6}$ alkyl, (CH$_2$)$_m$NR$_a$R$_b$, or (CH$_2$)$_m$OR$_8$, where each of R$_a$, R$_b$, and R$_8$ is independently H or C$_{1-6}$ alkyl;

m is between 1 and 6;

n is 1 or 2;

X is O or S; wherein X is at the 5 or 6 position when n is 1; and wherein X is at the 6 or 7 position when n is 2;

R$_3$ is H, phenyl, C$_{1-3}$ alkoxy, C$_{1-3}$ alkylthio, halo, C$_{1-6}$ alkyl, or NR$_9$R$_{10}$, and R$_3$ is ortho or meta to X;

R$_4$ is H or —(C$_{1-5}$ alkylene)R$_{15}$, where R$_{15}$ is H, C$_{1-7}$ alkyl, [di(C$_{1-2}$ alkyl)amino](C$_{1-6}$ alkylene), (C$_{1-3}$ alkoxyacyl)(C$_{1-6}$ alkylene), C$_{1-6}$ alkoxy, or C$_{3-7}$ alkenyl, wherein R$_4$ has no more than 9 carbon atoms;

R$_4$ can also be —(C$_{1-5}$ alkylene)R$_{15}$ wherein R$_{15}$ is C$_{3-6}$ cycloalkyl, phenyl, phenyl-O—, phenyl-S—, or a 5-6 membered heterocyclyl with between 1 and 2 heteroatoms selected from N, O, and S;

Y is NH or NHCH$_2$;

each of R$_5$ and R$_7$ is independently selected from H, C$_{1-6}$ alkyl, halo, COR$_{11}$, COOR$_{11}$, C$_{1-4}$ alkoxy, C$_{1-4}$ alkylthio, hydroxy, and NR$_{11}$R$_{12}$;

R$_6$ is selected from C$_{1-6}$ alkyl, halo, COR$_{13}$, COOR$_{13}$, C$_{1-4}$ alkoxy, C$_{1-4}$ alkylthio, phenyl, NR$_{13}$R$_{14}$ and 5-6 membered heterocyclyl with between 1 and 2 heteroatoms selected from N, O, and S;

each of R$_9$ and R$_{10}$ is independently C$_{1-6}$ alkyl;

each of R$_{11}$, R$_{12}$, R$_{13}$ and R$_{14}$ is independently H or C$_{1-6}$ alkyl;

wherein each of the above hydrocarbyl and heterocarbyl moieties may be substituted with between 1 and 3 substituents independently selected from F, Cl, amino, methyl, ethyl, hydroxy, and methoxy.

28. A compound of claim 1, selected from:

2-{6-[1-Ethyl-3-(4-trifluoromethoxyphenyl)ureido]-5,6,7,8-tetrahydronaphthalen-2-ylsulfanyl}-2-methylpropionic acid;

2-{2-[1-Ethyl-3-(4-trifluoromethoxyphenyl)ureido]indan-5-ylsulfanyl}-2-methylpropionic acid;

2-{2-[1-Ethyl-3-(4-trifluoromethylsulfanylphenyl)ureido]indan-5-ylsulfanyl}-2-methylpropionic acid;

2-Methyl-2-{2-[1-pentyl-3-(4-trifluoromethylsulfanylphenyl)ureido]indan-5-ylsulfanyl}propionic acid;

2-{2-[1-Ethyl-3-(4-isopropylphenyl)ureido]indan-5-ylsulfanyl}-2-methylpropionic acid;

2-Methyl-2-{2-[1-pentyl-3-(4-trifluoromethoxyphenyl)ureido]indan-5-ylsulfanyl}propionic acid;

2-{2-[3-(4-Dimethylaminophenyl)-1-ethylureido]indan-5-ylsulfanyl}-2-propionic acid;

2-Methyl-2-{2-[1-(3-methylbutyl)-3-(4-trifluoromethoxyphenyl)ureido]indan-5-ylsulfanyl}propionic acid;

2-{2-[3-(4-Isopropylphenyl)-1-(3-methylbutyl)ureido]indan-5-ylsulfanyl}-2-methylpropionic acid;

2-Methy-2-{2-[1-pent-4-enyl-3-(4-trifluoromethoxyphenyl)ureido]indan-5-ylsulfanyl}propionic acid;

2-{6-[1-Ethyl-3-(4-trifluoromethoxyphenyl)ureido]-3-methoxy-5,6,7,8-tetrahydronaphthalen-2-ylsulfanyl}-2-methylpropionic acid;

2-{6-[1-Ethyl-3-(4-trifluoromethoxyphenyl)ureido]-3-fluoro-5,6,7,8-tetrahydronaphthalen-2-ylsulfanyl}-2-methylpropionic acid;

2-{6-[1-Ethyl-3-(4-trifluoromethoxyphenyl)ureido]-3-chloro-5,6,7,8-tetrahydronaphthalen-2-ylsulfanyl}-2-methylpropionic acid;
2-{6-[1-Ethyl-3-(4-trifluoromethoxyphenyl)ureido]-3-bromo-5,6,7,8-tetrahydronaphthalen-2-ylsulfanyl}-2-methylpropionic acid;
2-{6-[1-Ethyl-3-(4-trifluoromethoxyphenyl)ureido]-3-methyl-5,6,7,8-tetrahydronaphthalen-2-ylsulfanyl}-2-methylpropionic acid; and
2-{6-[1-Ethyl-3-(4-trifluoromethoxyphenyl)ureido]-3-trifluoromethoxy-5,6,7,8-tetrahydronaphthalen-2-ylsulfanyl}-2-methylpropionic acid.

29. A compound of claim 1, selected from
2-Methyl-2-{2-[1-hexyl-3-(4-trifluoromethylsulfanylphenyl)ureido]indan-5-ylsulfanyl}propionic acid;
2-{2-[3-(4-Dimethylaminophenyl)-1-pentylureido]indan-5-ylsulfanyl}-2-methylpropionic acid;
2-Methyl-2-{2-[3-(4-trifluoromethoxyphenyl)ureido]indan-5-ylsulfanyl}propionic acid;
2-Methyl-2-{2-[1-propyl-3-(4-trifluoromethoxyphenyl)ureido]indan-5-ylsulfanyl}propionic acid;
2-Methyl-2-{2-[1-butyl-3-(4-trifluoromethylsulfanylphenyl)ureido]indan-5-ylsulfanyl}propionic acid;
2-{2-[3-(4-Isopropylphenyl)-1-pentylureido]indan-5-ylsulfanyl}-2-methylpropionic acid;
2-{2-[3-(4-tert-Butylphenyl)-1-pentylureido]indan-5-ylsulfanyl}-2-methylpropionic acid;
2-[2-(3-Biphenyl-4-yl-1-pentylureido)indan-5-ylsulfanyl]-2-methylpropionic acid;
2-{2-[3-(4-Isopropylphenyl)-1-hexylureido]indan-5-ylsulfanyl}-2-methylpropionic acid;
2-Methyl-2-{2-[1-butyl-3-(4-trifluoromethoxyphenyl)ureido]indan-5-ylsulfanyl}propionic acid;
2-{6-[1-Ethyl-3-(4-trifluoromethoxyphenyl)ureido]-3-methoxy-5,6,7,8-tetrahydronaphthalen-2-ylsulfanyl}-2-methylpropionic acid;
2-{6-[1-Ethyl-3-(4-trifluoromethoxyphenyl)ureido]-3-fluoro-5,6,7,8-tetrahydronaphthalen-2-ylsulfanyl}-2-methylpropionic acid;
2-{6-[1-Ethyl-3-(4-trifluoromethoxyphenyl)ureido]-3-chloro-5,6,7,8-tetrahydronaphthalen-2-ylsulfanyl}-2-methylpropionic acid;
2-{6-[1-Ethyl-3-(4-trifluoromethoxyphenyl)ureido]-3-bromo-5,6,7,8-tetrahydronaphthalen-2-ylsulfanyl}-2-methylpropionic acid;
2-{6-[1-Ethyl-3-(4-trifluoromethoxyphenyl)ureido]-3-methyl-5,6,7,8-tetrahydronaphthalen-2-ylsulfanyl}-2-methylpropionic acid; and
2-Methyl-2-{2-[1-hexyl-3-(4-trifluoromethoxyphenyl)ureido]indan-5-ylsulfanyl}propionic acid.

30. A compound of claim 1, selected from:
2-{6-[1-Ethyl-3-(4-trifluoromethoxyphenyl)ureido]-5,6,7,8-tetrahydronaphthalen-2-ylsulfanyl}-2-methylpropionic acid;
2-{6-[3-(4-Trifluoromethoxyphenyl)ureido]-5,6,7,8-tetrahydronaphthalen-2-ylsulfanyl}-2-methylpropionic acid;
2-{2-[1-Ethyl-3-(4-trifluoromethoxyphenyl)ureido]indan-5-ylsulfanyl}-2-methylpropionic acid;
2-{6-[1-Ethyl-3-(4-trifluoromethoxyphenyl)ureido]-3-fluoro-5,6,7,8-tetrahydronaphthalen-2-ylsulfanyl}-2-methylpropionic acid;
2-{6-[1-Ethyl-3-(4-trifluoromethoxyphenyl)ureido]-3-methyl-5,6,7,8-tetrahydronaphthalen-2-ylsulfanyl}-2-methylpropionic acid;
2-{2-[1-Ethyl-3-(4-trifluoromethylsulfanylphenyl)ureido]indan-5-ylsulfanyl}-2-methylpropionic acid; and
2-Methyl-2-{2-[1-propyl-3-(4-trifluoromethoxyphenyl)ureido]indan-5-ylsulfanyl}propionic acid.

31. A compound of claim 1, selected from:
2-{2-[1-Ethyl-3-(4-trifluoromethoxyphenyl)ureido]indan-5-ylsulfanyl}-2-methylpropionic acid;
2-{2-[1-Ethyl-3-(4-trifluoromethylsulfanylphenyl)ureido]indan-5-ylsulfanyl}-2-methylpropionic acid;
2-Methyl-2-{2-[1-propyl-3-(4-trifluoromethoxyphenyl)ureido]indan-5-ylsulfanyl}propionic acid; and
2-{6-[1-Ethyl-3-(4-trifluoromethoxyphenyl)ureido]-3-fluoro-5,6,7,8-tetrahydronaphthalen-2-ylsulfanyl}-2-methylpropionic acid.

32. A pharmaceutical composition, comprising a compound of claim 1, 20, 27, 28, 30, or 31.

33. A method for treating the progression of a PPAR-alpha mediated disease, said method comprising administering to a patient in need of treatment a pharmaceutically-effective amount of a composition comprising a compound of claim 1, 20, 27, 28 or 31, wherein said PPAR-alpha mediated disease is selected from impaired glucose tolerance, hyperinsulinemia, hyperglycemia, insulin resistance, and early, intermediate or late Type II diabetes (NIDDM), and complications thereof.

34. A method of claim 33, wherein said complication is selected from retinopathy, nephropathy, and neuropathy.

35. A method of claim 33, wherein said PPAR-alpha mediated disease is selected from impaired glucose tolerance, insulin resistance, hyperglycemia, hyperinsulinemia, and early Type II diabetes, and complications thereof.

36. A method of claim 33, wherein said PPAR-alpha mediated disease is selected from intermediate or late Type II diabetes, and complications thereof.

37. A method of claim 33, wherein said compound of claim 1, 20, 27, 28, or 31 is a first anti-diabetic agent, and wherein said method further comprises the step of administering to the patient a jointly-effective amount of a second anti-diabetic agent.

38. A method of claim 37, wherein said second anti-diabetic agent is selected from PPAR alpha and PPAR gamma modulating agents.

39. A method of claim 37, wherein said second anti-diabetic agent is insulin.

40. A method of claim 33, further comprising the step of administering a jointly-effective amount of a third pharmaceutically active agent.

41. A method of claim 40, wherein said third pharmaceutically active agent is selected from an anti-diabetic agent, a lipid lowering agent, and a blood-pressure lowering agent.

42. A method for treating the progression of a PPAR-alpha mediated disease and for treating or inhibiting the progression of dyslipidemia, said method comprising administering to a patient in need of treatment a pharmaceutically-effective amount of a composition comprising a compound of claim 1, 20, 27, 28 or 31, wherein said PPAR-alpha mediated disease is selected from impaired glucose tolerance, hyperinsulinemia, insulin resistance, and early, intermediate or late Type II diabetes (NIDDM), and complications thereof.

43. A method of claim 42, wherein said composition consists essentially of a compound of claim 1, 20, 27, 28, or 31.

* * * * *